(12) United States Patent
Geva et al.

(10) Patent No.: US 7,640,055 B2
(45) Date of Patent: Dec. 29, 2009

(54) SELF-ADAPTIVE SYSTEM FOR THE ANALYSIS OF BIOMEDICAL SIGNALS OF A PATIENT

(75) Inventors: Amir Geva, Meitar (IL); Baruch Levi, Nes Ziona (IL); Kobi Todros, Beer-Sheva pob (IL); Assaf Pressman, Lehavim (IL); Arye Mergi, Hod Hasharon (IL)

(73) Assignee: Widemed Ltd., Herzlia (IL)

( * ) Notice: Subject to any disclaimer, the term of this patent is extended or adjusted under 35 U.S.C. 154(b) by 1171 days.

(21) Appl. No.: 10/677,176

(22) Filed: Oct. 2, 2003

(65) Prior Publication Data
US 2004/0073098 A1    Apr. 15, 2004

Related U.S. Application Data

(63) Continuation of application No. PCT/IL03/00005, filed on Jan. 2, 2003.

(30) Foreign Application Priority Data

Jan. 7, 2002   (IL)   .................................... 147502

(51) Int. Cl.
*A61B 5/04* (2006.01)
(52) U.S. Cl. ...................... 600/544; 600/300
(58) Field of Classification Search ............... 600/300, 600/544
See application file for complete search history.

(56) References Cited

U.S. PATENT DOCUMENTS

| | | | |
|---|---|---|---|
| 4,589,420 A * | 5/1986 | Adams et al. ............... 600/515 |
| 4,777,962 A | 10/1988 | Watson et al. |
| 5,101,831 A | 4/1992 | Koyama et al. |
| 5,187,657 A | 2/1993 | Forbes |
| 5,271,411 A * | 12/1993 | Ripley et al. ............... 600/515 |
| 5,280,791 A | 1/1994 | Lavie et al. |
| 5,605,158 A * | 2/1997 | Snell ....................... 600/508 |
| 5,803,066 A | 9/1998 | Rapoport et al. |
| 5,819,007 A | 10/1998 | Elghazzawi ............... 395/51 |
| 5,846,208 A * | 12/1998 | Pichlmayr et al. ......... 600/544 |
| 5,999,846 A | 12/1999 | Pardey et al. |

(Continued)

OTHER PUBLICATIONS

A. Kaplan et al.: 'Macrostructural EEG characterization based on nonparametric change point segmentation: application to sleep analysis', Journal of Neuroscience Methods 106 (2001) 81-90.*

(Continued)

*Primary Examiner*—Patricia Mallari
*Assistant Examiner*—Karen E Toth

(57) ABSTRACT

Methods and systems that (a) adaptively segment a raw data stream(s) of different type biomedical signals; (b) assign attribute values to each segment; (c) determine an attribute domain based on a point corresponding to said segment attribute value; (d) generate a cluster set(s) in said attribute domain that includes a combination of points; (e) obtain a probability of order of appearance of each cluster point, according to its property value; (f) use said probability to update each point's property value; (g) repeat (d) through (f) while varying combinations of points in clusters according to their most updated property values and points derived from additional raw data stream adaptive segmentations; (h) associate at least one updated cluster with a normal/abnormal physiological state based on reference clusters in said domain; and (i) obtain the change probability between normal/abnormal physiological states using said probability of the order of appearance.

14 Claims, 42 Drawing Sheets

U.S. PATENT DOCUMENTS

| | | | |
|---|---|---|---|
| 6,070,098 | A | 5/2000 | Heitmann et al. ........... 600/544 |
| 6,142,950 | A | 11/2000 | Allen et al. |
| 6,223,064 | B1 | 4/2001 | Lynn et al. |
| 6,375,623 | B1 | 4/2002 | Gavriely et al. |
| 6,511,424 | B1* | 1/2003 | Moore-Ede et al. ......... 600/300 |
| 6,529,752 | B2 | 3/2003 | Krausman et al. |
| 6,549,804 | B1 | 4/2003 | Osorio et al. |
| 6,589,188 | B1 | 7/2003 | Street et al. |
| 6,595,929 | B2 | 7/2003 | Stivoric et al. .............. 600/549 |
| 6,839,581 | B1 | 1/2005 | El-Solh et al. |
| 6,881,192 | B1 | 4/2005 | Park |
| 7,160,252 | B2 | 1/2007 | Cho et al. |
| 7,324,845 | B2 | 1/2008 | Mietus et al. |
| 2002/0002327 | A1 | 1/2002 | Grant et al. |
| 2003/0004652 | A1 | 1/2003 | Brunner et al. |
| 2003/0144597 | A1* | 7/2003 | Bock .......................... 600/519 |
| 2004/0068199 | A1* | 4/2004 | Echauz et al. ............... 600/544 |
| 2004/0193068 | A1 | 9/2004 | Burton et al. |
| 2005/0076908 | A1 | 4/2005 | Lee et al. |
| 2005/0080349 | A1 | 4/2005 | Okada et al. |
| 2005/0148893 | A1 | 7/2005 | Misczynski et al. |
| 2006/0041201 | A1 | 2/2006 | Behbehani et al. |
| 2007/0016095 | A1* | 1/2007 | Low et al. ................... 600/544 |
| 2007/0118054 | A1 | 5/2007 | Pinhas et al. |
| 2007/0208269 | A1 | 9/2007 | Mumford et al. |
| 2007/0239057 | A1 | 10/2007 | Pu et al. |
| 2007/0244408 | A1* | 10/2007 | Wingeier et al. ............. 600/544 |
| 2008/0177195 | A1* | 7/2008 | Armitstead ................. 600/529 |

OTHER PUBLICATIONS

Agarwal, R., and Gotman, J. (2001): 'Computer-assisted sleep staging', IEEE Trans. Biomed. Eng., 48, pp. 1412-1423.*

G. Bodenstein and H.M. Praetorius (1977). Feature extraction from the encephalogram by adaptive segmentation. Proc. IEEE, vol. 65, pp. 642-652.*

I. Gath and A. B. Geva, "Unsupervised optimal fuzzy clustering," IEEE Trans. Patt. Anal. Machine Intell., vol. 11, No. 7, Jul. 1989.*

Roberts and Tarassenko, 1992. S. Roberts and L. Tarassenko, New method for automated sleep quantification. Med. Biol. Eng. Comp. 30 (1992), pp. 509-517.*

Amir B. Geva, et al., "Forecasting generalized epileptic seizures from the EEG signal by wavelet analysis and dynamic unsupervised fuzzy clustering", Trans. On Biomedical Eng. vol. 45, No. 10, Oct. 1998, p. 1205.

Lempel et al., "A Universal Algorithm for Sequential Data Compression", IEEE Transactions on Information Theory, IT-23:3 (1977), pp. 337-349.

Akselrod et al., "Power Spectrum Analysis of Heart Rate Fluctuation: A Quantitative Probe of Beat-to-Beat Cardiovascular Control", Science 213 (1981), pp. 220-222.

Eamonn Keogh, et al., "An Online Algorithm for Segmenting Time Series", pp. 289-296, 2001.

Penzel, et al., "Computer Based Sleep Recording and Analysis", Sleep Medicine Reviews 4:2 (2000), pp. 131-148.

Tesler, et al., "Can One Detect Sleep Stage Transitions for On-Line Sleep Scoring by Monitoring the Heart Rate Variabilitiy?" Somnologie 8 (2004), pp. 33-41.

A.K. Jain, et al., "Data Clustering: A Review", ACM Computing Surveys, vol. 31, No. 3, Sep. 1999.

http://www.sleepdisorderchannel.net, 2004.

M.G. Terzano, et al., "Atlas, rules, and recording techniques for the scoring of cyclic alternating pattern (CAP) in human sleep", Sleep Medicine 2 (2001), pp. 537-553.

Kevin Murphy, "Hidden Markov Model (HMM) Toolbox for Matlab," 1998, www.cs.ubc.ca/~murphyk/Software/HMM/hmm.html.

* cited by examiner

SELF-ADAPTIVE SYSTEM FOR THE ANALYSIS OF BIOMEDICAL SIGNALS OF A PATIENT

CLAIM OF PRIORITY

This application is a continuation application of PCT/IL03/00005, filed Jan. 2, 2003, which claims priority to IL 147502, filed Jan. 7, 2002, the contents of which aforementioned applications are incorporated herein by reference in their entireties.

FIELD OF THE INVENTION

The present invention relates to the field of biomedical analyzing systems. More particularly, the present invention relates to a method and system for allowing sampling, processing and analyzing a plurality of aggregated (noisy) biomedical signals, such as ElectroCardiogram (ECG), Electro-Encephalogram (EEG), Electro-Oculogram (EOG), Electromyogram (EMG), Oximetry and Respiratory signals, and for introducing to a clinician essentially noiseless and artifact-free biomedical event-wise and time-wise selections of analyzed data related to specific patient being monitored. The present invention also relates to a system that allows integrated analysis of ECG, EEG, EOG and respiratory signals while said system automatically adapting itself to the inherent biomedical parameters of said monitored patient. The present invention also relates to a Remote Medical Care system that allows remote monitoring of a person, by employing "Smart Compression" process on relevant physiological data and transferring the compressed data to remote end, for completing the evaluation process of the compressed data.

BACKGROUND OF THE INVENTION

Biomedical signals "suffer" from common problem of poor signal-to-noise ratio (SNR). This problem becomes acute whenever it comes to measuring ElecroEncyphalogram (EEG) and ElecroMyogram (EMG) signals, since the magnitude of such signals is generally in the $\mu^{Volt}$ range. The signals picked-up by corresponding detectors, which are attached to different portions of the patient body, are forwarded to the analyzing system by wires, which may add significant noise to the already weak signal. In addition, the characteristics of the wires may change according to the ambient conditions, a problem that must be overcome by utilizing special hardware and/or software resources. Another problem arises whenever the patient changes his relative position. Under such circumstances, the analyzing system may interpret false signals as valid pathological events. Therefore, it would be advantageous to have an analyzing system that is capable of recognizing and disregarding such false events.

In some conventional systems, wherein several physiological parameters of a patient are examined (e.g., EEG, ECG and EMG and respiratory), each parameter is analyzed regardless of other physiological parameters. However, in some cases, several parameters could be strongly interrelated. For example, an 'irregular' heartbeat rate (HBR) of a patient might be interpreted by a clinician as pathological HBR if analyzed regardless of other factors. However, it might be interpreted as proper HBR if correlated with brain waves indicating to the analyzing system that the patient is dreaming. Currently, in such systems a clinician has to 'manually' correlate the various raw measurements, which are related to different physiological aspects, and reach conclusions therefrom.

Therefore, it would be advantageous to have an analysis system, which would allow measuring several types of physiological signals, and could introduce to the clinician already-correlated data, i.e., a data that is already correlated with (other) relevant physiological parameters so as to eliminate artifacts and other types of noises/interference. Such a system would introduce to the clinician relevant, more accurate and well-characterized selected physiological events, and save the clinician analyzing/interpretation time. For example, it would be advantageous to combine abdominal effort, Oxygen saturation, patient's, movement or arousals, and sleep stages in order to reach a decision regarding apneas.

Different patients are likely to introduce different 'normal' physiological activities due to the variance of, e.g., heartbeat morphology (see FIGS. 1a and 1b). Therefore, it would be advantageous to have a system that would be capable of automatically adapting itself to the specific heartbeat morphology of a person being monitored, because such system would allow more accurate detection of physiological abnormalities.

Other conventional systems, generally called 'semi-automatic' systems, are capable of sampling, processing and analyzing electro-physiological signals. However, these systems configuration allows them to only analyze physiological signals between two 'rigid' boundaries, in time and/or in magnitude, which must be predetermined by the clinician. The two predetermined boundaries are selected on a random base, and, therefore, processing and analyzing the raw data contained within these boundaries usually does not yield satisfactory results. In some cases, the results could be even meaningless. Therefore, the clinician must iterate a sequence of operations, on a 'trial and error' basis, until meaningful results are obtained. Therefore, it would be advantageous to have a system that would be capable of 'self-tuning' to the required data portion, without needing to depend on specific or predetermined boundaries of any type, between which the raw data is to be processed and analyzed.

There are several common diseases associated with heart conditions, which are characterized by the corresponding irregularities in the heart behavior between distinguishable points in a heartbeat cycle (commonly known as points 'P', 'Q', 'R', 'S' and 'T'). FIGS. 1(a) and 1(b) illustrate typical heartbeats, in which the 'P', 'Q', 'R', 'S' and 'T' points are marked. Conventional systems utilize algorithms of rather limited flexibility (e.g., using 'rigid' predetermined boundaries). Therefore, they offer solutions that focus on limited aspects of heart analysis. For example, one system focuses on analyzing irregularities between points 'S' and 'T', another system on irregularities between points 'P' and 'R' etc. It would be advantageous to have a system that would be capable of isolating and classifying essentially every type of irregularity associated with a heart condition, regardless of the deformation (see FIGS. 1(b), 1(d) and 1(e)) and relative location of such irregularity.

Conventional systems usually display measurement results graphically on paper stripe or on electronic display, after which they are reviewed and estimated by a clinician or therapist. In some cases, these results are stored in an electronic storage media. Sometimes, the physiological activity of a patient is monitored for several hours but the clinician/therapist is interested only in small portions of the recorded data, which are associated with abnormal physiological activity of the patient. In conventional systems, the rest, and sometimes most, of the recorded data is useless because it is either too corrupted or it does not contribute anything to the assessment of the patient physiological condition, and is, therefore, dumped away (whenever a paper stripe is used), or a data storage place is unnecessarily consumed (whenever an electronic storage media is used), which leads to wasted resources. Other applications require collecting physiological signals of specific patient for several hours in order to allow good assessment of the patient physiological condition. In this case, the clinician must review and analyze an enormous amount of data, which is usually a burdensome process. The analysis lasts a long period of time and changes with technician tiredness. It would be advantageous to have a system, which is capable of performing the analysis with the same reliability.

In connection with sleep disorders, most current sleep (polysomnographic) studies are carried out in Sleep Centers, where patients need to spend at least one night in a hospital or private laboratory. The fact that patients need to sleep in the laboratory facilities presents significant difficulties. First, with the growing awareness to sleep disorders, waiting lists are growing, and delays of months and years are common. Second, the sleep study is expensive and thus the availability of sleep monitoring is more difficult. But more important fact is that the patient's sleep is affected whenever studied in a non-familiar laboratory setting. For example, sleep efficiency and patterns are badly affected due to the phenomena generally known as the "first night" effect. Therefore, in order to achieve a genuine sleep behavior of a patient, it is necessary to study the patient (especially for clinical research) for at least two consecutive nights, a fact that increases the expenses.

The advantages of conducting sleep studies at the patient home include increased flexibility of scheduling, less disruption to the routine of the child and family, and the ability to study the patient, especially a child, in his, or her, natural environment. While this has not yet been documented, it seems that home studies will be more cost-efficient than laboratory polysomnography, as a hospital admission is not required. Moreover, because such studies usually do not require the attendance of technicians, technician time is substantially decreased, or it could even be evaded. These factors become even more important when more than one night of recording is required.

More and more Sleep Centers are trying to screen their patients by performing partial ambulatory sleep studies at home. Although this is a growing field in sleep medicine, lacking automatic signal processing and monitoring greatly complicates the unattended tests.

A home video and partial cardiovascular electrode are successfully employed in Montreal, using a customized computer program. The possibility of using a simple, non-invasive data acquisition at home, monitored via a computer/Internet, on line, may facilitate home sleep monitoring for millions of patients. A patient will be able to remain in his own bedroom, for as long as required, while being continuously monitored and the data inspected on-line by a technician, enabling him to handle a problematic signal from the center or even call the patient at his home, to prevent waste of time due to disrupted data acquisition. In addition, the data will be analyzed on-line, in real time and automatically by the computer, thereby saving a lot of technician working hours and making the results readily available for both patient and his clinician.

Conventional systems produced by companies like Compumedics, Flaga, Respironoics, etc., are capable of automatically analyzing the mentioned signals. However, in order to achieve reliable results, an array of thresholds should be provided and adjusted manually in order for these systems to overcome the problem of different patients having different inherent signal variations and, thereby, to manually converge to the patient self-parameters.

There are major three frequency bands which characterize the EEG signal during sleep. The statistical characteristics of the frequency content of each group statistically differ from one person to another. Therefore, it is essential that a sleep monitoring system would have an adaptive mechanism, which would allow it to reach correct decisions regarding the interpretation of each frequency group on individual basis.

All of the methods described above have not yet provided satisfactory solutions to the problem of automatically adapting and optimizing the biomedical analyzing system to a patient being monitored. Additionally, the prior art methods have not yet provided satisfactory solutions to the problem of integrating analysis of ECG, EMG, EEG and respiratory signals.

SUMMARY OF THE INVENTION

The present invention is directed to a method for monitoring normal/abnormal physiological events in patients by analyzing his biomedical signals, such as EEG signals, EOG signals, EMG signals, ECG signals and Respiratory signals. For each patient, one or more raw data streams are aggregated, where each of which representing a different type of biomedical signals of the patient, in an accessible data storage. Segmentation of the raw data streams is performed adaptively to the patient for each type of biomedical signal, and individual attributes that are represented by attribute values are assigned to each segment. An attribute domain, in which each segment is represented by a point that corresponds to the attribute values of the segment, is determined. A set of clusters is generated in the attribute domain for each type of biomedical signal or for any combination thereof, each cluster including a combination of points determined by their relative location to other points by assigning a set of property values to each point such that each property value corresponds to the degree of association of the point with one of the clusters. The probability of the order of appearance of each point, in time, is obtained according to its property value and the property value of each point in each cluster is updated using the obtained probability. Each cluster is updated by repeating this process while in each time, the combination of points included in each cluster is varied according to their most updated property value and by including points derived from adaptive segmentation of further aggregated raw data streams of the patient. At least one updated cluster is associated with a normal/abnormal physiological state of the patient by using former knowledge, regarding normal/abnormal physiological states of the patient and/or of a reference group of patients, that is represented as reference clusters in the domain. The patient is individually characterized by identifying normal/abnormal physiological states, associated with one or more updated clusters, and obtaining the probability of a change between normal/abnormal physiological states using the probability of the order of appearance.

Indications related to abnormal physiological events in the patient are obtained by displaying changes and/or different stages in normal physiological states of the patient as a function of time. At least a portion of the aggregated raw data streams may be stored in an accessible data storage. Data segment that corresponds to an identified disorder may be retrieved from the accessible data storage.

Preferably, individual data being a group of updated clusters and/or indications of normal/abnormal physiological events in each patient represented by the group are generated.

Each individual data is divided into packets that are transmitted to a remote site over a data network. The data packets are receiving in the remote site, processed by a computerized system and a representation of normal/abnormal physiological events is displayed as a function of time and/or of changes in normal physiological states and/or different stages of normal/abnormal physiological states of each patient at the remote site.

A request for one or more segments of the raw data streams that correspond to abnormal physiological events may be transmitted from the remote site to the data storage over the data network. The requested segments are retrieved from the data storage and displayed at the remote site. Instructions for a medical treatment to be given to the patient for terminating the abnormal physiological events may be transmitted over the data network from the remote site to a local computerized system located at the vicinity of the patient. Data packets that correspond to an individual group of data clusters that corresponds to physiological events after applying the medical treatment to the patient are received at the remote site, and processed by the computerized system. A representation of physiological events, obtained in response to the medical treatment, are displayed as a function of time and/or of changes in normal physiological states and/or different stages of normal physiological states of each patient. This process is repeated until abnormal physiological events are eliminated or substantially reduced.

Raw data streams may be received from one or more dry electrodes attached to the skin of the patient and having movement detectors for identifying time periods during which segments of raw data streams are associated with patient movements.

The abnormal physiological events may comprise sleep apnea, cardiac arrhythmia, Ventricular Tachycardia, Ventricular Fibrillation/Flutter and epilepsy.

In one aspect, the raw data streams may be preprocessed by inputting the raw data streams to a cellular device having processing means that are capable of identifying irregular physiological events of the patient. A characteristic trace that corresponds to regular physiological events of the patient is generated by the cellular device that identifies selected raw data segments that comprise irregular physiological events and transmits the selected raw data segments over a cellular network to another computational device. The selected raw data segments are further processed and the processed raw data is represented by data clusters, each of which includes a set of unique properties that correspond to a different type of biomedical signal and to a different normal physiological state of the patient, by another computational device.

Preferably, the abnormal physiological events and/or the individual attributes of each patient are represented by an individual group of updated data clusters, which are divided into data packets that are transmitted to a remote site over a data network. The data packets are received in the remote site, processed by a computerized system and a representation of abnormal physiological events is displayed as a function of time and/or of changes in normal physiological states and/or different stages of normal physiological states of each patient at the remote site.

Preferably, irregular physiological events are identified for each patient, by another computational device. Segments of raw data that corresponds to the irregular physiological events are retrieved and a data set that comprises the retrieved segments and parameters indicating the irregularity of the irregular physiological events within the retrieved segments is generated. The data set is transmitted to a cellular device having processing means which are capable of displaying the parameters and the retrieved segments, over a cellular data network. The parameters and/or the retrieved segments are then displayed on the display of the cellular device.

In one aspect, alert indications representing abnormal physiological events are generated in real-time and automatically transmitted to a physician over a data network, for determining/providing the required medical treatment.

The operation of medical apparatus (such as, controllable drug dosage devices, controllable gas/air delivery devices, and CPAPs) used for providing medical treatment to a patient being in an abnormal state may be dynamically controlled in response to identified abnormal physiological events in the patient. Instructions for dynamically controlling medical equipment, providing medical treatment to the patient, for terminating the abnormal physiological events may be transmitted from the remote site to a local computerized system located at the vicinity of the medical equipment, over the data network.

The former knowledge may be capable of being continuously updated by manually modifying the characterization results, e.g., by a physician examining these results.

The present invention is also directed to a system for monitoring normal/abnormal physiological events in one or more patients by the analysis of biomedical signals of each patient, that comprises: (a) One or more sensors, attached or allocated to the patient, being capable of generating and transmitting biomedical signals; (b) a data storage for aggregating transmitted raw data streams, each of which representing a different type of biomedical signals of the patient; and (c) processing means, being in data communication with the sensors and/or the data storage, for performing adaptive segmentation of the raw data streams of the patient and assigning, to each segment, individual attributes being represented by attribute values determining an attribute domain, in which each segment being represented by a point, for generating a set of clusters in said attribute domain for each type of biomedical signal or for any combination thereof, such that each cluster includes a combination of points determined by their relative location to other points, by assigning a set of property values to each point, and such that each property value corresponds to the degree of association of said point with one of the clusters, for obtaining the probability of the order of appearance of each point, in time, according to its property value and updating the property value of each point in each cluster using said probability, for updating each cluster by iteratively varying the combination of points included in each cluster according to their most updated property value and by including points derived from adaptive segmentation of further aggregated raw data streams of said patient, for associating at least one updated cluster with a normal/abnormal physiological state of said patient by using former knowledge, regarding normal/abnormal physiological states of said patient and/or of a reference group of patients, that is represented as reference clusters in said domain and for individually characterizing said patient by identifying normal/abnormal physiological states, associated with one or more updated clusters, and obtaining the probability of a change between normal/abnormal physiological states using said probability of the order of appearance.

The system may further comprise display means for displaying different stages of normal physiological states of the patient as a function of time.

Preferably, the system further comprises (a) means for dividing data clusters and/or the representation of their corresponding physiological states into data packets; (b) means for transmitting the data packets of one or more patients to a remote site over a data network; (c) means for receiving the data packets in the remote site; and (d) means for processing the received data packets and displaying a representation of abnormal physiological events as a function of time and/or of changes in normal physiological states and/or different stages of normal physiological states of each patient at the remote site.

The system may further comprise (a) means for transmitting a request for one or more segments of the raw data streams that correspond to abnormal physiological events from the remote site to the data storage over the data network; and (b) means for retrieving the requested segments from the data storage and displaying the requested segments at the remote site.

One or more dry electrodes having movement detectors for generating and forwarding raw data streams may be attached to the skin of the patient and The system may further comprise: (a) a computational device having processing means for identifying abnormal physiological events in a patient, and being capable of generating a data set that comprises retrieved segments and parameters indicating the irregularity of the irregular physiological events within the retrieved segments and of transmitting the data set; and (b) a cellular device having processing means being capable of receiving the data set over a cellular data network, and a display for displaying the parameters and the retrieved segments.

It is an object of the present invention to provide a system that is capable of automatically adapting/optimizing itself to the patient being monitored.

It is another object of the present invention to provide a method and system for allowing integrating analysis of ECG, EEG and respiratory signals.

It is still another object of the present invention to provide a method and system for allowing extracting from same electro-physiological signal several data types, each of which being related to a different type of physiological activity.

It is a further object of the present invention to provide a method for allowing introducing to a clinician, according to his request, only selected biomedical data.

It is yet another object of the present invention to provide a method and system that allows efficient transmission of selected biological data to remote locations.

It is still another object of the present invention to provide a system that is capable of identifying sleep stages of a patient.

It is still a further object of the present invention to provide a method for allowing introducing to a clinician, upon request, data representing the physiological state of a patient, derived from his biomedical data.

Other objects and advantages of the invention will become apparent as the description proceeds.

BRIEF DESCRIPTION OF THE DRAWINGS

The above and other characteristics and advantages of the invention will be better understood through the following illustrative and non-limitative detailed description of preferred embodiments thereof, with reference to the appended drawings, wherein.

DETAILED DESCRIPTION OF PREFERRED EMBODIMENTS

Figure 1:
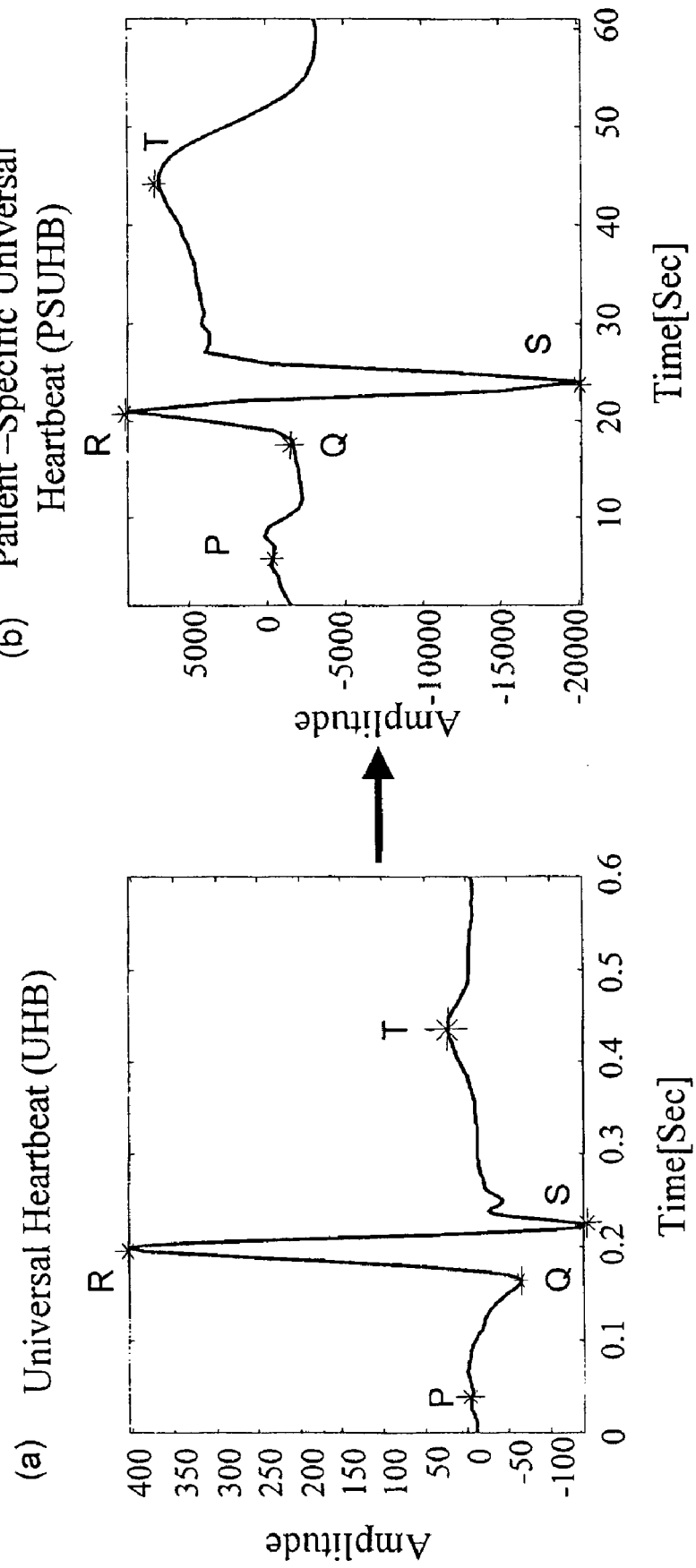
FIGS. 1a to 1e (prior art) schematically illustrate typical normal heartbeats shape and two commonly known aberrant heartbeat shapes.
Figure 1:
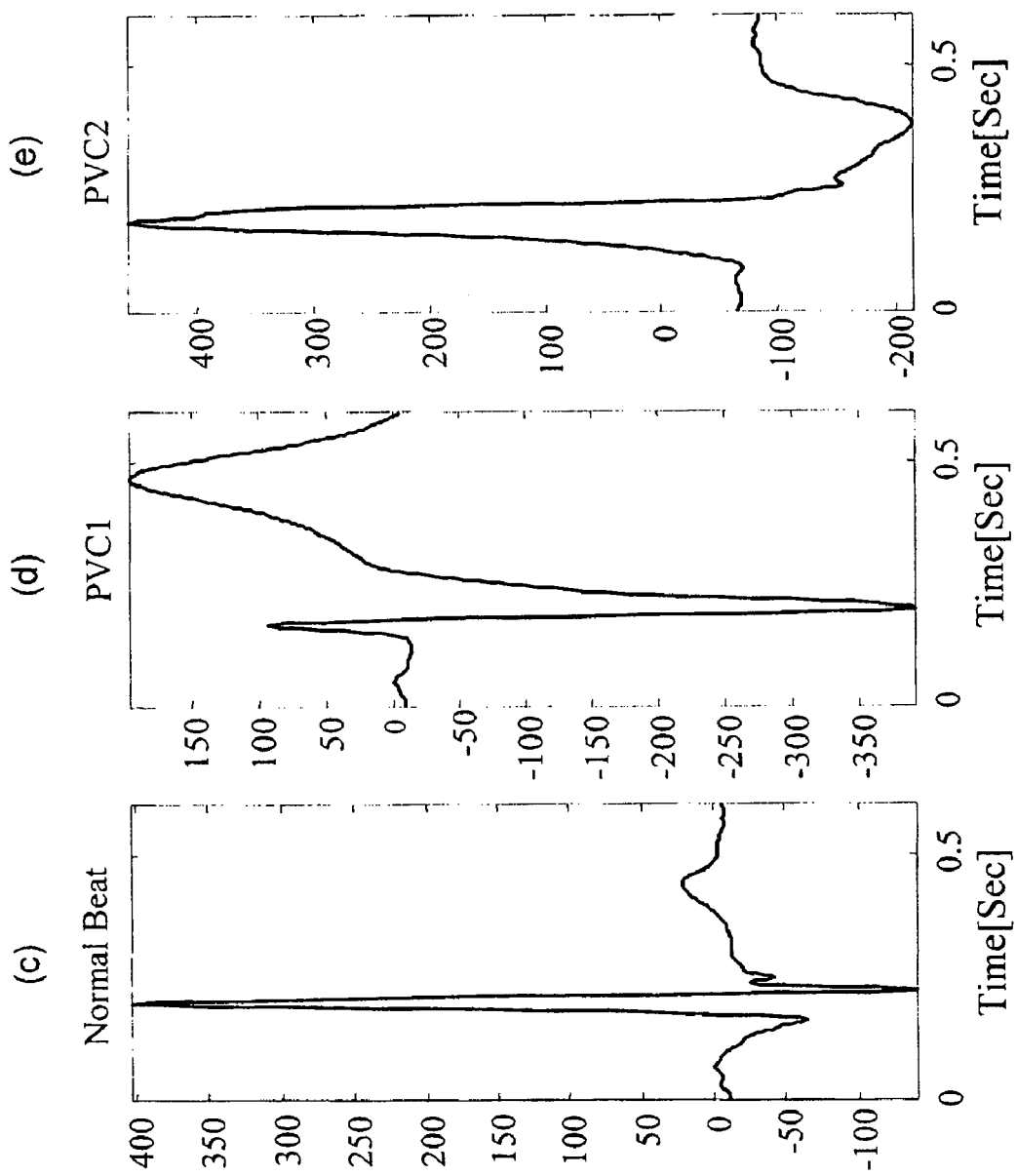

In one aspect, the present invention is directed to a biomedical-analyzing platform (hereinafter referred to as "Tele-Medicine Platform"—TMP) that is fast responsive, patient-adaptive and having high quality ambulatory remote monitoring of human biomedical signals, which are associated with cardiac status of a patient, his sleep patterns and respiratory behavior, by utilizing several known processing algorithms (i.e., HMM, Wavelet Transform algorithm and Viterbi) and novel Adaptive Segmentation Algorithms (ASA) and fuzzy-logic based decision-making algorithm. The present invention is also directed to a system that allows integrating analysis of a plurality of physiological signals.

General Introduction

The present invention is characterized by introducing a system that is patient-adaptive. According to the present invention, the system is capable of automatically adapting itself to the inherent cardiac, sleeping and respiratory status of individual patients, without having to manually match new sets of thresholds (on a 'trial and error' basis) for different patients being monitored. Therefore, the system optimizes itself to the persons being monitored on individual basis.

The present invention is further characterized by the way it utilizes known algorithms. In connection with the ECG signal, the present invention utilizes the (known) Wavelet Transform Algorithm (WTA) for adaptive segmentation of heartbeats. The system is also characterized by employing several digital Adaptive Matched Filters (AMFs) on the monitored (heart) Beat Under Test (BUT). An AMF is defined by a corresponding (shape) 'template', known as 'Matching Template', which is mathematically represented by a corresponding set of parameters. Different signal patterns/shapes may be identified by AMF by correspondingly defining other sets (i.e., templates) of parameters. The AMFs are utilized for allowing the system to detect and classify 'viable heartbeat' signal, and, after detecting several viable heartbeats (i.e., according to a predetermined criteria), to adapt to a person currently being monitored. By using the term 'viable heartbeat' it is meant to include every possible shape/pattern of a signal that resembles common Normal (see FIGS. 1a and 1b) and common (aberrant) Pathological (see FIGS. 1d and 1e) shape/pattern. In connection with the EEG signals, a known algorithm and model are utilized. The algorithm is the HMM, the parameters of which are continuously updated in order to allow the system to converge to the inherent sleep patterns of a patient, the sleeping behavior of which is to be analyzed. The model is the R&K model, and it provides a clinician a clinical-based set of rules that allow the clinician to distinguish between different sleep stages. According to the present invention, the clinical-based set of rules have been translated into mathematical algorithm, for allowing a fully-automated and accuracy-enhanced analysis of sleep stages and sleeping disorders. In connection with the Respiratory signals, the present invention utilizes Fuzzy Logic Decision Algorithm (FLDA), for obtaining more realistic decisions regarding the feasibility of Respiratory disorders.

The present invention is further characterized by utilizing only one (novel) EEG electrode, instead of four EEG electrodes, as in conventional systems, said novel EEG electrode being attached to a patient in a location that allows, in conjunction with the novel algorithms, to obtain the correct sleep patterns.

The system is designed to measure biological signals of a patient that could be located essentially anywhere, including at his home. Accordingly, data representative of the physiological signals of the patient may be sent in real-time through a data network, such as the Internet, Local Area Network (LAN) or by utilizing a telephone, to a laboratory server, in which the data is processed and analyzed, and the resulting data could be transmitted to a Web server, for introducing the complete, or selections of, said data, to a clinician according to his preferration.

The disclosed system includes a hardware part, for acquiring the required physiological signals, and a software part, for processing and analyzing said signals.

The hardware comprises at least:

(a) ECG electrode strip, for acquiring data related to the condition of the examined heart;

(b) forehead EEG electrode stripe, for acquiring data related to the sleep stages of the examined patient;

(c) chest and abdomen respiratory belts, for acquiring data related to the respiratory status of the examined patient;

(d) oximeter, for measuring the Oxygen saturation level in the patient's blood; and (e) movement detector being placed on limb of a person, or elsewhere.

The software handles the following aspects:

1) ElectroCardiogram (ECG)

According to the present invention, whenever a person is connected to the system, the system adapts itself to the connected person by performing the following:

(a) detecting essentially every signal, that has at least a minimum resemblance to a heartbeat-like shape (i.e., a viable heartbeat), that is contained within the first monitored ECG segment (i.e., portion), the duration of which is predetermined by the clinician, and may be varied by him according to the circumstances (e.g., whenever the shape of the heartbeats of the monitored person are problematic), by comparing the signal to a reference 'Template No. 1', which is initialized with a universal reference shape (hereinafter referred to as the 'Universal HeartBeat'—UHB, see FIG. 1a), which was obtained by averaging several normal-shaped heartbeats of several persons;

(b) employing a predetermined criteria for averaging the viable heartbeats detected by use of the UHB, for obtaining an average heartbeat shape that is unique to the monitored person (hereinafter referred to as the 'Patient-Specific Universal HeartBeat'—PSUHB, see FIG. 1b). Template No. 1 is assigned the characteristics of PSUHB in order to utilize it as the unique reference of the person being monitored;

(c) comparing additional heartbeat-like signals, in corresponding additional portions of the ECG signal, to the PSUHB reference;

(d) whenever a new viable heartbeat is detected by using the updated Template No. 1 (i.e., PSUHB), storing it and analyzing its medical implications;

(e) updating Template No. 1 (i.e., PSUHB), according to a predetermined criteria, by utilizing additional new viable heartbeats for re-averaging the monitored person's unique viable heartbeats, according to predetermined criteria, for allowing the system to enhance its adaptation to the monitored person; and (f) repeating c) to e).

Viable Heartbeats

Prior to employing Template No. 1 on a Beat Under Test (BUT), the system first identifies the relative time-wise location of the BUT within the continuous ECG signal.

The BUTs are identified by manipulating several signals associated with the corresponding output channels of the WTA. The number of the channels depends on the frequency at which the ECG signal was originally sampled. In a first WTA output signal (commonly referred to as the 'high scale'), the high frequency content of the ECG signal is emphasized (see FIG. 8a). The lower the 'scale', the lower the dominant frequency of the ECG signal that is emphasized (see FIGS. 8b and 8c).

According to the present invention, the absolute values of the first three 'scales' (FIGS. 8a, 8b and 8c) are 'summed-up', resulting in a signal (FIG. 8d) having a high peak, which allows an easy detection of 'R-peak' of every heartbeat. Due to the latter manipulation, the 'R-peak' of a heartbeat will always be the most perceptible point in the heartbeat, and, therefore, will be easily detected and will essentially eliminate the risk of misdetection of R-peaks (i.e., due to noises, movements, T waves and other types of interference).

As shown in FIG. 8d, there are two points that have a larger energy, i.e., the heartbeats marked as 'AR'. Nevertheless, the lower-energy R-heartbeats are viable heartbeats and will be analyzed accordingly. From the signal depicted in FIG. 8d, the R-peaks are "placed" in the filtered ECG signal, as shown in FIG. 8e.

The identified R-peaks, as well as the AR-peaks, are utilized as timing indications, around which the samples (of the ECG signal) are evaluated for determining the duration and relative location of each (required) segment (i.e., PQ, QR, RS, QRS and ST). Accordingly, essentially each BUT is identified by the system, after which it is characterized (i.e., its type being determined).

Each AMF outputs a probability value (between 0.0 to 1.0), indicating the resemblance between the BUT to the corresponding template. The larger this value, the more the BUT resembles to the corresponding template. The corresponding AMF outputs a Normalized Correlation (NC) value, which is compared to a first threshold value $NC_{TH1}$. If $NC>NC_{TH1}$, it indicates that a viable heartbeat has been detected, in which case it is further processed.

The PSUHB may be updated, as ECG signal continues to 'feed' the system, according to one of the following principles:

(1) whenever several viable heartbeats are detected within a predetermined time interval, the PSUHB is calculated by averaging only the viable heartbeats detected in the last ECG segment; or (2) as in (1), only that the PSUHB is calculated by averaging the viable heartbeats detected in every ECG segment; or (3) whenever predetermined number 'n' of viable heartbeats are detected, the PSUHB is calculated by averaging only the last 'n' viable heartbeats that were detected; or (4) as in (3), only that the PSUHB is calculated by averaging all of the detected viable heartbeats; or (5) whenever a new viable heartbeats is detected, the PSUHB is calculated by averaging all of the viable heartbeats; or (6) whenever a predetermined time-interval elapses.

Whenever a new PSUHB is calculated, it is used as a new reference template for allowing the system to identify new viable heartbeats in future ECG segments of same monitored person. As ECG signal continues to be input into the system, the system converges from the generalized universal (mean) heartbeat patterns into the specific patient's heartbeat patterns (i.e., the system 'familiarizes' itself with, or 'learns', the inherent cardiac condition of the currently monitored patient). The latter process is employed on Normal heartbeat, as well as on Pathological heartbeat, and it allows the TMP to determine accurately the cardiac status of the examined person. If the examined (current) heartbeat is identified as pathological, a second classification process is employed, for determining the exact type of the pathology, after which the current identified pathological type is utilized for calculating a new mean pattern that is essentially more accurate than the previous calculated mean pattern.

At the time a (new) person is connected to the system, the system does not have any patient-related data, and therefore it must utilize a relatively 'weak' criteria to start identifying the first person's BUTs. Therefore, the system utilizes the UHB, which is associated with a relatively low threshold value $NC_{TH1}$. However, after the first PSUHB is calculated, i.e., after the first ECG segment provides the system with some unique patient-related data (i.e., data that reflects the inherent cardiac condition of the person currently being monitored), a 'harsher' criteria is employed by the AMF, by utilizing a second threshold value $NC_{TH2}$ (i.e., $NC_{TH2} > NC_{TH1}$).

Whenever a viable heartbeat is detected, which is not pathological heartbeat, the system considers it as Normal heartbeat. Each Normal heartbeat is segmented into four clinically important segments: QRS, ST, PR and QT. The segmentation process is based on the prior knowledge of the relative location of the R-wave, T-wave and P-wave of each normal heartbeat, which were found by employing the WTA at an earlier stage, as described before.

Accordingly, the system finds the corresponding segments boundaries by:

(1) Finding the peak of the Q-wave;

(2) Finding the onset of the Q-wave;

(3) Finding the peak of the S-wave;

(4) Finding the end of the S-wave;

(5) Finding the peak of the T-wave;

(6) Finding the onset of the T-wave;

(7) Finding the end of the T-wave;

(8) Finding the onset of the P-wave;

The system automatically searches for the above-specified boundaries while synchronized with the R—R interval, which was accurately found by the WTA in an earlier stage of the analysis. Accordingly, the system provides a person-adaptive and heartbeat rate adaptive segmentation process.

T-Wave Detection

The major problem in the segmentation process is to precisely characterize the T-wave, i.e., to precisely detect its shape and phase, which are critical for a precise determination of the ST segment and the QT interval. According to the invention, the T-wave of a heartbeat is characterized, i.e., a decision is automatically made, regarding whether the T-wave is 'normal, 'upside-down' or 'bipolar'. The T-wave characteristics are found by identifying its onset and endpoint.

ST Analysis

One of the clinically most important parameter associated with cardiac condition, is the ST depression/elevation, as this parameter may indicate a symptom for heart attack. In order for the system to evaluate the ST segment, it selects a portion of the ECG, which is contained within the isoelectric interval (the isoelectric interval is defined as the time between the end of the former T wave and the onset of the current P wave), which is located between two consecutive heartbeats. Then, the system 'extracts' 0.1 Second of this interval, which is utilized as a reference segment, to which the ST segment is compared. An absolute margin is calculated between the mean magnitude of the ST segment and the mean magnitude of the reference segment. ST depression/elevation is identified if the absolute margin is larger than a threshold value.

QT Analysis

The duration of the QT interval is calculated, as well as the variability of said duration and the corresponding spectrum, by utilizing models known as the 'AR-models'.

Sometimes, the 'normal' heartbeat of a person does not include a perceptible R-wave (i.e., which the system can not identify or detect). Therefore, the system is configured to search for P-waves in these heartbeats, measure the QRS duration and check if the heartbeat is not premature. If these conditions meet certain criteria, the system considers the corresponding heartbeats as viable heartbeats, and the AMF's template is updated accordingly and automatically by the system.

The system also calculates Heart Rate (HR) and Heart Rate Variability (HRV) parameters, which are easily derived from the ECG signal by employing techniques that are well known to skilled in the art. Calculation of HR and HRV is implemented by utilizing only Normal heartbeats.

The system is capable of detecting HR abnormalities from different physiological signals such as those derived from the signals associated with a heart condition, the patient movement activity, sleep stage, etc., by utilizing an automatic physiological events detection and a set of fuzzy rules.

Pathological Heartbeats

Whenever a viable heartbeat is detected (i.e., by use of Template No. 1), the system compares it to two commonly (universally) known aberrant heartbeats (i.e., PVC1 and PVC2), by which Templates No. 2 and 3 are initially assigned:

Template No. 2—Universal Pathological HeartBeat No. 1 (UPHB1) template. This template is initialized by the shape of the PVC1, which represents essentially any signal pattern that resembles a first commonly known aberrant heartbeat (i.e., PVC1, see FIG. 1d), and was obtained by averaging several aberrant heartbeats from several persons (having the same pattern as the first known aberrant pattern); and Template No. 3—Universal Pathological HeartBeat No. 2 (UPHB2) template. This template is initialized by the shape of the PVC2, which represents essentially any signal pattern that resembles a second commonly known aberrant heartbeat (i.e., PVC2, see FIG. 1e), and was obtained by averaging several aberrant heartbeats from several persons (having essentially the same pattern as the second known aberrant pattern).

Employing these two templates results in two Normalized Correlation values (i.e., $NC_{P1}$ and $NC_{P2}$, respectively). Normally, $NC_{P1} \neq NC_{P2}$. Therefore, the system selects the UPHBi (i=1 or 2) that yields the maximal NC (i.e., between $NC_{P1}$ and $NC_{P2}$), and compares its NC to a third threshold value (i.e., $NC_{TH3}$). If the condition $NC > NC_{TH3}$ is met, the system decides that the viable heartbeat has the corresponding aberrant pattern type (i.e., UPHB1 or UPHB2). Otherwise, a further analysis is carried out, for identifying the presence of noise or movement artifacts. The noise and movement artifact detection is based on a specific patient movement learning algorithm and environmental noise elimination algorithm. If no noise or artifacts are detected in the heartbeat, it is compared to a forth threshold value $NC_{TH4}$, which is selected so that $NC_{TH4} < NC_{TH3}$, for essentially eliminating the risk of midetection of aberrant heartbeats. If $NC < NC_{TH4}$, it indicates that the heartbeat is so deformed or corrupted that its shape is unknown.

After detecting several aberrant heartbeats, the system may learn the patient-specific aberrant heartbeat patterns and introduce to a clinician a corresponding sequence of pathological heartbeats.

If the system decides that the viable heartbeat essentially matches the UPHB1 template, or the UPHB2 template, it stores it for calculating new corresponding templates (i.e., PSUPHB1 and PSUPHB2, respectively), which reflect the corresponding patient-specific aberrant heartbeat. Calculating PSUPHB1 and PSUPHB2 is implemented according to the same principles described in connection with the PSUHB.

Pathological Sequences

After a viable heartbeat is identified as aberrant heartbeat, it is stored, and a corresponding sequence of pathological heartbeats is established therefrom. There are several commonly known pathological sequences ('A' and 'N' indicate 'Aberrant' and 'Normal' heartbeats, respectively):

(1) VT—A, A, A, A, A, . . . , (generally seen in a tachycardia-type disorder associated with the ventricles). VT is detected by finding a sequence of pathological heartbeats and instantaneous Heartbeat Rate (HR) that exceeds a clinically predetermined threshold value;

(2) SVT—PAC, PAC, PAC, PAC, . . . , (generally seen in another type of tachycardia disorder); (PAC—Premature Atrial Contraction, as seen in the ECG as a normal heartbeat morphology only if it is premature);

(3) Bigeniny—A, N, A, N, A, N, . . . ,.;

(4) Trigeminy 1—N, N, A, N, N, A, N, N, A, . . . ,.;

(5) Trigeminy 2—A, A, N, A, A, N, A, A, N, . . . ,.;

(6) Tachycardia—accelerated heartbeat rate. Tachycardia is detected by finding several consecutive heartbeats having a rate that is above a certain clinically predetermined threshold value; and (7) Bradycardia—too low heartbeat rate. Bradycardia is detected by finding several consecutive heartbeats having a rate that is below a certain clinically predetermined threshold value.

2) Automatic Sleep Staging (ASS) System

The ASS system is configured to identify the following sleep stages: wakefulness, sleep Stage 1, 2, 3 and 4, and Rapid Eye Movement (REM), which is associated with Dreaming stage. The ASS system is also capable of identifying other special events, such as K-complexes, spindles, alpha intrusions, body and electrode movements, eye blinks, awakenings, arousals and micro-arousals by utilizing only one electrode.

The ASS system performs, in general, two analyzing processes. The first process is associated with 'on-line' (i.e., 'real-time') process. Execution of this process involves real-time extraction of several features and evaluation of the features every predetermined time interval (e.g., every 30 seconds), in order to reach a decision regarding the current sleep stage. The second analyzing process, being an 'off-line' process, is employed (normally) after several hours of sleeping, for allowing the ASS system to converge to (i.e., 'learn') the inherent sleep behavior of the monitored person.

The first (i.e., 'on-line') analyzing processes involves the following:

(1) Filtering the EEG signal, EOG and the EMG signals;

(2) Adaptively segmenting the resulting filtered EEG and EOG signals into QSSs;

(3) Extracting the required features from the resulting quasi-stationary EEG, EOG and EMG segments;

(4) Preliminary classification of each EEG QSS.

(5) Whenever relevant, detecting special temporal events contained within the EEG QSS;

(6) Special events classification, by using environment characteristics;

(7) If an EOG signal exists, detection of EOG REM, by employing related algorithm;

(8) Real-Time determination of sleep stages;

(9) Real-Time determination of awakening, arousals and microarousals; and

(10) Repeating (1) to (9).

The second analyzing processes involves the following:

(11) Initial division of the frequency groups into sub-groups;

(12) Employment of Baum-Welch on the HMM model;

(13) Refining the special event classification of (6) in the first analyzing processes.

(14) EMG energy 'lows' (i.e., minimal points) detection algorithm using hierarchical fuzzy clustering algorithm;

(15) Refining sleep staging process; and

(16) Refining awakening, arousals and micro arousals detection.

(1) Filtering

The raw EEG signal is filtered by two types of (digital) Band-Pass Filter (BPF), which are implemented by DSP technique commonly known as 'Finite Impulse Response' (FIR). The first FIR-based BPF (1-35 Hz) cancels drifts in the baseline of the raw EEG signal and acquires the desired EEG bandwidth. The resulting signal is hereinafter referred to as the 'filtered EEG'). The second FIR-based BPF (20-35 Hz) acquires the EMG signal (the tonus muscle is very close to the Fp electrode). The filtered EEG is decomposed into two signals by utilizing a third and a fourth FIR-based BPFs. The third and fourth BPFs are referred to as the 'Slow Frequency EEG' (SFEEG) and the 'Fast Frequency EEG' (FFEEG), respectively. If the EOG and EMG signals also exist, the corresponding drift in the EEG signal is canceled by employing corresponding BPF(s).

(2) Adaptive Segmentation

EEG signal is a non-stationary process, namely, its statistical characteristics, such as frequency and moments, are time-dependent. In order to obtain a reliable identification of sleep stages of a monitored person, a first step is implemented, in which the EEG signal is partitioned into QSSs using an adaptive segmentation algorithm, hereinafter referred to as the 'Adaptive Segmentation Algorithm for EEG signals' (ASAEEG).

The ASAEEG algorithm utilizes the known (i.e., to those skilled in the art) Generalized Likelihood Ratio (GLR) measure, for distinguishing between statistically QSSs. For example, given two time series, the GLR measure compares the statistical properties of the two series and outputs a value, which represents the statistical difference (or 'distance') between the two series. For example, a zero value means that the two series have exactly the same statistical properties, a fact which leads to the conclusion that the two series belong to the same statistical process.

The ASAEEG algorithm is characterized by its capability to dynamically change a 'time-window' (hereinafter referred to as the 'Growing Reference Window'—GRW), within which a corresponding portion of the EEG signal is analyzed. A signal, which is contained within said portion, usually comprises a dominant wave (i.e., which characterizes said portion) and several frequency components that are associated with other waves and superimposed on said dominant wave.

The GRW changes automatically in duration, as well as in its relative location, until an optimized decision with respect to specific examined EEG portion, is obtained by utilizing the GLR measure.

The probability values of the five waves form a vector, which characterizes the current (stationary) segment being analyzed. As additional consecutive segments undergo the same process, additional corresponding vectors are formed. Every vector is included in a matrix, which characterizes the sleep status of the monitored person. The system may automatically update the matrix (i.e., by adding additional vectors) according to some criteria. For example, the matrix may be updated per time-interval. The larger the matrix, the more the system is adapted to the inherent patient's specific sleep behavior, resulting in more enhanced accuracy of the corresponding decisions made by the system.

(3) Features Extraction

Identifying Features in a Quasi-Stationary Segment

An EEG signal normally comprises five major types of signals (generally referred to as waves): (1) $\delta$-wave (1.0-3.5 Hz), (2) $\Theta$-wave (4.0-7.0 Hz), (3) $\alpha$-wave (7.5-12 Hz), (4) $\sigma$-wave (12-15 Hz); and (5) $\beta$-wave (15-35 Hz).

For each QSS that is identified, several, or all, of the following features associated with are obtained:

1) Relative energy in the $\delta$-wave Band;

2) Relative energy in the $\Theta$-wave Band;

3) Relative energy in the $\alpha$-wave Band;

4) Relative energy in the $\sigma$-wave Band; and

5) Relative energy in the $\beta$-wave Band;

6) Statistical data, such as 'Mean value', 'Variance' and 'Skewness';

7) Duration of the QSS;

8) Fundamental frequency of the QSS.

Data related to features Nos. 1) to 8) are obtained in connection with the filtered EEG, as well as the EMG signals, while features Nos. 1) and 2) are obtained in connection with the EOG signal.

(4) Preliminary Classification of each EEG Quasi-Stationary Segment.

After a QSS is characterized (i.e., according to (3)), it is associated with one of the three frequency groups (i.e., HFG, MFG or LFG), thereby creating three corresponding clusters, by employing fuzzy logic rules on the extracted features.

A real-time decision, regarding a current sleep stage, is based on evaluating several consecutive QSSs. Therefore, the system automatically makes sleep stage evaluations after each predetermined time-interval, in which several QSSs are contained. For example, a time interval of 30 seconds has been found to be wide enough for containing several QSSs, while still sustaining the 'real-time' attribute of the system.

(5) Detecting Special Temporal Events Contained within the EEG Quasi-Stationary Segment.

The special events 'K'-complexes, body and electrode movements, rapid eye movements and eye blinks are temporal events, and are detected by exploiting the fact that they differ from the ongoing EEG signal by their energy, skewness, duration and fundamental frequency.

(6) Special Events Classification.

Because there is a strong correlation between special events and their adjacent signals, an 'environment enrichment' principle is employed, namely, each special event is classified after characterizing the frequency content of the corresponding adjacent QSSs, and based on its temporal morphology. For example, if a special event is detected, which has a distinguishable temporal morphology, and its adjacent QSSs belong to the MFG, it is most probable that this event is a 'K-complex'.

After the time-wise (temporal) events are identified, they are essentially removed from the ongoing EEG signal for allowing the system to analyze its corresponding spectral features (i.e., the relative energies of the $\delta$, $\Theta$, $\alpha$ and the $\beta$ waves) by utilizing the HMM models.

(7) Detection of EOG REM

REM signals are associated with dreaming stages, and are detected by exploiting the fact that REM are paradoxical and have higher energy regarding their environment.

(8) Real-Time Sleep Staging

Detecting Changes from One Frequency Group to Another

The ongoing EEG signal is substantially a Markovian process, namely; the current status of a sleeping person largely depends on its past behavior, a fact which allows employing the Hidden Model (HMM) statistics model on the ongoing EEG signal.

In order to simplify the problem of identifying changes between the three frequency groups (i.e., HFG, MFG and LFG) a 'Three-States' model (TSM) is utilized, which is based on the assumption that there are three major frequency activities (or 'states') involved in a sleeping person. There are various probability values associated with passing from one frequency group (e.g., HFG) to another frequency group (e.g., LFA). The task of the system is to reach a decision regarding the current stage, by evaluating the (known) predecessor stages and by utilizing statistics-based estimation process.

Accordingly, the above-mentioned five sleep waves have been grouped into three frequency groups (stages). Each frequency group corresponds to a different sleep stage (i.e., light sleep, dreaming and awakening). The decision-making process, regarding the sleep stages, is based on the HMM model.

Each stage is characterized by a 4-dimensional (probability) gaussian. Accordingly, a two-dimensional probability graph is formed, in which the 'X' axis is the probability that the current segment is the $\alpha$-wave, and the 'Y' axis is the probability that current segment is the $\delta$-wave. The system initializes the probability graph with three 'global' mean 'starting-points', each of which represents a different frequency group. The global starting-points are obtained by averaging EEG starting points of several persons. Alternatively, individual global starting-points are calculated, by employing a fuzzy clustering algorithm on the pre-determined frequency groups.

Sleep Staging

The final decision, regarding the relative time-wise location and duration of the sleep stages, is obtained by implementing the following:

1) Averaging each one of the three clusters, i.e., the QSSs that were found in the last 30-seconds time-interval, that are associated with the same frequency group; and 2) Employing a set of R&K rules on the averaged clusters and on the temporal events.

(9) Awakenings, Arousals and Micro-Arousals Detection.

A fuzzy logic algorithm, based on the rules for arousal detection, is used, in order to automatically detect awakenings, arousals and micro-arousals.

(10) Repeating (1) to (9) for Each New 30-Seconds Time-Interval.

(11) Initial Division of the Frequency Groups into Subgroups.

Since each person has essentially different sleep patterns, which are uniquely represented by corresponding signals, it is allowed to characterize the person's sleep behavior more accurately, by dividing the frequency groups into subgroups according to unique physiological properties/criteria that characterize the corresponding frequency group. For example, the HFG is divided into two subgroups—a first subgroup is characterized by having increased α-wave activity, and a second subgroup is characterized by having increased β-wave activity. Likewise, the MFG is divided into three subgroups. The LFG remains as one group.

(12) Employment of Baum-Welch on the HMM Model.

A Gaussian Probability Function (GPF) is employed in connection with each of the (frequency) subgroups. Each 'gaussian' is characterized by two parameters, namely, its 'center' (i.e., the 1.0 probability) point and variance, and represents the probability of a given quasi-stationary segment to belong to the corresponding subgroup.

The Baum-Welch algorithm is implemented in the second analyzing process (i.e., in the 'off-line' process), and its task is to update the gaussian functions. The Baum-Welch algorithm is employed every several hours (i.e., of sleeping) on the last known GPFs and the HMM model, in order to update the GPFs. The more times the Baum-Welch algorithm is employed, the more accurately the ASS system converges to the inherent (unique) sleep patterns of the monitored person.

(13) Refining Special Events Classification.

Since the 'real-time' decisions are based on a global GPF (i.e., without considering 'learning' process), these decisions might be inaccurate. However, the updated GPFs (i.e., person's specific GPFs) allow the ASS to reprocess (i.e., 'refine') the data on which the 'real-time' decisions were based, and obtain accurate decisions regarding special events.

In other words, the ASS system adapts itself to the actual three groups of frequencies that uniquely represent the inherent sleeping patterns of the monitored person. Each new detected quasi-stationary segment of the EEG signal contributes to the decision making process, as the accumulated effect of all the quasi-stationary segments allows the system a better 'learning' of the patient.

(14) EMG Energy 'Lows' (i.e., Minimal Energy Points) Detection Algorithm.

EMG energy 'lows' are detected by using hierarchical fuzzy clustering algorithm which recursively partitions the low EMG energy group into a low energy group and a high one, until stopping condition is fulfilled.

(15) Refining Sleep Stages Classification.

Refining sleep stages classification is carried out essentially the same way as the special events classification (see (13)).

(16) Refining Arousal Detection.

Arousal detection is carried out essentially the same way as the special events classification (see (13)).

3) Respiratory

A probability-based decision, associating Respiratory disorder with an apnea (or hypoapnea), is made by the system after it considers data from five data sources/channels: (1) EMG, (2) Limb movement, (3) Chest effort, (4) Abdominal effort and (5) Blood saturation. In order to simplify the decision-making process, the five data sources/channels have been grouped into three groups: (1) Effort, which includes the Chest Effort signal and the Abdominal Effort signal, (2) Movement, which includes the EMG signal and the Limb Movement signal and (3) Oxygen Saturation, which is measure by utilizing an Oximeter. Corresponding algorithms have been developed for extracting relevant features from each of the above-described groups.

A normal breathing signal is characterized by having a low frequency signal, the frequency and magnitude of which are essentially constant. In this case, the envelope of this signal does not change with respect to time. An hypoapnea is clinically defined as having the respiratory airflow decreasing by at least 20% from its initial value, for duration of at least 10 Seconds (Amy L. Meoli et al. "Hypopnea in Sleep-Disordered Breathing in Adults" Sleep, vol 24 No. 4, 2001). Accordingly, in order to decide whether a Respiratory disorder is an hypoapnea (or an apnea, which is clinically more severe, but easier to identify), the envelope of the effort signal is first analyzed, by carrying out the following:

(1) Detection and Smoothing of the Envelope (DSE) of the effort signal. In order to produce the required envelope, the amplitude of each breathing cycle is identified, and the shape of the envelope of the breathing signal is 'smoothed' by utilizing a set of fuzzy logic rules, in order to remove irrelevant maximum points.

(2) Peak Detection and Maximum Setting (PDMS) of the envelope signal. After establishing the corresponding envelope signal, its maximal points are identified and utilized as time-wise boundaries for segmenting the effort signal into corresponding segments. If there is a group of at least two maximal points (i.e., in the envelope), which are too close (i.e., with respect to time) to one another, only the larger maximal point in that group is selected as time boundary. The identified time boundaries are also utilized for segmenting the envelope into segments that overlap the corresponding effort signal segments.

(3) Segment Evaluation Process (SEP). Each segment (i.e., in the effort signal) is evaluated for determining whether there is more than 20% decrease in the magnitude of the effort signal contained within said segment. If there is a 20% decrease in said magnitude (i.e., for a duration larger than 10 seconds), a Fuzzy Logic Algorithm (FLA) is employed, for evaluating other relevant events, such as Oxygen de-saturation, arousal(s), movement(s).

However, if a decrease less than 20% is not evident in said magnitude, it is necessary to determine the 'direction' of the envelope of the evaluated segment, i.e., whether it tends Upwards (i.e., its time derivative is positive in each point of the corresponding envelope), Downwards (i.e., the envelope has negative time-derivative) or it maintains essentially the same magnitude. In order to determine the direction of each envelope's segment, a mathematical approximation to the envelope's segment is made, by utilizing a polynomial of second order (parabola). Then, mathematical manipulations are carried out for identifying the required corresponding time-derivatives of the corresponding parabola. Each envelope segment, which does not meet the '20% magnitude decrease' criteria, is assigned a corresponding parabola.

A Segment Combining Algorithm (SCA) is employed on segments that do not comply with the 20% of the EPA criteria (see par. 2), in order to adjoin two adjacent segments to one (grand) segment. The SCA could be the Viterbi Algorithm—which will not be discussed, since it is known to those skilled in the art (Reference could be made to the web site—http:/www.comp.leeds.ac.uk/scs-only/teaching-materials/http://www.comp.leeds.ac.uk/scs-only/teaching-materialsHidden-MarkovModels/html_dev/viterbi_algorithm/s1_pg3.html).

(4) Decision Making Algorithm (DMA). According to the present invention, the Respiratory system is characterized by employing a Fuzzy Logic for allowing the system to reach more realistic decisions regarding the nature of the Respiratory disorders. Accordingly, the DMA is based on a Fuzzy Logic Algorithm (FLA), which is utilized for estimating the probability of a Respiratory disorder being an apnea, or hypoapnea, while taking into account data from the above-described data sources/channels. The FLA gives mathematical interpretation to known clinical set of rules (according to which apnea is detected), and, thereby, allows the system to mimic the analysis process that is currently made manually by a clinician.

The FLA utilizes several trapezoid-shaped 'Probability-Wise Windows' (PWWs). Each PWW is associated with a corresponding event that is encountered in the corresponding data source selected from the group of data sources (1), (3), (4) and (5), which are described hereinabove. The term 'event' refers to noticeable change that is detected in the corresponding signal, such as sudden movements and/or exerted efforts. For example, in connection with the first data source, i.e., "(1) EMG", an event means that a rise in the EMG level has probably been detected. Each PWW has a duration that is relatively much larger (i.e., wider) than the duration of the corresponding event. In addition, each PWW comprises a positive slope portion (representing a gradual increase from 0.0 to 1.0 probability value), a 1.0 probability value portion and a negative slope portion (representing a gradual decrease from 1.0 back to 0.0 probability value).

The time duration of each part in each PWW has been optimized according to medical criteria, as well as its relative location (i.e., time-wise synchronization) of each PWW. For example, if the monitored person starts suffocating (i.e., the magnitude of the effort signal decreases by more than 20%), a corresponding delayed decrease in the Oxygen saturation level in the person's blood is expected to be observed. A normal delay (i.e., between suffocation and noticeable decrease in the Oxygen saturation level) is of a couple of seconds (e.g., 4-6 seconds). Accordingly, a first step will take place, according to which an Oxygen-related PWW will 'open' (i.e., placed) in a way that its (vertical) center is aligned with the ending point of the apnea event. Then, a second step will take place, according to which the system analyzes the time location of the Oxygen event in relation to the Oxygen-related window. At the end of the latter analysis, the oxygen is assigned a probability value. For example, in an ideal apnea event, the delay between the Oxygen event and the suspected apnea event matches exactly the clinically predetermined delay, in which case the instant of the Oxygen event matches exactly the time center of the Oxygen-related PWW, in which case the Oxygen event is assigned the probability value 1.0. Accordingly, the probability that the suspected apnea is a 'real' apnea is 1.0. However, the delay may vary from one person to another and from one apnea to another, in which case the corresponding Oxygen event will be assigned a probability value other than 1.0. In some cases, the delay will be such, that the Oxygen event will be timely located outside the Oxygen-related PWW, in which case it will be assigned the probability value 0.0. Accordingly, the suspected apnea will not be regarded as a 'real' apnea (i.e., the essential condition of a following decrease in the Oxygen saturation level—in the expected time window and time location—is not met).

Phase Detection Algorithm (PDA)

A change in the relative phase between the two effort signals (i.e., the chest signal and the abdominal signals) may indicate an obstruction in the upper airways of the monitored person. The PDA performs the following:

a) Generating a signal that represents the phase between the two effort signals.

b) Whenever applicable, finding minima and maxima, the duration of which is more than 10 Seconds.

c) Whenever applicable, finding adjoining events.

Movement Detecting Algorithm (MDA)

A movement is characterized by a noticeable increase in the signal energy. The task of the MDA is to allow distinguishing relatively large movements from the surrounding environment interference. The MDA performs the following:

a) Calculating the energy in overlapping windows with length L.

b) In each segment, finding the points with maximum values.

c) Calculating the normalized distance between each two of the points found in b).

d) Finding the Maximal Normalized Distance (MND) in the normalized distances calculated in c).

Oxygen Saturation Event Algorithm (BSEA)

A blood saturation is defined as an 'event' whenever there is at least 4% decrease from the last steady level. The BSEA performs the following:

a) Smoothing the signal with an averaging window of length L.

b) Finding local minima points in the smoothed signal.

c) Comparing the level of the minimum point to the level of the minimum's base.

d) Classifying events into one of two categories, according to a threshold level being lower than 4%: (1) events in which a magnitude decrease has been detected, which is less than the threshold, and (2) events in which a magnitude decrease has been detected, which is more than the threshold. Events associated with the second category are assigned a higher weight in the final decision making algorithm than the first cathegory's events.

The present invention is directed to a method for measuring a plurality of physiological signals and output a data, being essentially noiseless and artifact-free, the content of which is correlated with corresponding physiological data. The present invention is also directed to a system capable of identifying 'normal' physiological activities of individual patients and adjusting itself according to the identified normal physiological activities. The operation principles of the system may be better understood with reference to the drawings and accompanying description.

Figure 2:
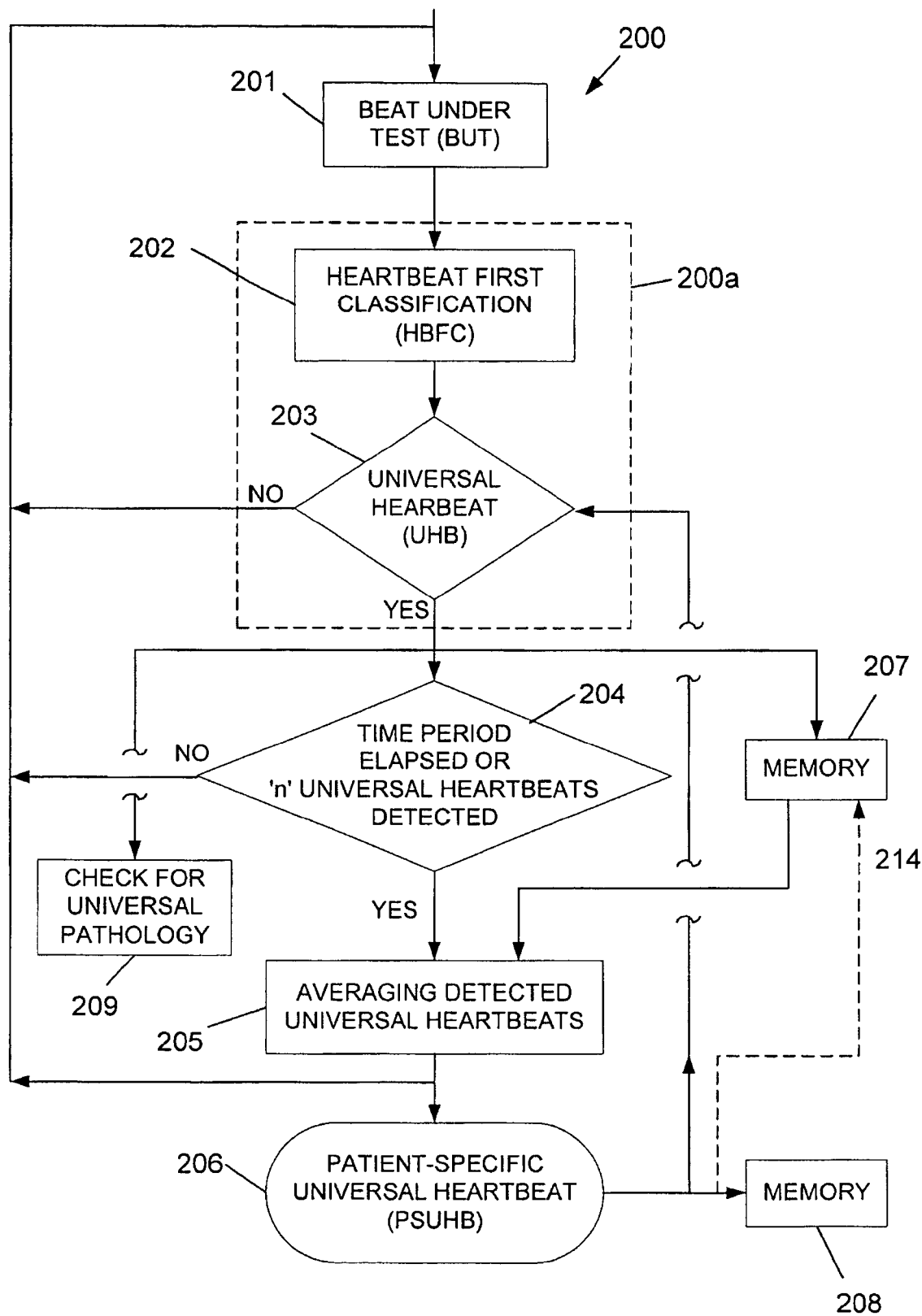
FIG. 2 is a block diagram illustrating the system's adaptation to the Patient-Specific Universal Heartbeat (PSUHB), according to a preferred embodiment of the present invention.

FIG. 2 schematically illustrates the initial identification of signals having essentially a heartbeat-like waveform, according to a preferred embodiment of the present invention. In order to avoid wasting processing time on signals that do not resemble heartbeats, a first classification process is employed (202) on the current Beat Under Test (BUT) 201.

Even though there is a considerable variance involved in signals that represent heartbeats of different persons, these signals are characterized by having typical (noticeable) patterns. An average heartbeat pattern was established by averaging heartbeats of several persons (the 'average heartbeat pattern' is hereinafter referred to as Universal HeartBeat—UHB). Accordingly, the first monitored BUT is compared to the UHB (203) in order to decide whether it is to be considered as a viable heartbeat. The comparison process and resulting decision (200*a*) is implemented by utilizing a digital filter that is commonly referred to as a "Matched Filter", which allows implementation of a "Matched Template"). The Matched Filter (MF) is configured to identify predefined signal pattern (i.e., "template") by employing a corresponding set of parameters. The resulting decision 203 of the MF 200*a* involves a correlation factor, the value of which may be between 0.0 and 1.0. The higher the value of the correlation factor, the more the examined pattern resembles the predefined template of the MF. Since the magnitude of the BUTs may have a significant variance (i.e., due to movements of the sensing electrode, clinical reasons and non-standard amplifiers/equipment), a phenomena that may ill affect the resulting decision, the BUT is Normalized (not shown). MF 200a allows identifying even severely deformed heartbeats (i.e., pathological heartbeats). However, if the current BUT is too corrupted/deformed (i.e., there is very low correlation between the BUT and the MF's template), it is not processed for detecting pathologies. Nevertheless, the corrupted heartbeat may be stored for (whenever required) allowing performing future analysis.

Assuming the system identifies heartbeats that essentially match the UHB (i.e., 'proper heartbeat'), it stores these heartbeats, and, according to a first approach, whenever a predetermined time interval elapses (204), calculates an average pattern (205). The averaged pattern is the 'Patient-Specific UHB' (PSUHB) 206, which is stored in memory 208 (or in memory 207). If the BUT does not match the UHB (203), the system checks the next BUT (201). According to a second approach, the PSUHB is recalculated each time the system identifies new 'n' proper heartbeat (204). Every time a new PSUHB is calculated, it is utilized as a new universal heartbeat reference (203), to which the new BUTs are compared. The PSUHB is constantly updated, providing that new BUTs are sampled, thereby allowing the system to adapt itself to (i.e., learns) the patient's inherent cardiac condition. The learning process allows the system to reach accurate decisions regarding the patient's cardiac condition.

Each time a proper heartbeat is identified, it is stored (207) and analyzed for further classification, e.g., for identifying pathological type (209), if such exists.

Figure 3:
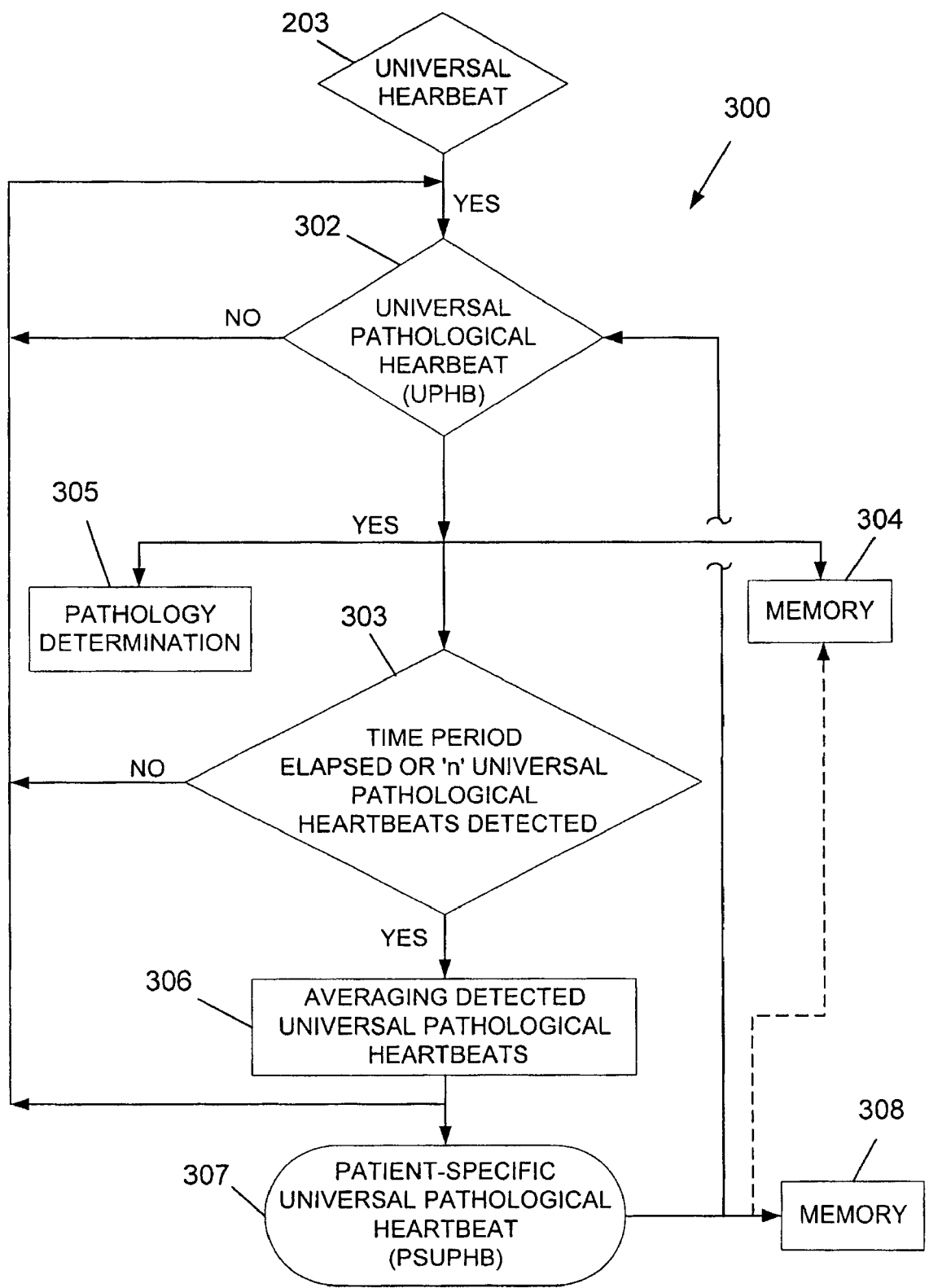
FIG. 3 is a block diagram illustrating the system's adaptation to the Patient-Specific Universal Pathological Heartbeat (PSUPHB), according to a preferred embodiment of the present invention.

FIG. 3 schematically illustrates the initial identification of pathological-like waveforms, according to a preferred embodiment of the present invention. After a BUT is identified as UHB (203), it is compared to Universal Pathological HeartBeat (UPHB) 302. The comparison process in this case is implemented also by utilizing a MF, which has been configured to identify particular pathological patterns.

If a current BUT meets the criteria of UPHB (302), it is further processed in order to determine its exact pathology type (305). In addition, a Patient-Specific Universal Pathological HeartBeat (PSUPHB) (307) may be determined in a way similar to determining PSUHB (206), i.e., 303 and 306 (FIG. 3) are essentially identical to 204 and 205 (FIG. 2), respectively. Each time a PSUPHB (307) is calculated, it is utilized as a new reference pattern (i.e., template) for Matched Filter 302, to which new UHB (203) are compared, until a new PSUPHB is calculated again (307). This way, the system adapt to (i.e., 'learns') the patent's inherent pathological cardiac condition.

Current UPHB (302) and PSUPHB (307) may be stored in memory 304 and/or in memory 308.

Figure 4:
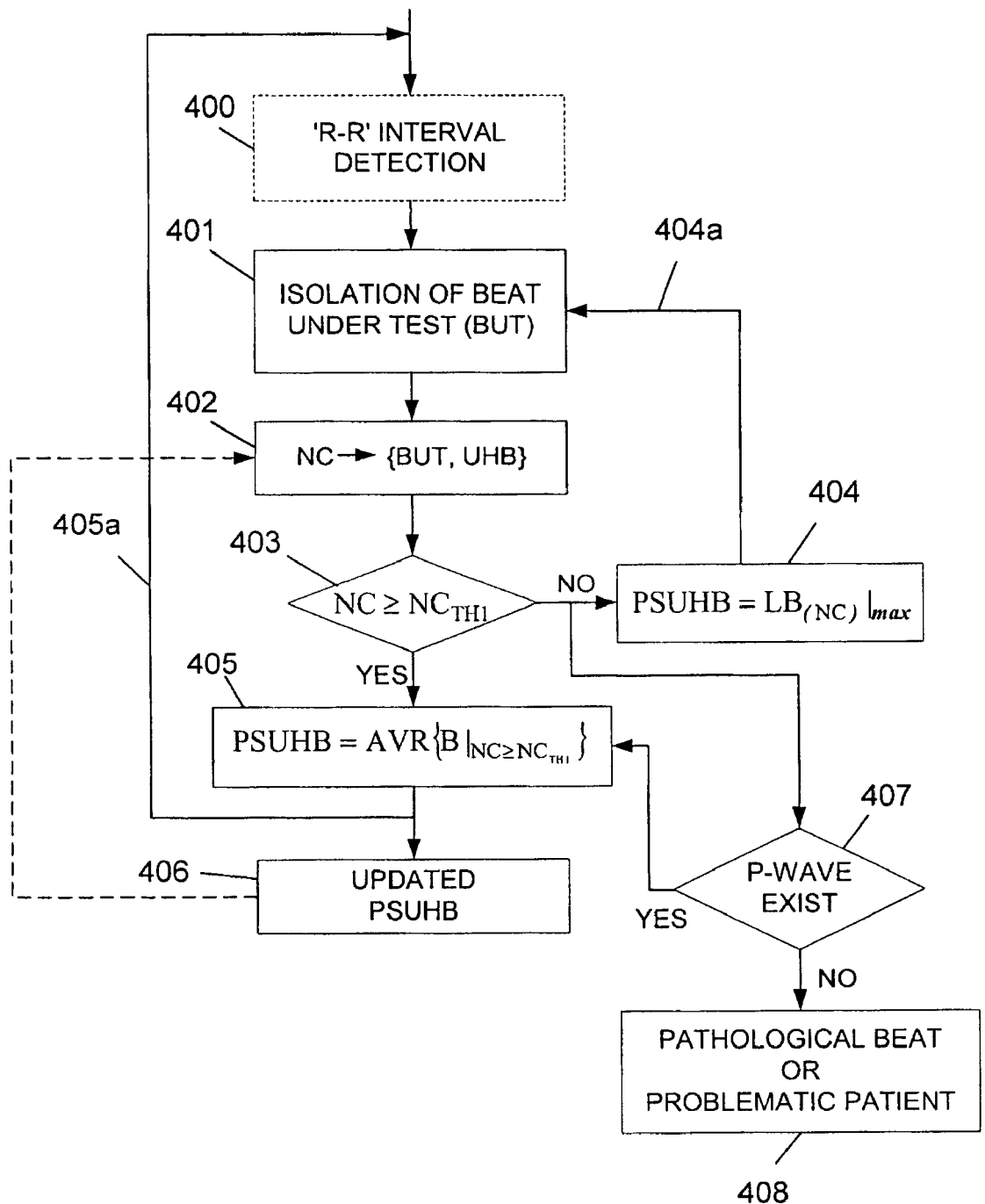
FIG. 4 schematically illustrates a more detailed system's adaptation to the Patient-Specific Universal Heartbeat (PSUHB), according to a preferred embodiment of the present invention.

FIG. 4 schematically illustrates the adaptation principle of the system to the Patient-Specific Universal HeartBeat (PSUHB), according to a preferred embodiment of the present invention. The adaptation process continues as long as new viable heartbeats are identified as having high normalized correlation (NC) value, as described hereinafter.

After detecting the first R—R interval (404), the first BUT is isolated (401). In the first iteration the system correlates the first BUT with the Universal HeartBeat (UHB) stored in the system and a 'Normalized Correlation' (NC) value is calculated (402), i.e., by utilizing a Matched Filter (not shown) in the way described hereinabove. Viable heartbeats having high correlation values are averaged, whether on a time interval basis or viable heartbeats count, and the new PSUHB (405) is utilized as a reference (i.e., MF template) for the next heartbeat(s). Namely, if the condition $NC \geq NC_{TH1}$ (403) is met, wherein $NC_{TH1}$ is a threshold NC (having a typical value of 0.7), a new PSUHB is calculated (405), and the new PSUHB is stored in the storage array (406a) as the new reference pattern/template. Along with storing the (new) PSUHB, the next BUT is isolated (405a) and the process repeats itself. The more viable heartbeats are identified (i.e., having high correlation values), the more accurately the system converges (i.e., adapts) to the specific patient being examined. However, if a second situation occurs, i.e., a patient normally has heartbeats that do not conform to the reference pattern/template stored in the storage array (i.e., the condition indicated 403 is not met for relatively large duration), the last-known viable heartbeat, having the maximum correlation value $(LB(NC)|_{max}.)$, will be regarded as the current PSUHB (404). This way, the system is capable of adapting itself to a patient even in cases in which the patient has abnormal (but non-pathological) viable heartbeat patterns, even though such cases are rare.

If a BUT does not have a P-wave, it is likely to be regarded as aberrant heartbeat. Otherwise, the BUT might be a special 'normal' heartbeat, which characterizes the heart activity of specific person. In the latter case, it is risk that the BUT will not be identified as a viable heartbeat. In order not to allow midsection of such BUTs, the P-wave of the BUTs is searched for (407) and if found, the patient's problematic BUT would be considered as his unique 'viable' heartbeats. If a P-wave is found in the current BUT, the current BUT is utilized for calculating the current PSUHB (405), otherwise, the BUT is regarded as severe pathological heartbeat, or it assumed that the patient is having a critical cardiac condition (408).

In a forth situation (not shown), the heartbeats are very corrupted for a relatively long period. In this case, the system will halt, asking the clinician whether to continue the analysis after selecting heartbeat patterns of the patient as viable heartbeats, or to abort the analysis.

Figure 5:
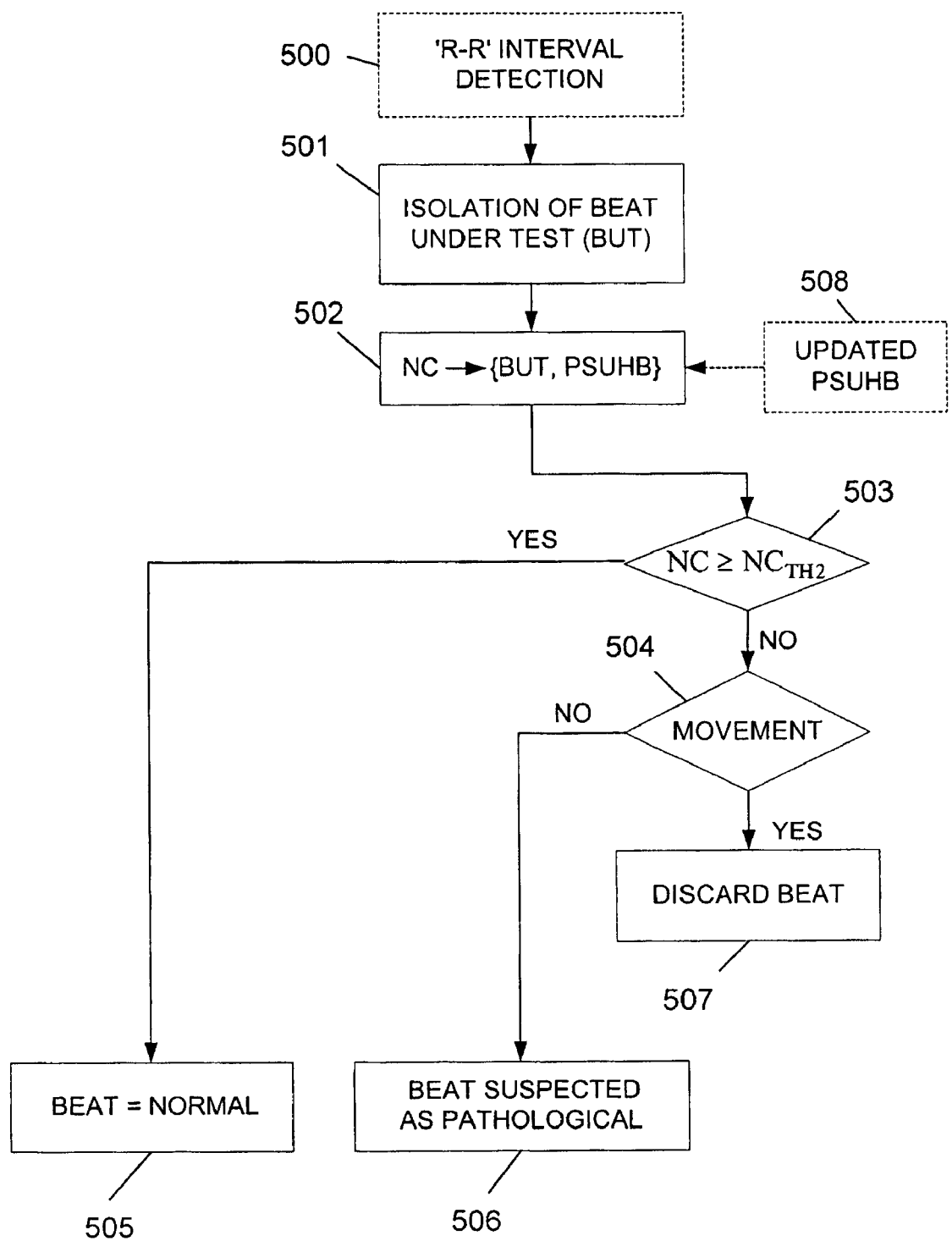
FIG. 5 schematically illustrates the heartbeat classification process, according to the preferred embodiment of the invention.

FIG. 5 schematically illustrates the heartbeat classification process, according to the preferred embodiment of the invention. The function of blocks indicated 500 and 501 is similar to these of blocks indicated 400 and 401 described in connection with FIG. 4. The PSUHB, which is calculated per patient according to the process described in connection with FIG. 4, is utilized as a reference template. The current BUT is correlated with the PSUHB (502) that is stored in a storage array (not shown), and a NC is calculated (502). If the condition $NC \geq NC_{TH2}$ is met (502), wherein $NC_{TH2}$ is a second threshold of NC, the current BUT is considered to be a viable heartbeat. Since at this stage the system is already adapted, at least to some extent, to the patient being monitored (i.e., it utilizes the PSUHB rather than the UHB), the criteria, which is utilized by the system for identifying viable heartbeats may be harsher, namely, $NC_{TH2} > NC_{TH1}$. The latter threshold reflects the large variance, and therefore low correlation value (e.g., 0.7), of heartbeats of different people, and it is required only at the first stage of the analysis, in which the system adapts (i.e., converges) itself to specific patient. After completing the adaptation phase, and due to the relatively small variance (and, therefore, high expected correlation value) of the heartbeats of the same specific patient, the value of the NC could be increased (e.g., to 0.85), for ensuring high precision based decisions regarding the classification of BUTs.

If the condition 503 is not met, i.e., the BUT has small correlation value, the BUT is likely to contain artifacts interference or noise. Therefore, a second decision is made in accordance with movement data (504). If no movement has been detected while sampling the current BUT, this BUT is suspected as pathological heartbeat (506), and the suspected heartbeat undergoes another process (not shown), the function of which is to classify the exact pathology type associated with this BUT. However, if an artifact has been identified, a decision is made (504) that the BUT was sampled under very noisy environment conditions, and it is to be discarded (507).

Figure 6:
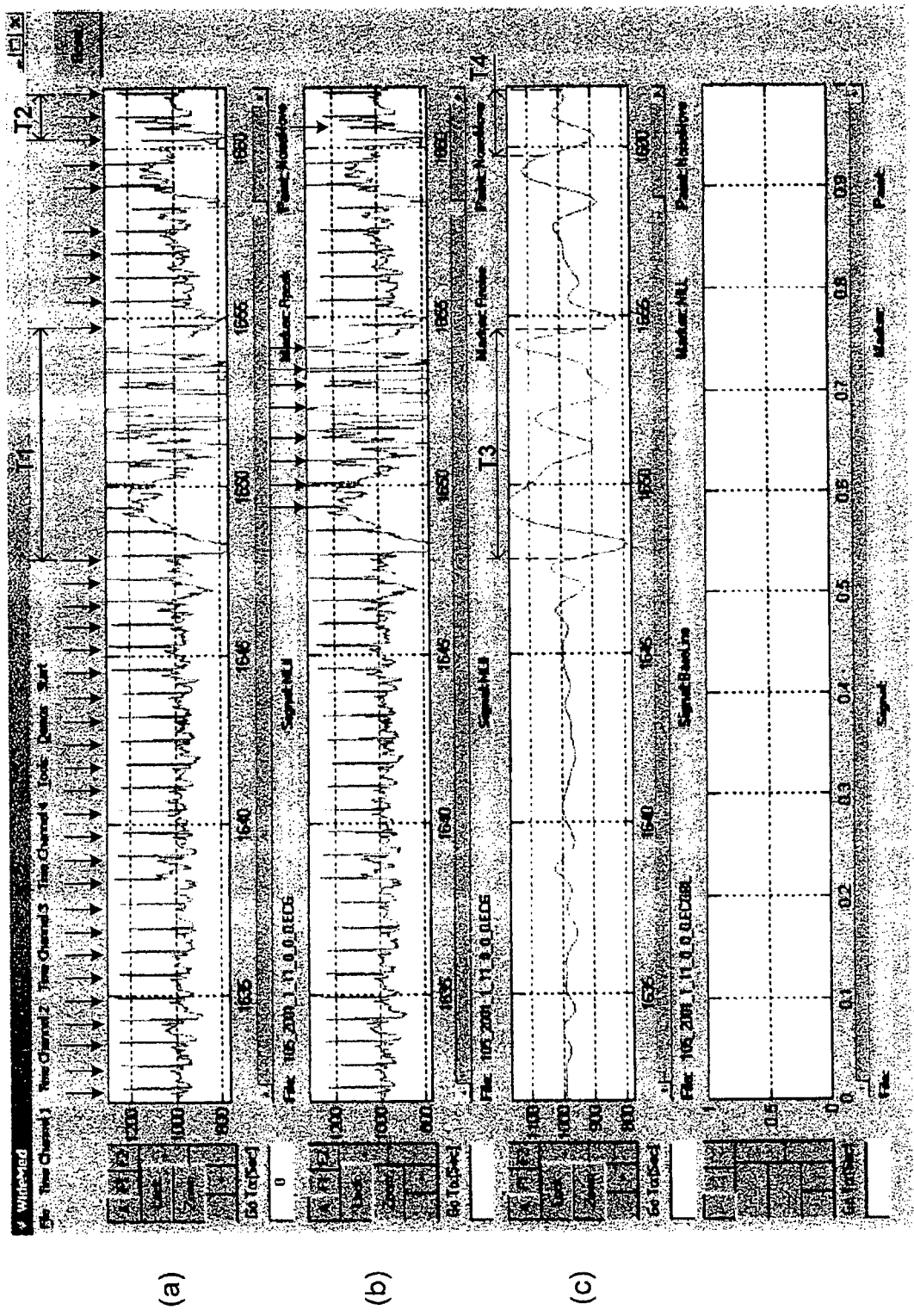
FIG. 6 shows testing results of the first heartbeat classification process according to which viable heartbeats are classified, according to a preferred embodiment of the present invention.

FIG. 6 shows testing results of the first heartbeat classification process according to which viable heartbeats are classified, according to a preferred embodiment of the present invention. The system is capable of distinguishing noisy viable heartbeat from noiseless viable heartbeats. Channel (a) shows the ECG signal, in which the viable heartbeats have been identified and marked by the system (i.e., by corresponding vertical arrows). These viable heartbeats were originally marked by yellow vertical lines (on the computer's screen) and have been replaced by said vertical arrows, for demonstration purpose. In addition, the problematic ECG signal in sections T1 and T2 was originally marked by a conspicuous color in order to attract the clinician's attention. Channel (b) shows the ECG signal, in which the viable noisy heartbeats have been identified and marked by the system (i.e., by corresponding vertical arrows), and channel (c) shows the movement that was detected in time intervals T3 and T4, which essentially overlap time intervals T1 and T2, respectively. As can be seen in FIG. 6, the system is capable of identifying viable heartbeats even in cases in which there are relatively large movements of the patient and/or the sensing electrode.

Figure 7:
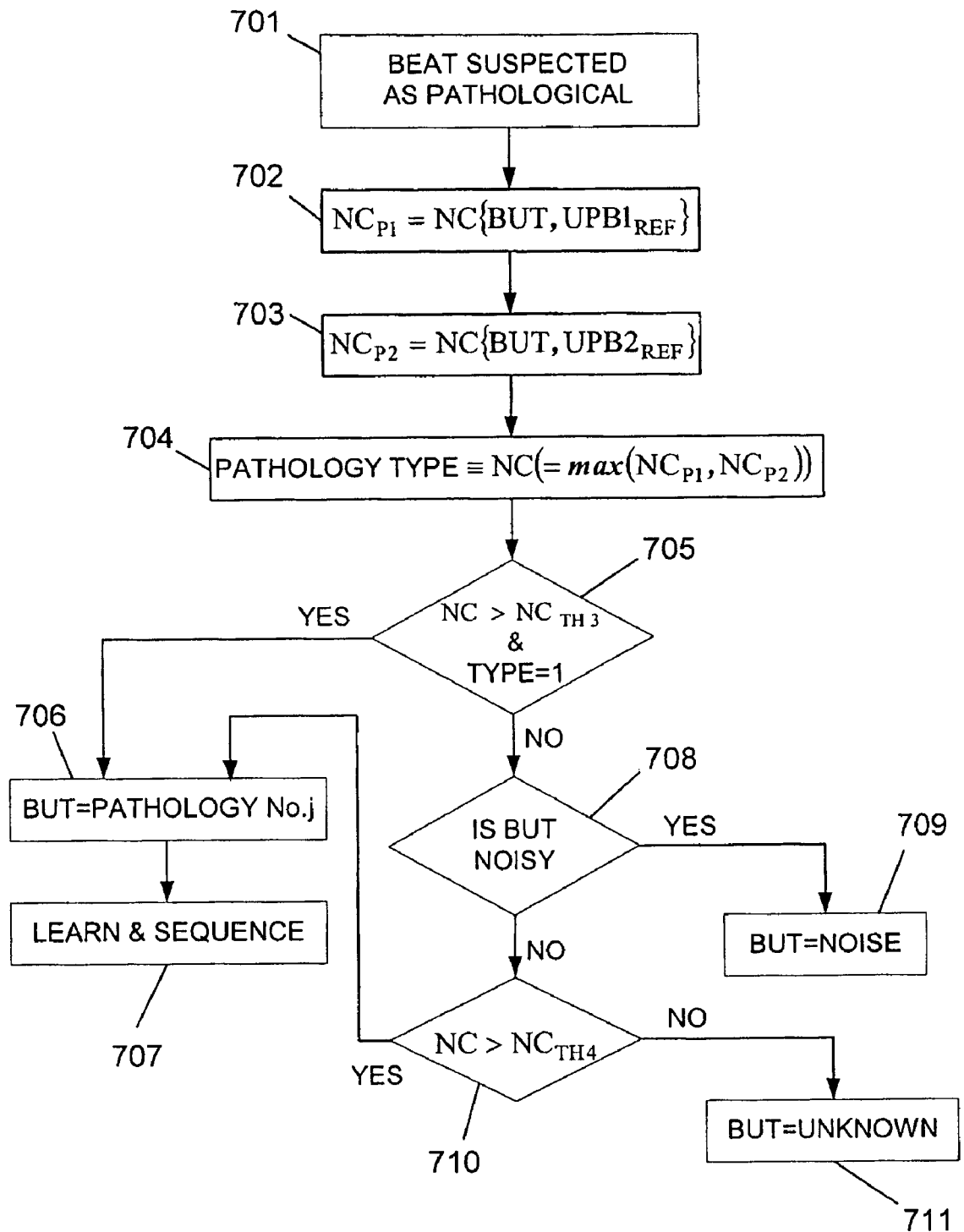
FIG. 7 schematically illustrates the pathological heartbeat first classification process, according to the preferred embodiment of the invention.

FIG. 7 schematically illustrates the pathological heartbeat first classification process, according to the preferred embodiment of the invention. Generally, there are two typical types of aberrant heartbeat patterns associated with common heart pathologies. These types of aberrant heartbeat patterns are represented by the Universal Pathological heartBeat No. 1 (UPB1) and the Universal Pathological heartBeat No. 2 (UPB2), and utilized by the system as reference templates. After deciding that a BUT is suspected as pathological (701) (see reference numeral 305 in FIG. 3), the system further examines it by comparing it to the UPHB1 (702) and to UPHB2 (703), and a first and a second Normalized Correlation (NC) values, i.e., $NC_{P1}$ and $NC_{P2}$, respectively, are calculated (702 and 703, respectively). The maximal NC value is chosen (704), which associates the BUT with the most probable corresponding pathological type of the BUT. If the condition $NC>NC_{TH3}$ is met (705), it indicates that the current BUT is indeed pathological, the type of which is determined according to 704, and the system utilizes this BUT for learning the patient's individual heartbeats, and for analyzing possible pathological sequences of heartbeats (707). However, if the latter condition is not met, the noise content of the current BUT is analyzed, and a decision is made by the system, whether the current BUT is noise (709) or another (weaker) criteria should be employed (i.e., in order to avoid mis-detection of severely corrupted pathological heartbeats). Accordingly, if the condition $NC>NC_{TH4}$ is met (710, $NC_{TH4} \approx 0.25$), the current BUT is considered as pathological (706). Otherwise, the system decides that the pattern of the BUT is unknown (711).

After a BUT is pathologically classified (706), it is utilized for updating the corresponding Universal Pathological heartBeat (UPB) reference template, to which the new BUTs are compared, by averaging the 'n' last known pathological heartbeats (of same type). The updated UPB reference template becomes the Patient-Specific Pathological Heartbeat (PSPHB) reference, since the system converges into (i.e., learns) the pathological patterns of the patient under examination.

Figure 8:
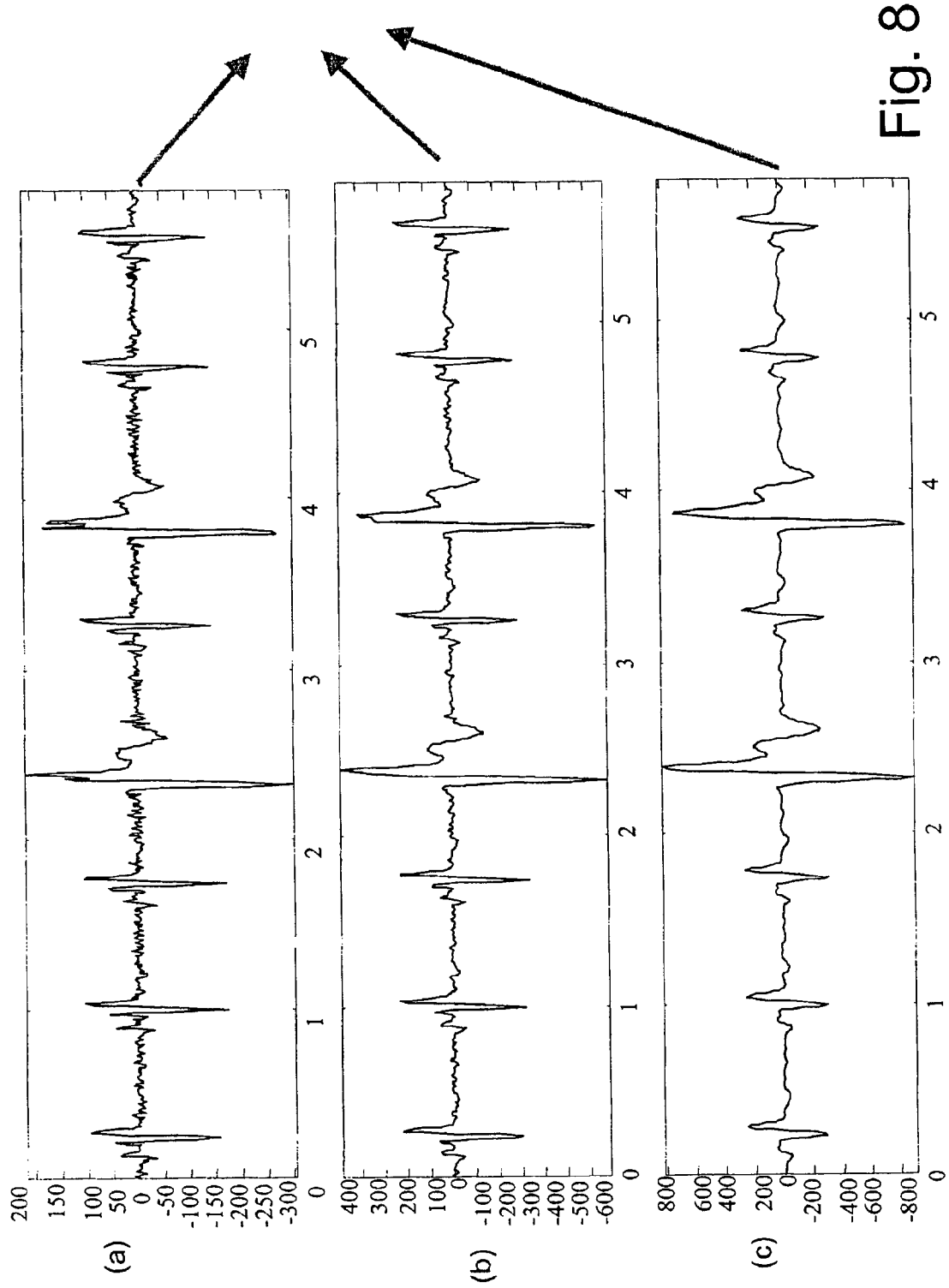
FIG. 8 illustrates R-peak detection by employing the Wavelet algorithm on ECG signal, according to a preferred embodiment of the present invention.
Figure 8:
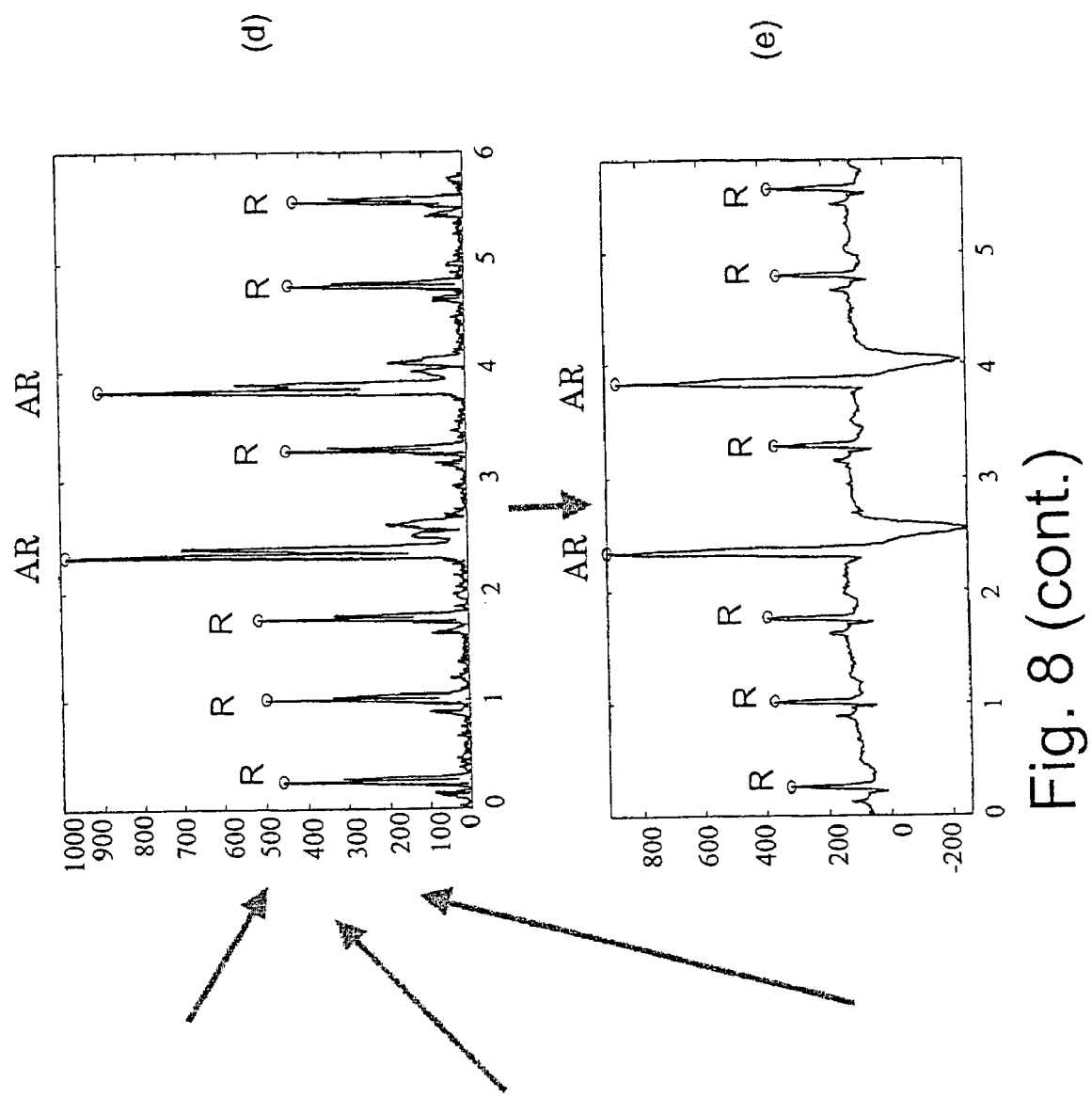

FIG. 8 illustrates R-peak detection by employing the Wavelet algorithm on ECG signal, according to a preferred embodiment of the present invention.

Figure 9:
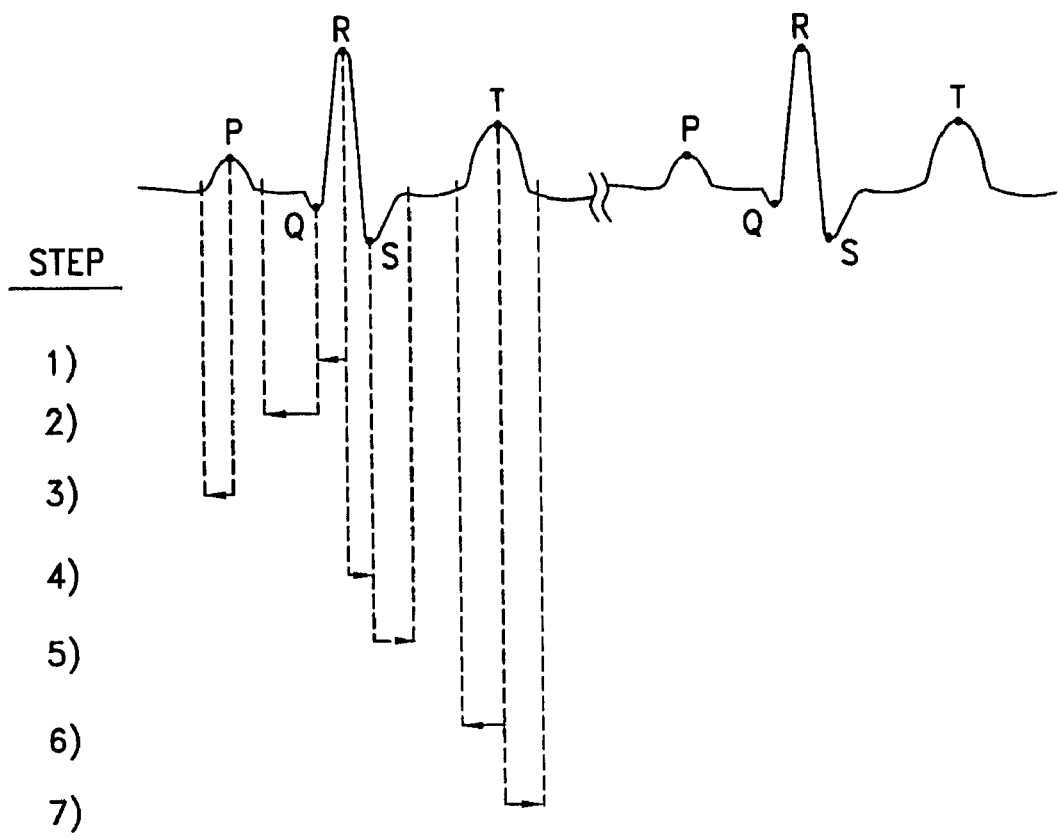
FIG. 9 schematically illustrates the segmentation process of Normal heartbeats, according to a preferred embodiment of the present invention.

FIG. 9 schematically illustrates the segmentation process of Normal heartbeats, according to a preferred embodiment of the present invention. The Wavelet Transfer Algorithm (WTA) is utilized for precise identification of the R-peak of each BUT. The WTA is also utilized for precise identification of the P-peak, T-peak, T(onset) and T(off) of each BUT. The system utilizes the R, P and T peaks for identifying also the P(onset), Q-peak, Q(onset), S-peak and S(off) of the BUT. In 1, 2 and 3, the system analyzes the section on the left-hand side of the (known) R-peak, for identifying the Q-peak, Q(onset) and P(onset). In 4, 5, 6 and 7, the system analyzes the sections on the right-hand side of the R-peak, for identifying the S-peak, S(off), T(onset) and T(end). Accordingly, the system identifies the QRS complex, ST-segment, QT-segment and the PR-segment of each BUT, provided that the BUT is identified as a viable heartbeat (as opposed to a BUT that is too deformed/distorted or noisy), which allow identification of heartbeat abnormalities other than the two commonly known Pathological heartbeat shapes.

Since the system's search for the above-described P, Q, R, S and T points is synchronized to the R—R interval (i.e., the duration between two consecutive R-peaks), it is clearly obvious that the segmentation process adapts itself to the heart-rate of the monitored patient.

Figure 10:
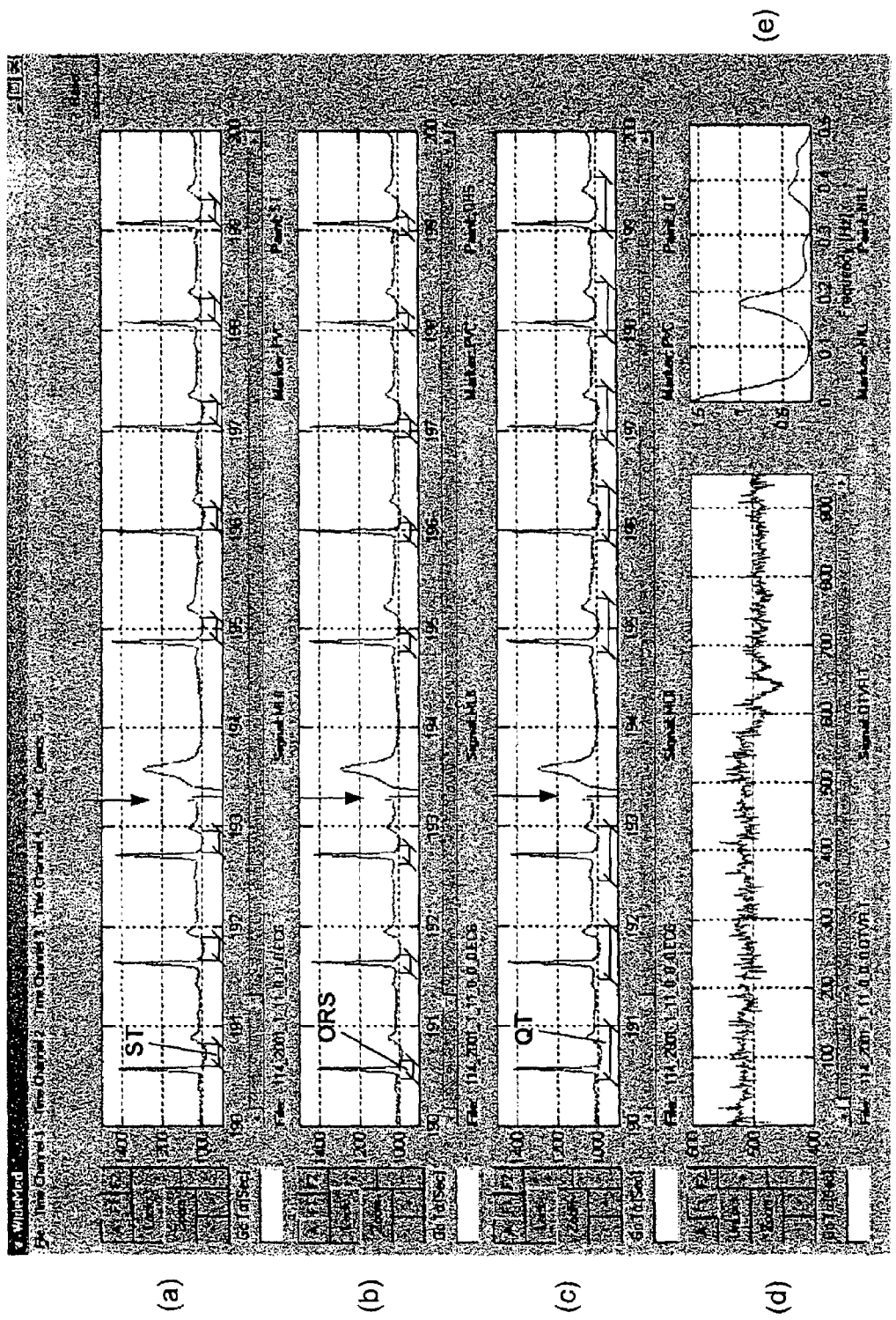
FIGS. 10a to 10e show test results that emphasize the various segments of Normal heartbeats, according to the preferred embodiment of the present invention.

FIGS. 10a to 10e show testing results that emphasize the various segments of Normal heartbeats, according to the preferred embodiment of the present invention. In FIG. 10a, the 'ST' segments are distinguished from the other segments by corresponding horizontal lines. Likewise, in FIG. 10b, the 'QRS' segments are distinguished from the other segments by corresponding horizontal lines, and in FIG. 10c, the 'QT' segments are distinguished from the other segments by corresponding horizontal lines. The latter segments were originally marked by red color, which is could not be visible in the figures. Therefore, the red color has been replaced by horizontal lines to indicate the corresponding segments. FIG. 10d shows the 'QTV' segments, and FIG. 10e shows the spectrum of the QTV segment. Pathological heartbeats are not segmented, as is shown in FIGS. 10a, 10b and 10c. As can be seen in FIGS. 10a, 10b and 10c, the pathological heartbeats is not segmented.

Figure 11:
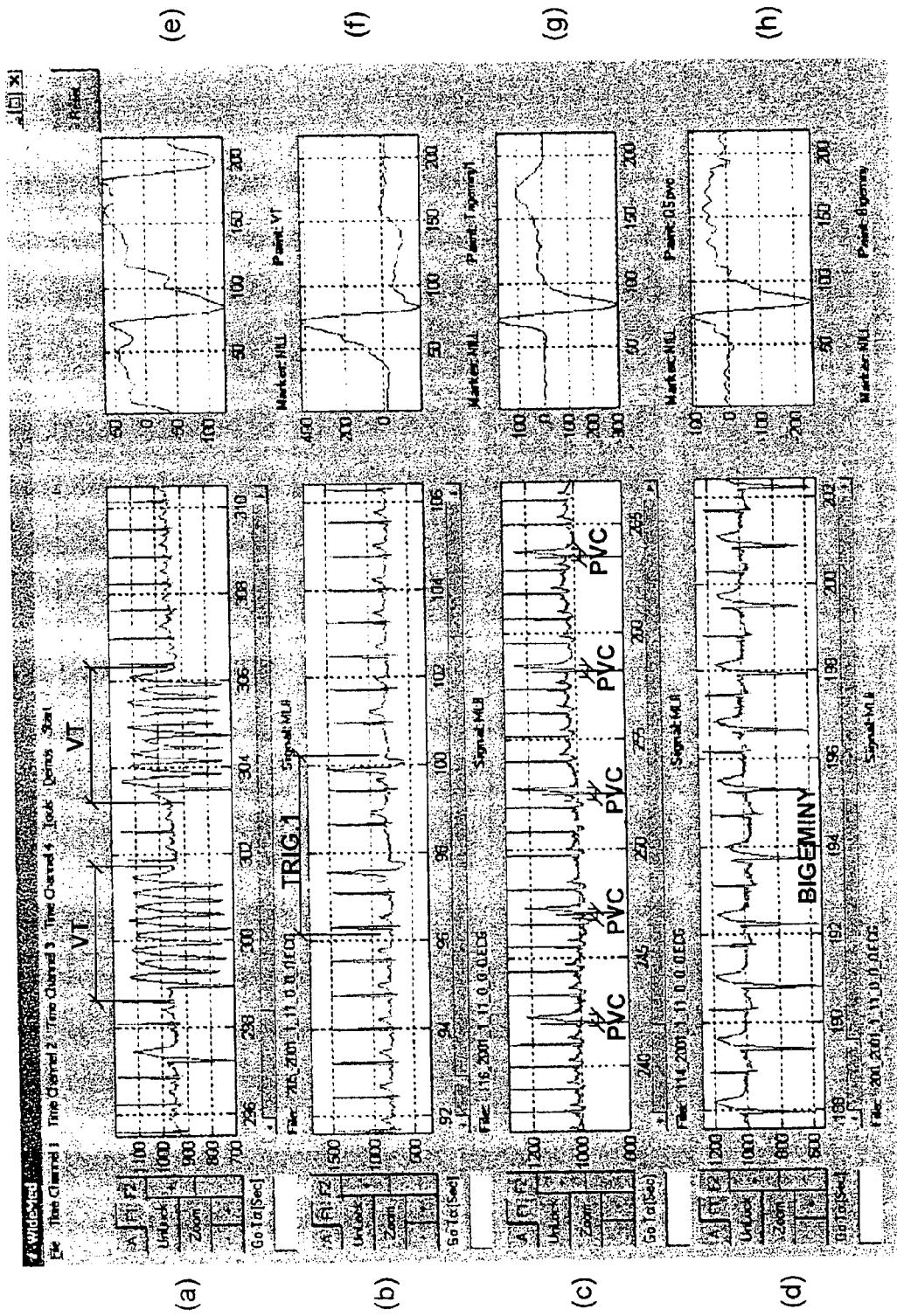
FIGS. 11a to 11h show test results that were obtained by monitoring four persons having different types of arrhythmias, according to the preferred embodiment of the present invention.

FIGS. 11a to 11h show testing results that were obtained by monitoring four persons having different types of pathological heartbeats, according to the preferred embodiment of the present invention. FIG. 11a shows 'VT' type pathological heartbeats that were taken from a first patient. FIG. 11b shows 'Trigeminy 1' type pathological heartbeats that were taken from a second patient. FIG. 11c shows isolated 'PVC' type pathological heartbeats that were taken from a third patient, and FIG. 11d shows 'Bigeminy' type pathological heartbeats that were taken from a third patient. The problematic heartbeats were originally marked by red color, which could not be visible in the figures. Therefore, the red color has been replaced by horizontal lines to indicate the corresponding segments to which the description refers.

FIGS. 11e to 11h show the different pathological heartbeats morphologies as detected by the system, per patient. For example, FIG. 11e shows a typical pathological heartbeat of 'patient (a)' (i.e., shown in FIG. 11a), which has been time-wise stretched in order to allow a close examination of its nature. Likewise, FIGS. 11f to 11h refer to patient (b), (c) and (d), respectively.

Figure 12:
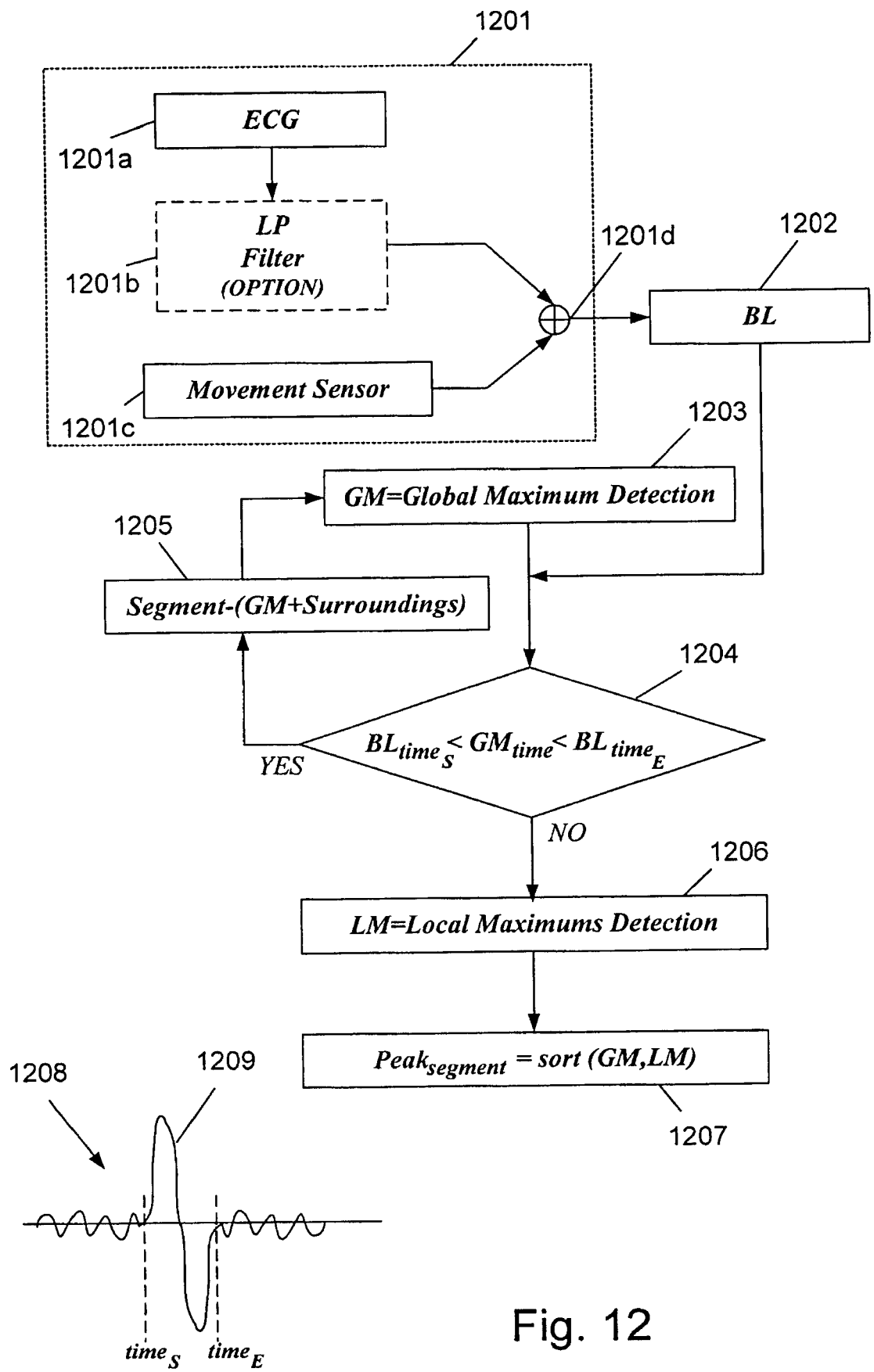
FIG. 12 schematically illustrates the process of detecting a large accidental peak that was superimposed on heartbeats, according to a preferred embodiment of the present invention.

FIG. 12 schematically illustrates the process of detecting a large accidental peak that was superimposed on heartbeats, according to a preferred embodiment of the present invention. As described before, the peaks of the R-waves are detected by employing the WTA on the ECG signal. However, the latter detection is based on using a global maximum (i.e., per ECG segment) as reference, which could lead to heartbeat misdetection if there is an artifact with relatively large peak in the analyzed ECG segment. Therefore, such artifacts must be identified and removed/discarded from the ECG segment. Numeral reference 1201 is the acquiring part of the system. The sampled ECG signal (1201*a*) is superimposed on a data picked-up by movement sensor 1201*c*, in order to establish a Base-Line (BL) reference. Alternatively, at the absence of a movement sensor, the ECG signal is 'lowpass-filtered' (1201*b*), for obtaining the required BL reference signal (1208). In connection with BL signal (1202), a 'Local Maximum Peak' algorithm (1204) is utilized, for automatically detecting the most significant Local 'Maximum' peaks. Whenever a peak-point (not shown) is detected in the ECG signal (1201*a*), a corresponding movement (1209) is searched for in BL reference signal 1208. If such a movement is detected, the starting and ending instants of which being marked as $time_S$ and $time_E$ (in 1208), respectively, and the ECG peak 'falls' between said starting and ending instants, the corresponding ECG peak, together with its corresponding surroundings, is discarded and ignored (1205), because it is suspected as an artifact. The Local 'Maximum-peak' algorithm utilizes as a reference the Global Maximum of the entire new signal (1203), to which the local Maximum is compared. After discarding the artifact global maximum, the next global maximum is continued to be searched for within this segment, which is not suspected as artifact. Whenever such global maximum is found (i.e., that is not an artifact), it is utilized as a reference for the next ECG peaks. Nevertheless, the global maximums suspected as artifacts are saved, along with the rest of the local peaks, for later manipulations.

If several consecutive local maximums were found within an ECG segment, which were not suspected as artifacts (1206), the system refers to the largest maximum peak detected (i.e., within the ECG segment) as the global maximum for this particular ECG segment (1207).

Figure 13:
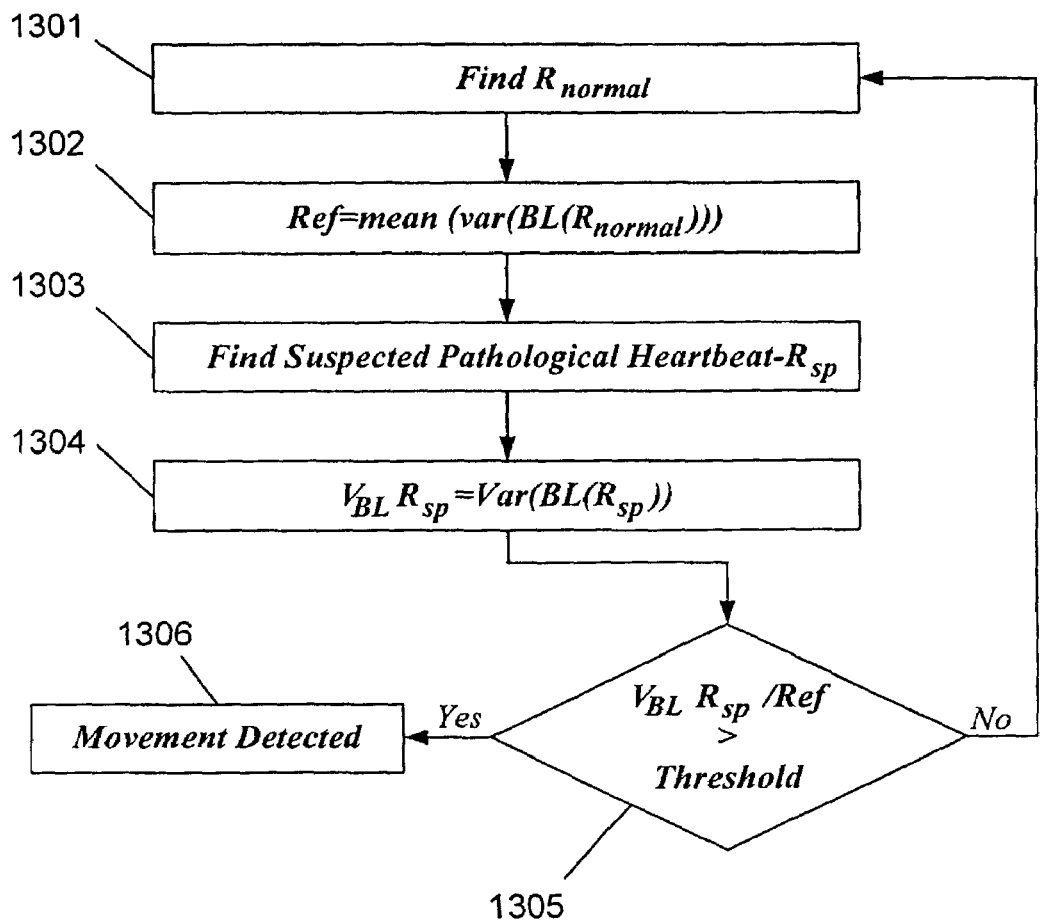
FIG. 13 schematically illustrates adaptive detection of low frequency movements that are superimposed on viable heartbeats, according to a preferred embodiment of the present invention.

FIG. 13 schematically illustrates adaptive detection of low frequency movements, according to a preferred embodiment of the present invention. The most problematic types of artifacts are those in the spectral range of the ECG signal, caused by patient movements, cable movements, etc. Artifacts having a frequency content that is similar to that of the actual ECG signal being recorded evidently can interfere with the correct interpretation of the ECG signal. In order to detect this type of artifacts, a base line is extracted from the ECG signal, which represents the status of the monitoring hardware and the inherent physiological status of the monitored person, and an adaptive algorithm is utilized for detecting changes in the base line.

The system finds the 'normal' R-peaks (1301), and since their magnitude is likely to vary in time, the variance is averaged and the mean value is used as a reference (1302). The adaptive movement detection checks if there is a change in the variance (1305) of the base line in the environment of a heartbeat that is suspected as pathological (1303), according to the reference that was calculated adaptively according to the environment of the normal heartbeats (1302). If the ratio between the current variance to Ref. (1302), is larger than a threshold value (1305), it indicates that a movement has been detected. Otherwise, the system continues to find R-peaks (1301) and to update the Ref. (1302).

Figure 14:
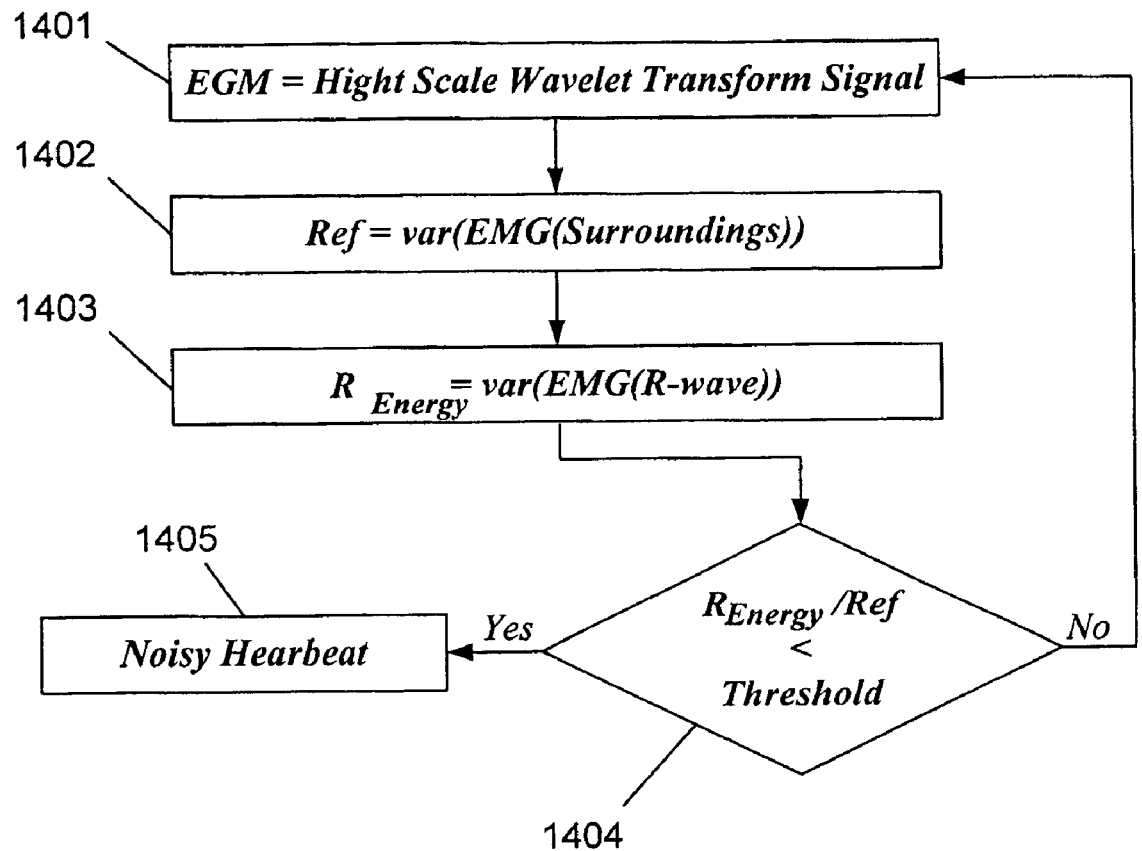
FIG. 14 schematically illustrates adaptive detection of high frequency EMG and noise signals that are superimposed on viable heartbeats, according to a preferred embodiment of the present invention.

FIG. 14 schematically illustrates adaptive detection of high frequency EMG and noise signals that are superimposed on viable heartbeats, according to a preferred embodiment of the present invention. This type of noise is characterized by having high frequency components caused by external noise and by muscle activity of the monitored person. In order to detect this type of noise, an adaptive detection algorithm was developed, which utilizes the high scale of the Wavelet Transform Algorithm (WTA) (1401). Using the WTA allows analyzing the energy of the surroundings of individual R-waves, and determining a corresponding Ref. (1402). Than, the energy of the R-wave is analyzed and a corresponding reference (i.e., $R_{Energy}$, 1403) is calculated. The ratio between the two references (i.e., $R_{Energy}$/Ref.) is calculated (1404), and if this ratio is larger than a threshold value, it indicates that the current heartbeat is noiseless (and the system continues by analyzing the next R, since in a noiseless heartbeat, as reflected in the ECG signal, the R-wave energy is much stronger than its surroundings. Otherwise, the current heartbeat is considered as noise (1405).

The analysis of the energies are analyzed, and the corresponding references (i.e., Ref. and $R_{Energy}$) recalculated, per R-wave and its surroundings, thereby allowing the system to respond very quickly to noises and EMG events, i.e., essentially immediately after their occurrences. The fast response, as described above, allows the system to utilize essentially every monitored heartbeat (i.e., BUTs) for enhancing the accuracy at which a person's cardiac condition is analyzed.

Figure 15:
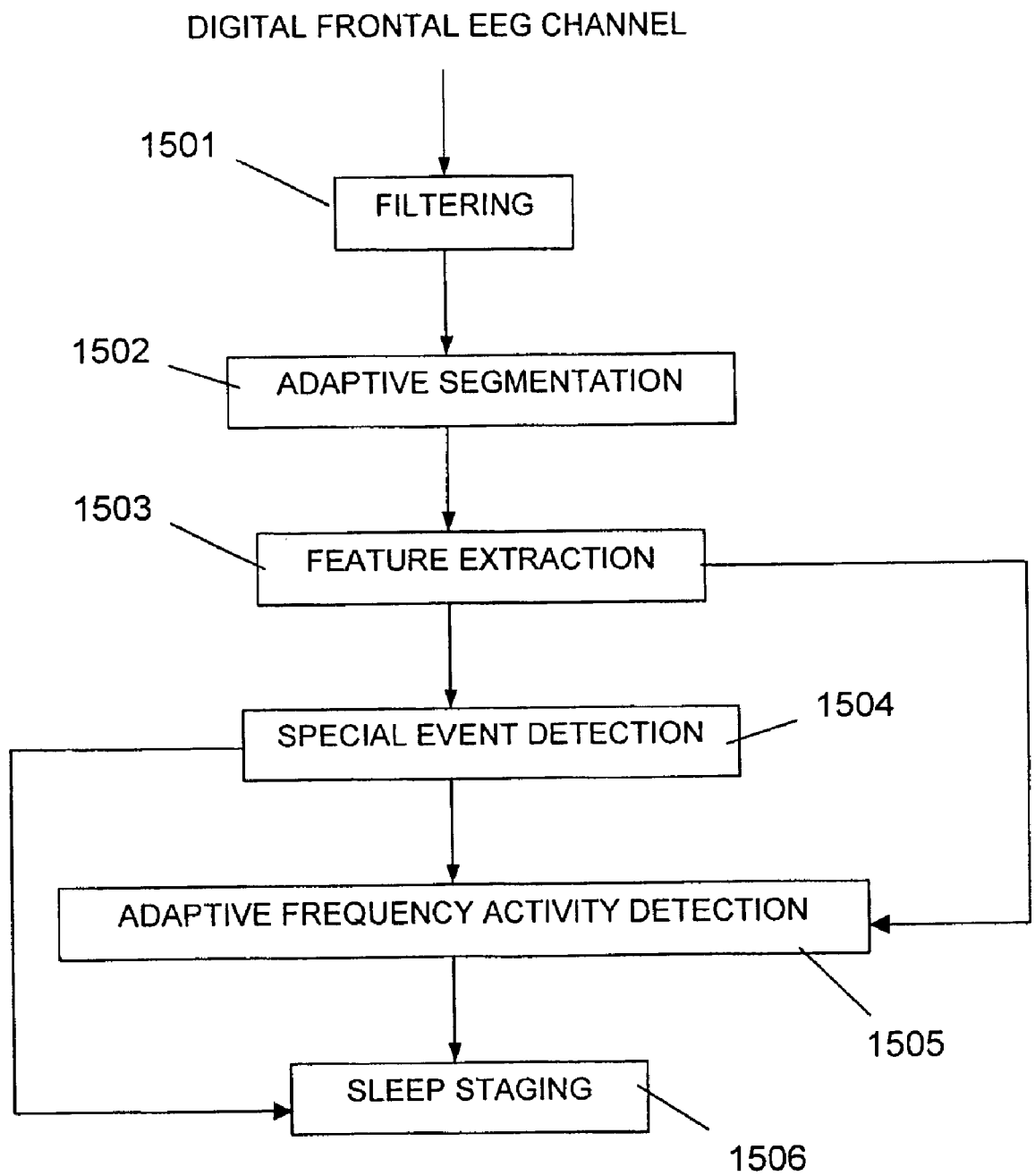
FIG. 15 illustrates a general block diagram of an automatic Sleep Staging System, according to a second embodiment of the invention.

FIG. 15 illustrates a general block diagram of the automatic Sleep Staging System, according to a preferred embodiment of the invention. The disclosed system is configured and programmed to identify the six known sleep stages (i.e., awakening, stages 1, 2, 3 and 4, and dreaming). Filter block, indicated by reference numeral 1501, comprises four Finite Impulse Response (FIR) filters (not shown), which eventually produce three types of signals. The first type is an EMG signal, which is typically superimposed on the EEG signal as interference. The second type is a Slow Frequency EEG (SFEEG), and the third signal is a Fast Frequency EEG (FFEEG).

Adaptive segmentation block, indicated by reference numeral 1502, is an algorithm that is based on an algorithm known as the Generalized Likelihood Ratio (GLR) Test (a reference could be made to http://www.cnmat.berkeley.edu/~tristan/Report/node3.html), which is the basic statistical approach for sequential signal segmentation. The mathematical basis of the GLR will not be described here since it is known to those skilled in the art. The task of the GLR-based algorithm is to partition the resulting filtered signals (i.e., SFEEG, FFEEG and EMG) into quasi-stationary epochs, for allowing identifying and extracting features (1503) that are contained therein. These features are: (1) Mean value, (2) Variance, (3) Skewness, (4) Duration, (5) Relative Energy in Delta Frequency Band (1-3.5 Hz), (6) Relative Energy in Theta Frequency Band (4-7 Hz), (7) Relative Energy in Alpha Frequency Band (7.5-12 Hz), (8) Relative Energy in Sigma Frequency Band (12.5-15 Hz); and (9) Relative Energy in Beta Frequency Band (15-35 Hz). Features Nos. (1) to (4) are time-wise features, and features Nos. (5) to (9) are spectrum-wise features. All of the nine features are extracted from the (filtered) EEG signal, but only features Nos. (1) to (4) are affected by the EMG signal.

Identification of the above-specified features allows detecting, by utilizing the block indicated by reference numeral 1504, the following events: (1) K-complexes, (2) Body movements, (3) Electrode movements, (4) Rapid eye movements, (5) Eye blinks, (6) Spindles; and (7) Alpha intrusions. Events Nos. (1) to (5) are time transients and are easily extracted from the ongoing EEG signal due to their distinguishable energy, skewness and duration in relation to said EEG signal. The time transient events (i.e., events 1 to 5) are classified using their new environment frequency behavior and their time domain morphology. Events Nos. (6) and (7) are frequency transients and are detected by measuring their duration and by analyzing their spectral behavior.

In order to obtain only pure features of ongoing sleep stages from the EEG signal, an Adaptive Frequency Activity Detection (AFAD) module is utilized, indicated by reference numeral 1505, which is based on the Hidden Markov Model (HMM), which is also known as the "Forward-Backward Algorithm". HMM models are utilized for extracting signal patterns of interest, by characterizing their frequency variations. In the present invention, these models are utilized for optimizing a patient-learning process by analyzing three major groups of frequency activities (i.e., High Frequency, Mixed Frequency and Low Frequency). The functionality of the HMM model will not be discussed since it is known to those skilled in the art. A notion, regarding HMM models, could be found in the article "Hidden Markov Model (HMM) Toolbox", which is given in the Internet web site http://www.cs.berkeley.edu/~murphyk/Bayes/hmm.html.

Another model used for learning individual patients is the Abstract State Machine (AMN) model, a notion of which could be found in a book called "Software Engineering with B", by J. B. Wordsworth, Published August 1996 by Addison Wesley Higher Education. For additional details visit the Internet web site http://www.pearsonptg.com/book_detail/0,3771,0201403560,00.html).

After detecting the time transient events, their features are subtracted from the features signals, resulting in pure features sleep EEG only. The spectral features 5, 6, 7 and 9 (relative Energy in Delta Frequency Band, Theta Frequency Band, Alpha Frequency Band and in Beta Frequency Band, respectively) are input into two HMM model types, as illustrated in FIG. 18, for detecting frequency activities.

Figure 16:
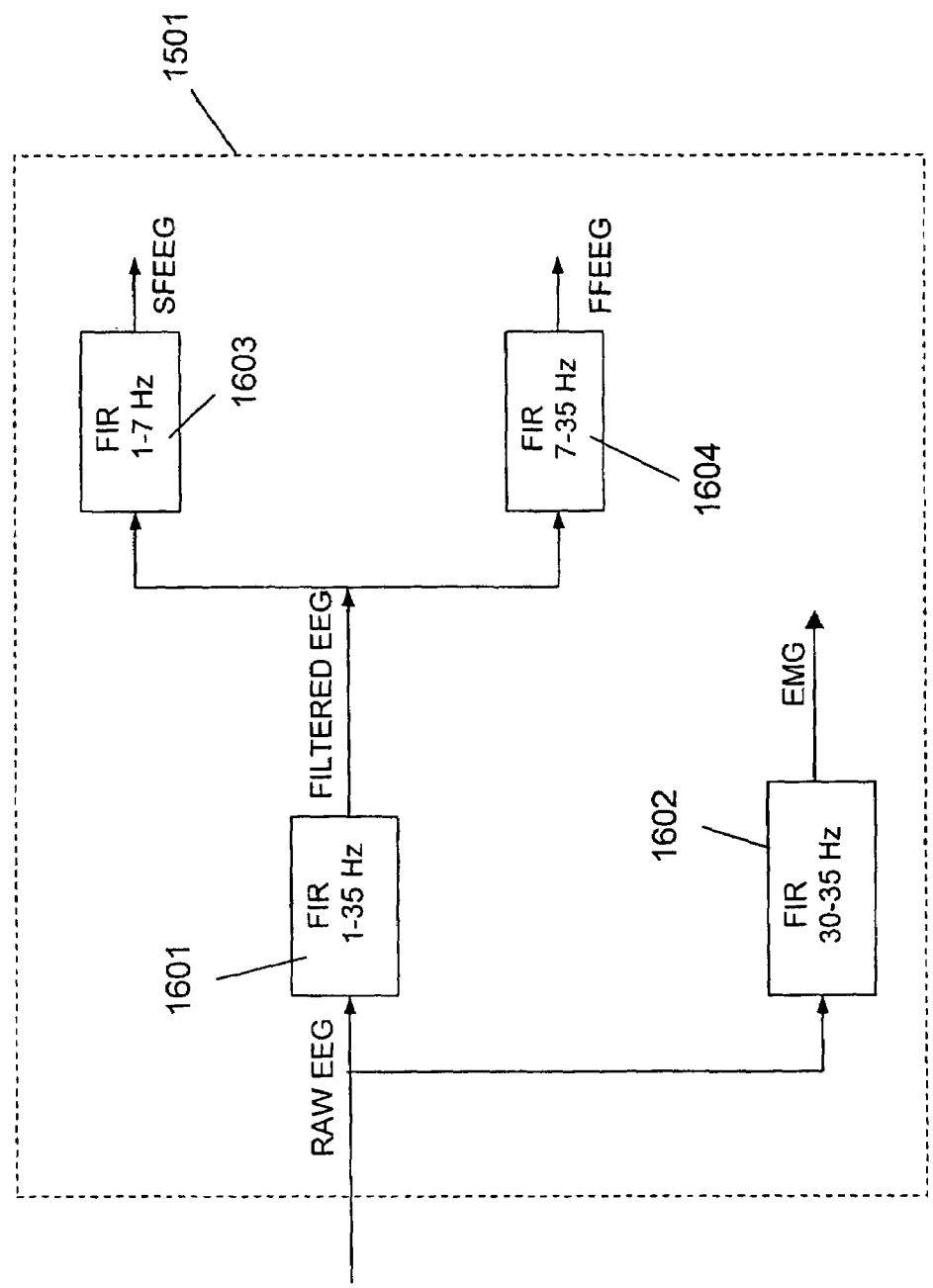
FIG. 16 schematically illustrates filtering of an EEG signal, according to a preferred embodiment of the present invention.

FIG. 16 schematically illustrates extraction of the SFEEG, FFEEG and the EMG signals from the raw EEG signal, according to a preferred embodiment of the invention. Filter 1601, being FIR 64-order Band Pass Filter (BPF) 1-35 Hz, essentially removes the EMG signal from the raw EEG signal and cancels drifts in the base line of the EEG signal. The filtered EEG signal is, then, decomposed by two filters—filter 1603, being FIR 64-order BPF 1-7 Hz, and filter 1604, being FIR 64-order BPF 7-35 Hz, into SFEEG signal and FFEEG signal, respectively. Filter 1602, being FIR 64-order BPF 30-35 Hz, extracts the EMG signal for further analysis.

Figure 17:
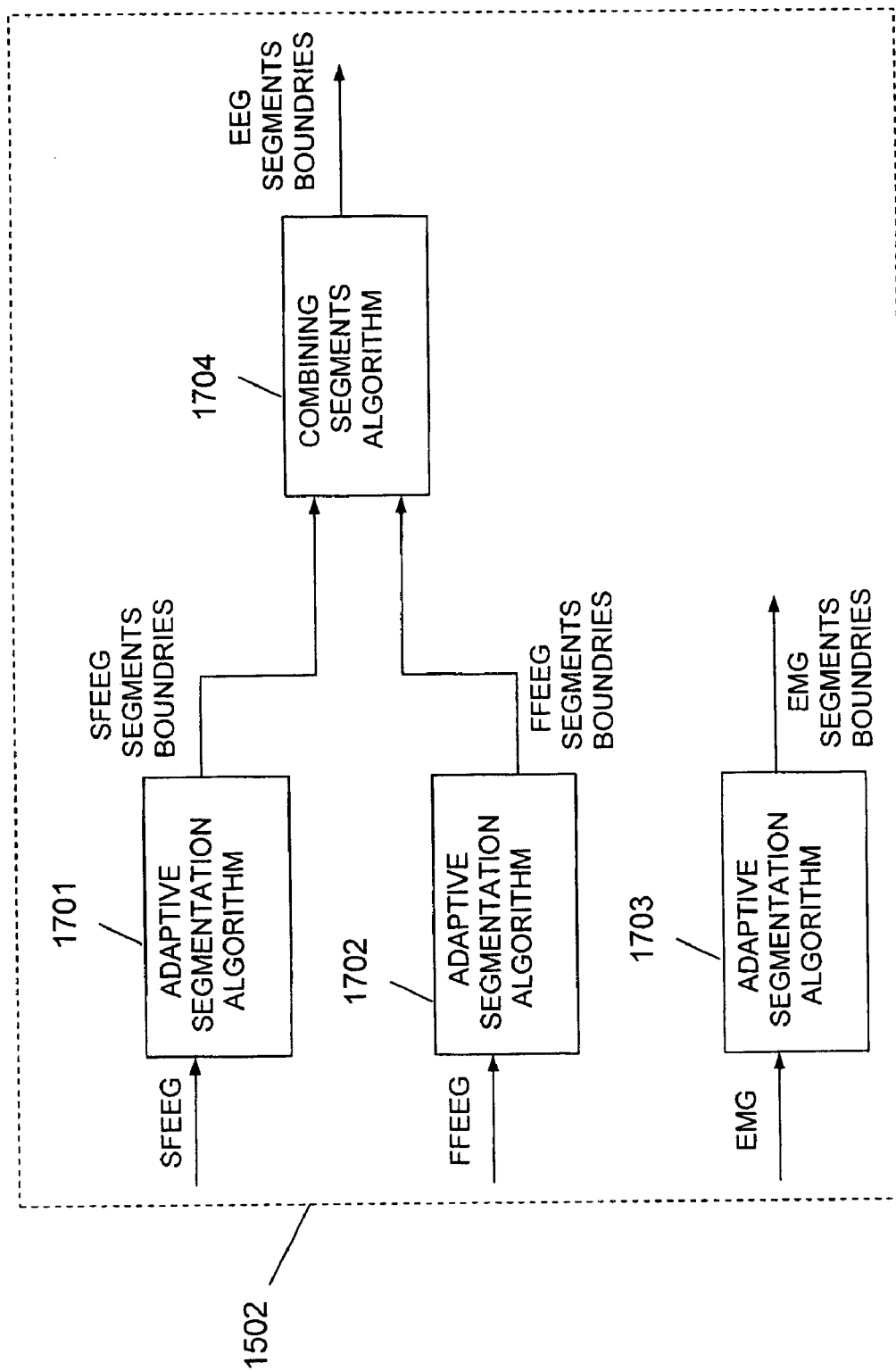
FIG. 17 schematically illustrates adaptive segmentation process of an EEG signal, according to a preferred embodiment of the present invention.

FIG. 17 is a block diagram illustrating adaptive identification of the boundaries of duration-variable segments in the SFEEG signal, in the FFEEG signal and in the EMG signal, according to a preferred embodiment of the invention. Adaptive segmentation algorithm 1701 is employed on the SFEEG signal, for identifying segments that are associated with corresponding sleeping stages. Likewise, adaptive segmentation algorithms 1702 and 1703 are employed on the FFEEG signal and on the EMG signal, respectively. The SFEEG and FFEEG boundaries are then combined (1704). After identifying the above-mentioned boundaries, the corresponding features and special events are extracted (FIG. 15, reference numerals 1503 and 1504, respectively).

Figure 18:
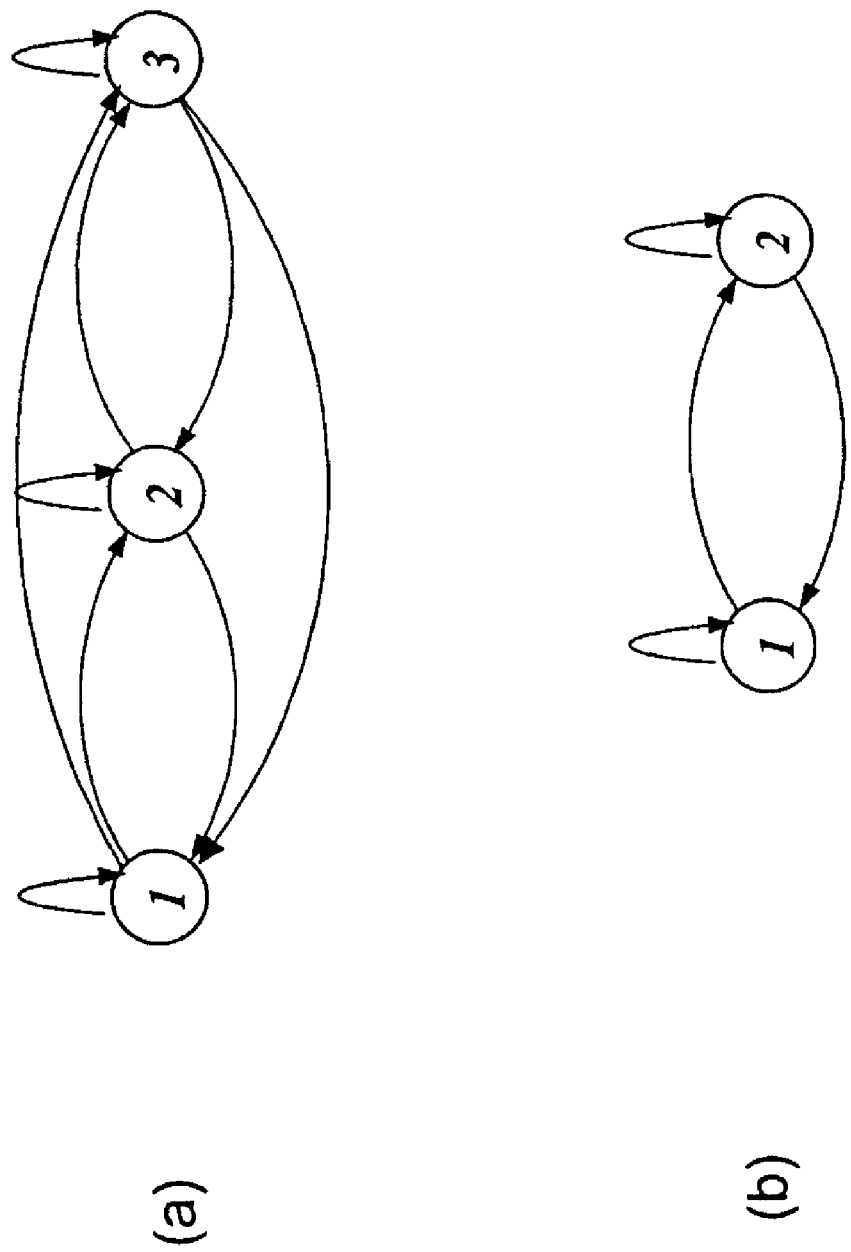
FIG. 18 schematically illustrates detection of frequency activities by utilizing a three-state HMM model (a) and a two-state HMM model (b), according to a preferred embodiment of the present invention.

FIG. 18 schematically illustrates detection of frequency activities by utilizing a three-state HMM model (a) and a two-state HMM model (b), according to a preferred embodiment of the present invention. The incentive for utilizing the HMM models is the ongoing sleep EEG signal being a Markovian process, namely, the current status of the EEG signal is largely affected by its past behavior. Therefore, only several particular transfers, from one stage to another, are allowed from statistical point of view. According to the invention, the frequency spectrum involved in sleep stages is divided into three groups of frequency activity, each group indicating a different sleep stage: (1) Fast Frequency Activity (FFA), (2) Mixed Frequency Activity (MFA); and (3) Slow Frequency Activity (SFA). The latter groups being indicated by reference numerals '1', '2', and '3' (see FIG. 18a). The goal in utilizing the HMM models is to decide which model (i.e., (a) or (b)) better describes the sleep status at a given time. Model (a) indicates that the patient was sleeping deeply, and model (b) indicates that the patient was having a 'light' sleep. Each stage is characterized by a 4-dimensional probability Gaussian. Passing from one type of activity (i.e., sleep stage) to another is characterized by a corresponding probability. For example, the probability of passing from state 1 (i.e., FFA) to state 2 (i.e., MFA) is higher than the probability of passing from state 1 to state 3 (i.e., SFA).

The decision criteria, according to which the three-state model, or the two-state model, is chosen, is the relative energy (in percentage) of the delta-wave. If the latter energy is larger than 40%, the three-state model is employed. Otherwise, the two-state model is employed. Prior to deciding which model is valid, the system is first initialized by assigning it a set of predetermined global initial conditions (that are input into these models), as well as the patient's feature matrix [Please clarify]. The next step is employing the BAUM WELCH training algorithm, the task of which is to allow the system to converge from the initial statistical properties (i.e., being provided by a clustering algorithm based on a set of fuzzy rules) of each model, into the patient's self-parameters. The BAUM WELCH training algorithm outputs a matrix describing the probability of a patient being in each sleep stage essentially at any given time. The mathematical background of this algorithm will not be discussed, since it is known to those skilled in the art. For example, a reference could be made to the article "Derivation of the Baum-Welch algorithm for HMMs", which could be found in the Internet web site http://www.speech.sri.com/people/anand/771/html/node26.html.

The resulting probability matrix is averaged in time by frames of 30 seconds while avoiding overlapping, and entered, together with the time-wise events, into the R&K operator, in order to obtain a final decision regarding each sleep stage (FIG. 15: 1506). The R&K operator will not be discussed here, as it is known to those skilled in the art. A notion, regarding R&K rules, could be found in the article "Objectives of the SIESTA project", which could be found in the Internet web site http://www.ai.univie.ac.at/oefai/nn/siesta/objectives.html.

Figure 19:
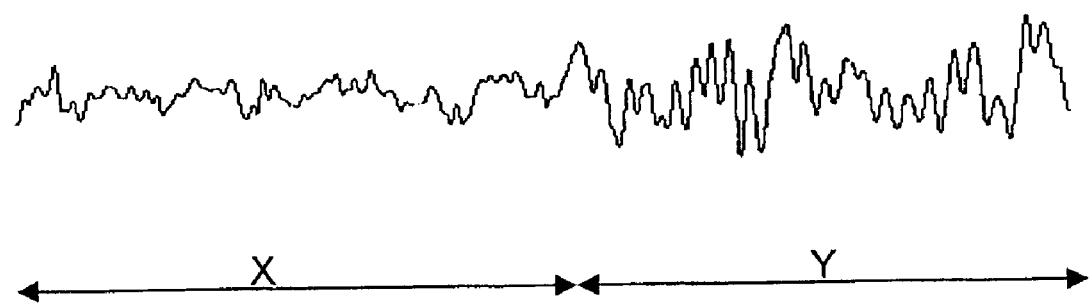
FIG. 19 (prior art) illustrates two quasi-stationary processes that were derived from an EEG signal.

FIG. 19 (prior art) shows an example of two consecutive quasi-stationary segments that were derived from typical EEG signal. In order to decide whether quasi-stationary segments X and Y belong to the same stationary process, the resemblance between their respective statistical properties has to be determined. The greater the resemblance, the more likely that segments X and Y belong to the same stationary process. The extent of the resemblance $\gamma$ ($0 \leq \gamma \leq 1$) is determined by utilizing the GLR algorithm.

Figure 20:
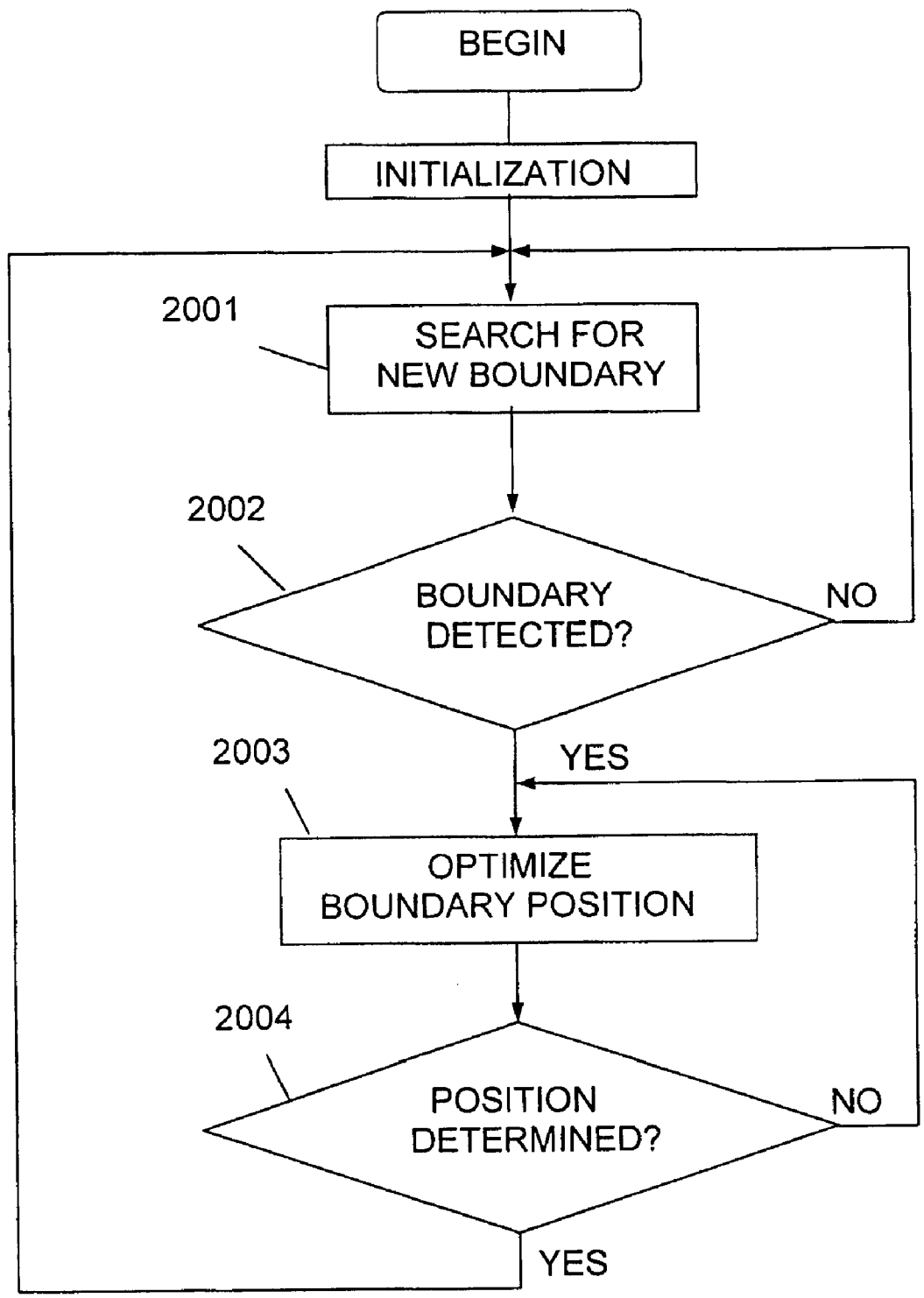
FIG. 20 is a general flow chart of describing the sequential segmentation process, according to a preferred embodiment of the present invention.

FIG. 20 schematically illustrates the principle of sequential segmentation process for identifying quasi-segments in EEG signal, according to a preferred embodiment of the present invention. First, a search process is employed, for identifying a new current potential (temporal) boundary (2001) between two consecutive segments, the latter process being iterative process. Whenever a new boundary is found, a second process is employed (2003), for optimizing the position/location of the potential boundary. After the current boundary's location is optimized (2004), the next current boundary is searched for.

Each two consecutive detected boundaries define the duration of the corresponding segment (i.e., the segment 'locked' between these boundaries).

Figure 21A:
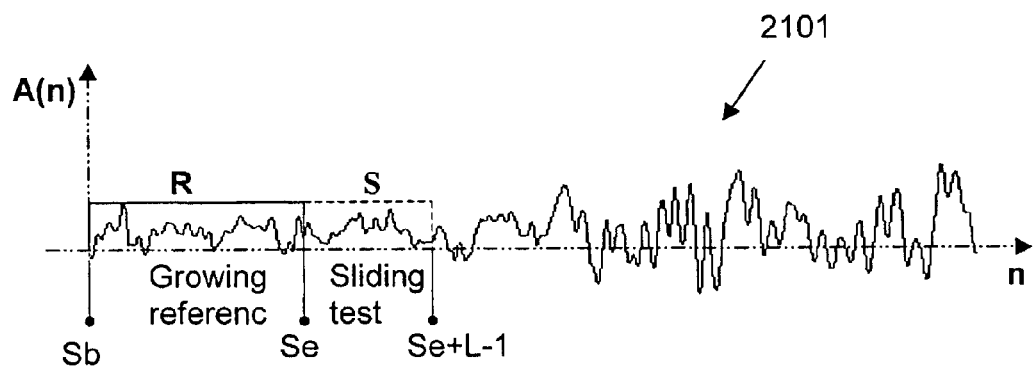
FIG. 21a schematically illustrates the principle of the initial boundaries-detection of a quasi-stationary segment, a preferred embodiment of the present invention.
Figure 21B:
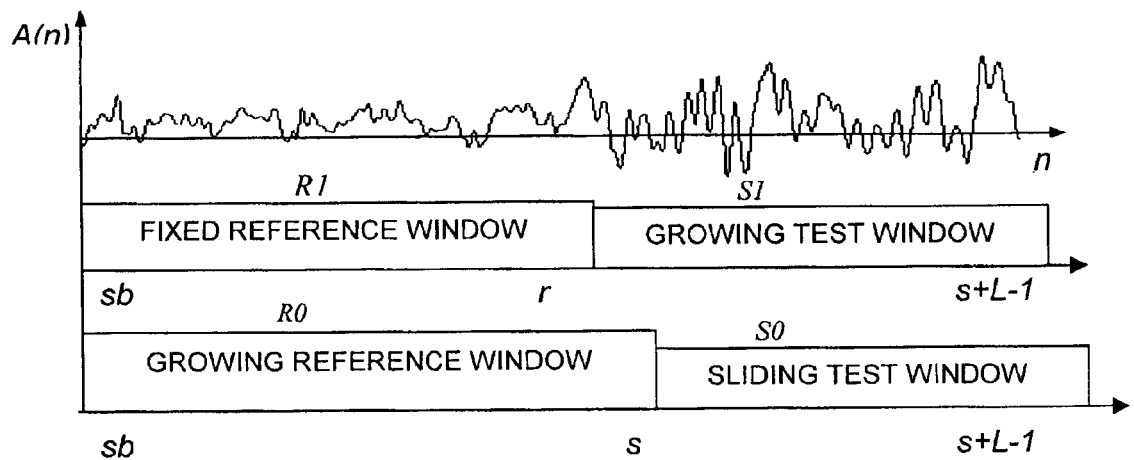
FIG. 21b schematically illustrates the principle of optimization of a boundary location, according to a preferred embodiment of the present invention.

FIG. 21 schematically illustrates the principle of identifying quasi-segments in EEG signal, according to a preferred embodiment of the present invention. The decision process that is utilized for detecting a new boundary at an arbitrary point 'n' (Sb<n<Se+L−1) in a sampled EEG signal is performed by utilizing a Sliding Test Window (STW), marked 'S', and a Growing Reference Window (GRW), marked 'R'. Sequences {R} and {S}, each of which includes corresponding samples of the raw EEG signal, are compared to one another by employing the GLR test. If the (statistical) distance between the latter sequences exceeds a Predetermined Threshold Value (PTV), the GRW and the STW are gradually shifted to the right while maintaining their initial width. The right-shift continues until the GLR distance is smaller than the PTV. At this stage, the optimal boundary (i.e., between two consecutive distinguishable segments) location is assumed to be between Sb and Se, and a process for determining the optimized (i.e., more accurate) boundary location is employed. However, if the GLR distance initially does not exceed the PTV, Se is incremented causing the GRW to grow and the STW to slide to the right, until the GLR distance exceeds the PTV. At this stage, the optimal boundary location is assumed to be between Se and Se+L−1, and the process for determining the optimized boundary location is employed. The above-described process, for determining a new boundary, is repeated until all the boundaries are identified.

Figure 22:
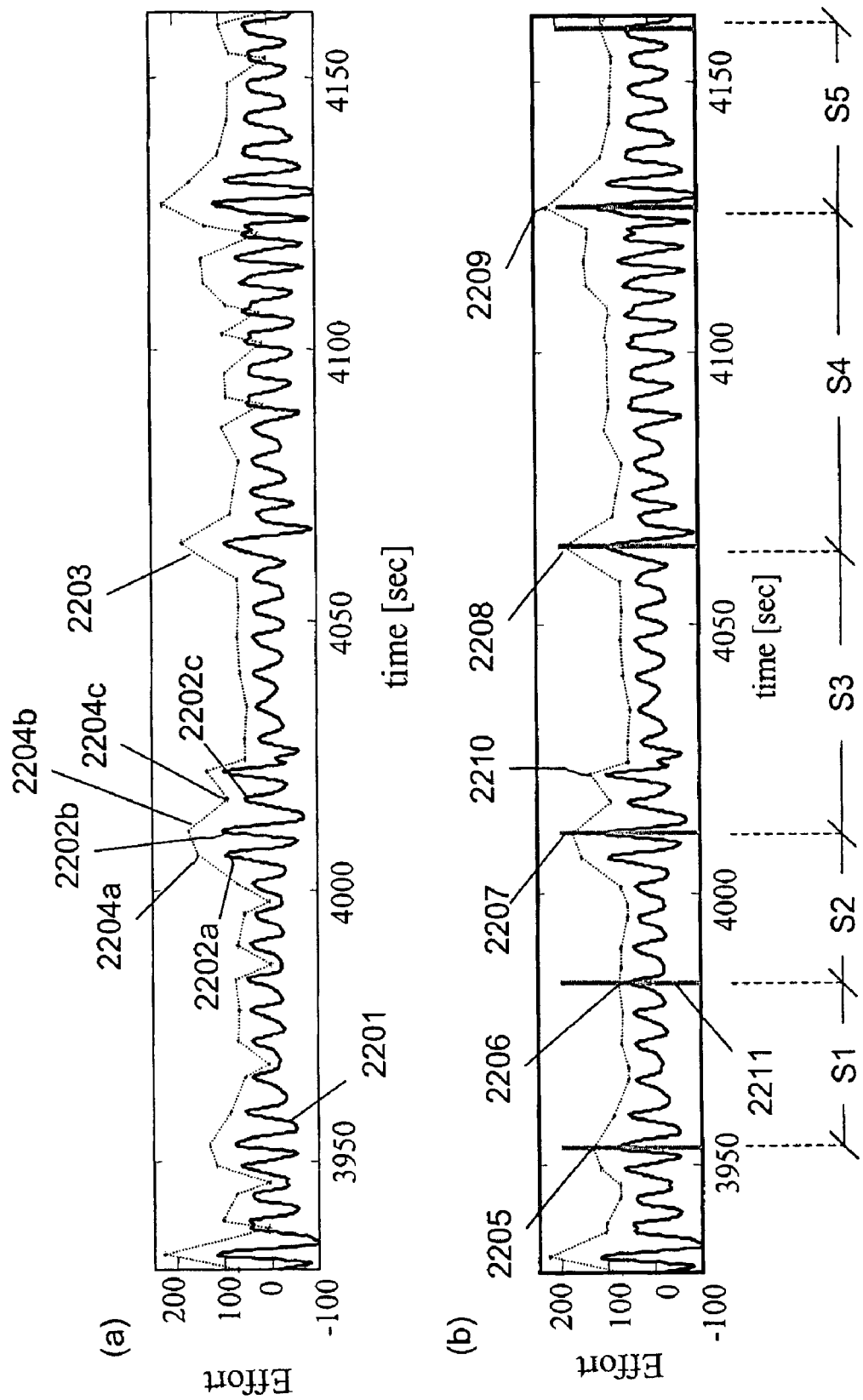
FIGS. 22a and 22b schematically illustrate envelope detection of Respiratory signal, according to the second embodiment of the invention.

FIGS. 22a and 22b are exemplary results showing the envelope of an effort signal and the corresponding segmentation of the effort signal, according to a preferred embodiment of the present invention. In FIG. 22a, the frequency and amplitude of effort signal 2201 change according to the Respiratory rhythm and the physiological status of the monitored person (not shown). Each peak-point in effort signal 2201 is identified, and its amplitude is represented by a corresponding point. For example, the peak-points 2202a, 2202b and 2202c are represented by Amplitude Points (APs) 2204a, 2204b and 2204c, respectively. Envelope 2203 comprises all the APs. The next step is smoothing the signal according to fuzzy logic rules and finding APs that are global maxima, after which their corresponding instants will be utilized as time-boundaries for segmenting effort signal 2203.

In FIG. 22b, APs 2205 to 2209 are global maxima and are indicated by corresponding vertical lines, such as line 2211. AP 2210 is also a global maximum. However, since it is too close (according to a certain criteria) to AP 2207 and smaller than AP 2207, it is not utilized as time-boundary. Accordingly, effort signal 2201 is segmented into segments S1 to S6, and each segment is evaluated.

Figure 23:
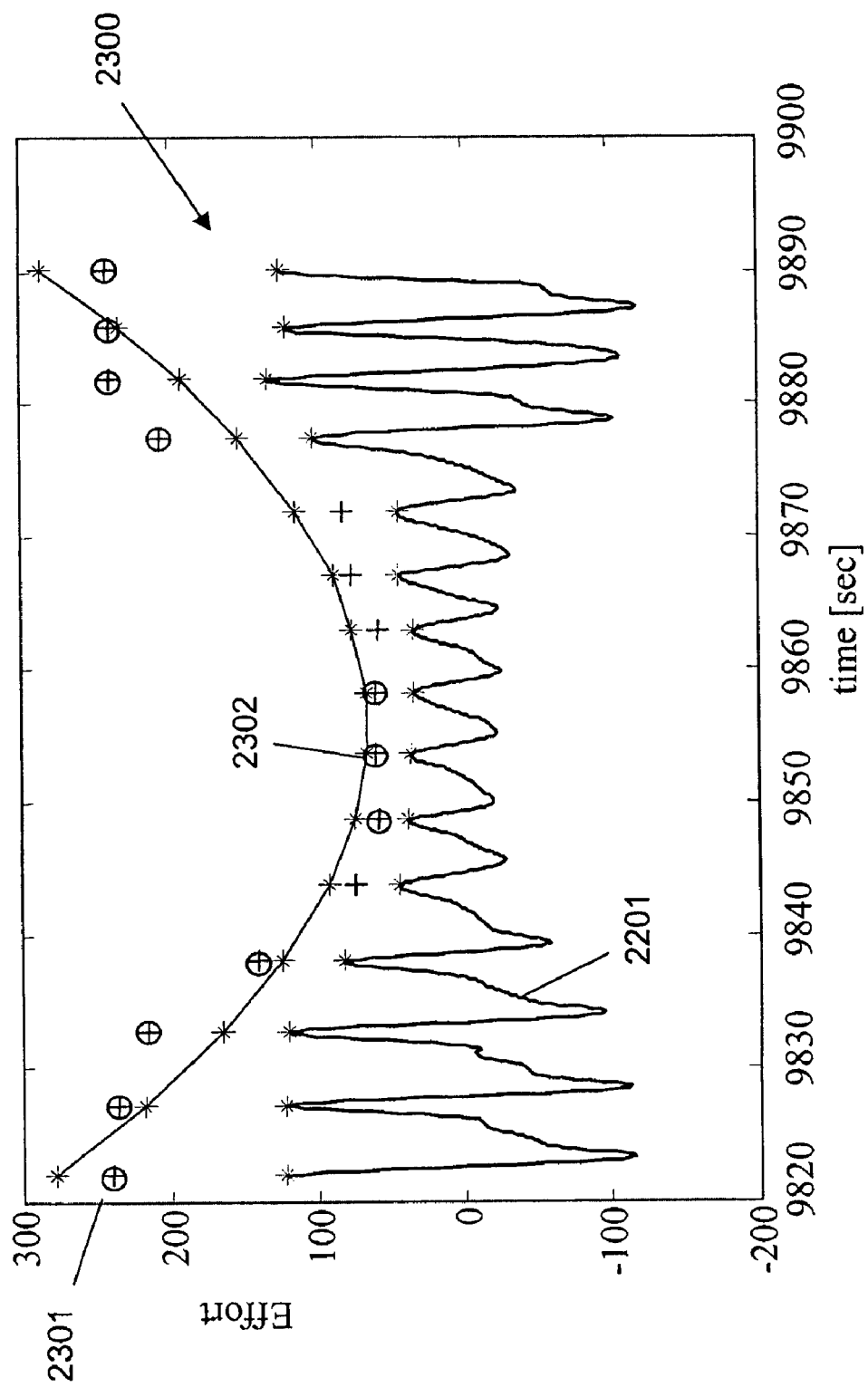
FIG. 23 illustrates utilization of parabola for signal trend evaluation, according to a preferred embodiment of the present invention.

FIG. 23 shows one exemplary segment of the effort signal, according to a preferred embodiment of the present invention. Segment 2300 is evaluated in order to decide whether it reflects an apnea or hypopnea. Accordingly, the magnitude of the mean value of points close to minimal point 2302 is compared to the magnitude of the mean value of points close to the magnitude of maximal point 2301, for evaluating the probability of a magnitude decrease of more than 20%. Another criteria is implemented, according to which it is decided whether the trend of the segment is Up, Down or Even (i.e., 'flat'). If the segment is flat, a corresponding PWW (not shown) is utilized by the FLA, for evaluating the correctness of the assumption e.g., if a respiratory event (hypopnea or apnea) occurred.

Figure 24:
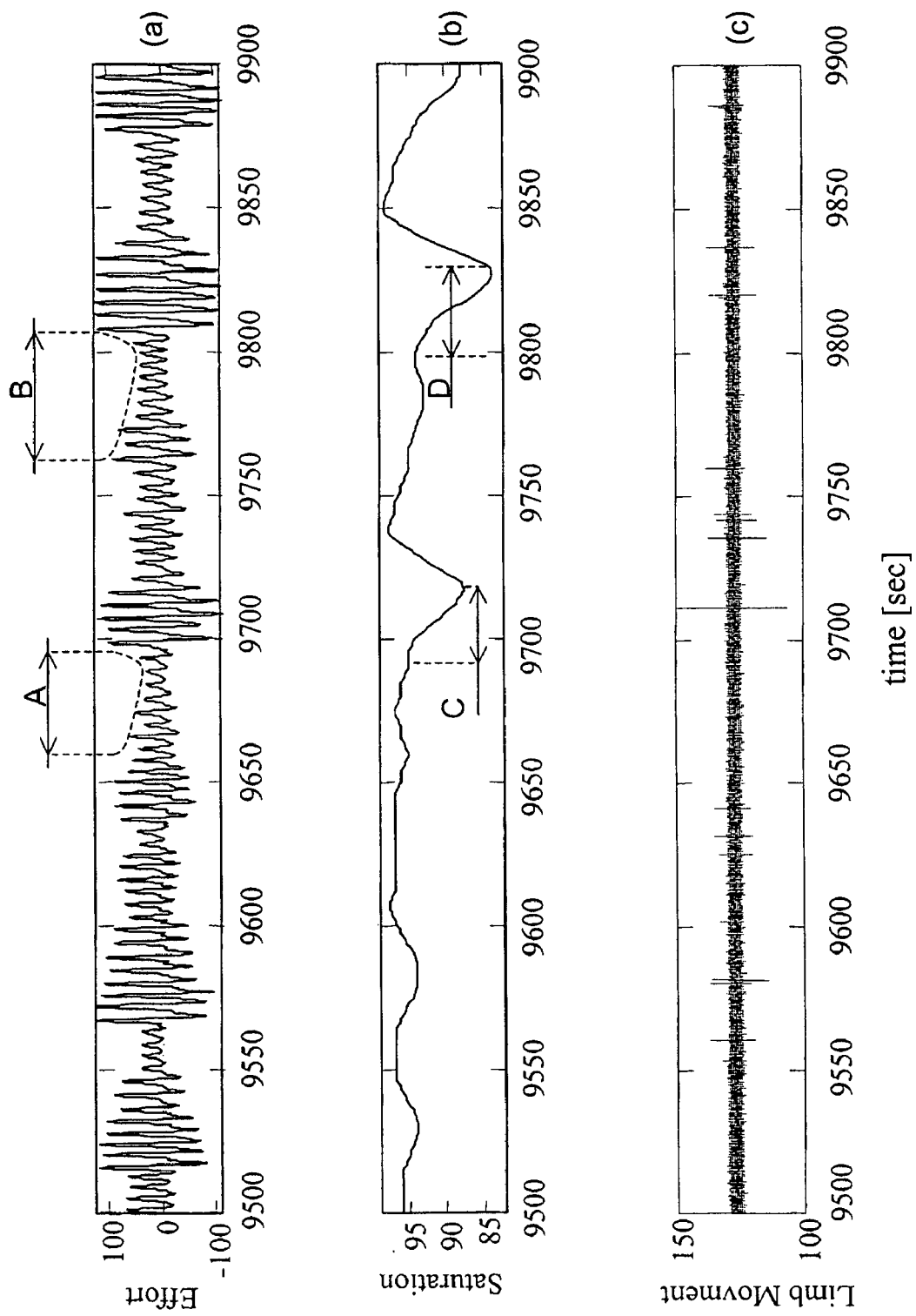
FIGS. 24a and 24b illustrate apnea events and corresponding decrease in Oxygen saturation level, according to a preferred embodiment of the present invention.

FIGS. 24a and 24b (prior art) show exemplary correlation between an effort signal that contains segments in which magnitude decrease of more than 20% and for duration of more than 10 seconds were detected, and Oxygen Saturation. As can be seen in FIG. 24a, significant Respiratory (i.e., effort) deterioration in, e.g., sections A and B (i.e., apneas) caused significant deterioration in the Oxygen Saturation, as reflected in sections C and D, respectively.

Figure 25:
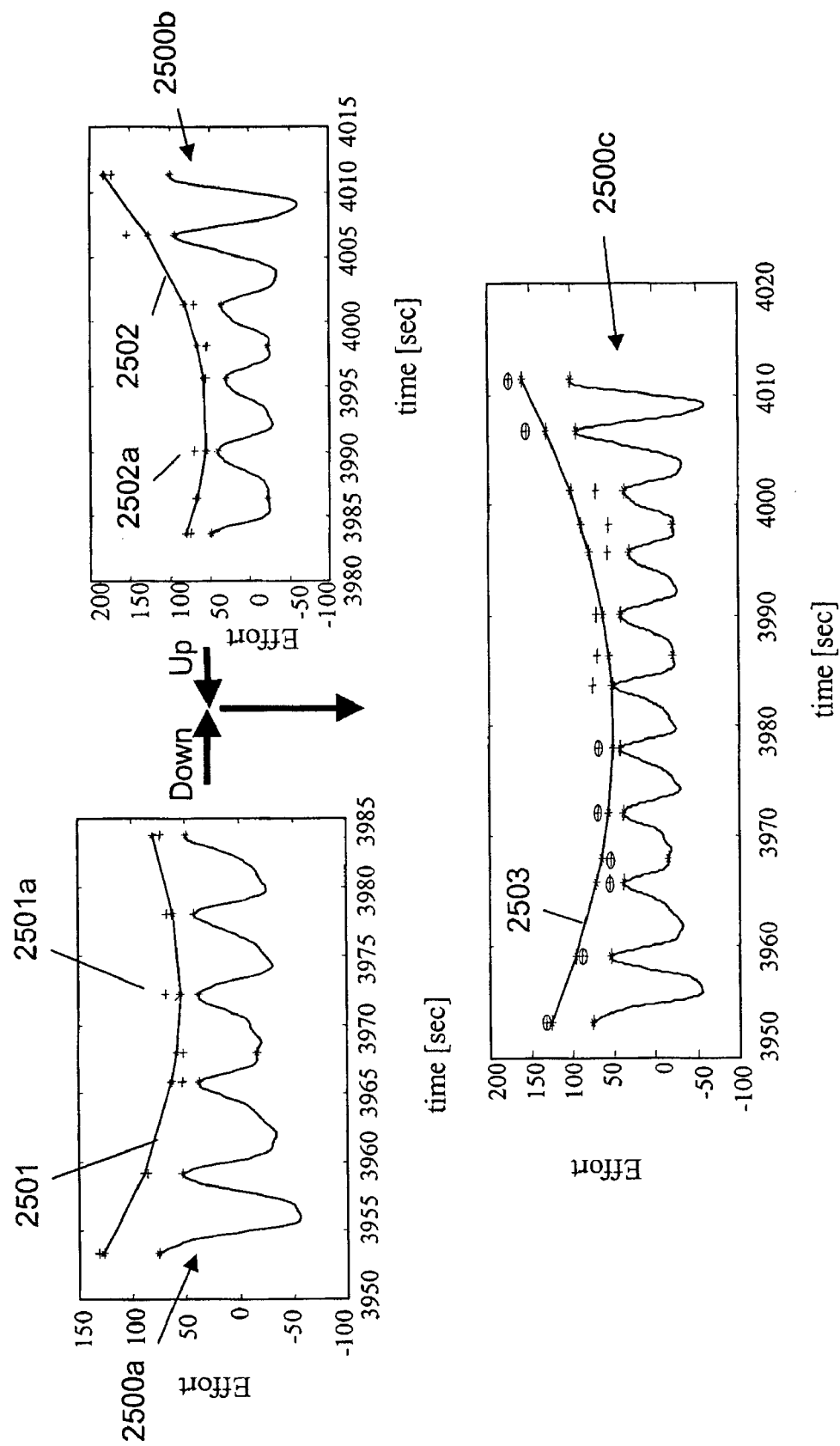
FIG. 25 illustrates adjoining Down parabola and Up parabola to one parabola, according to a preferred embodiment of the present invention.

FIG. 25 schematically illustrates adjoining Downwards-trend segments and Upwards-trend segments, according to a preferred embodiment of the present invention. After finding parabola 2501, which approximates the envelope of segment 2500a, and parabola 2502, which approximates the envelope of segment 2500b, the Segment Combining algorithm (SCA) is employed, after which a new segment 2500c is obtained. The 20% reduction feature is searched for in the new (grand) segment 2500c.

Figure 26:
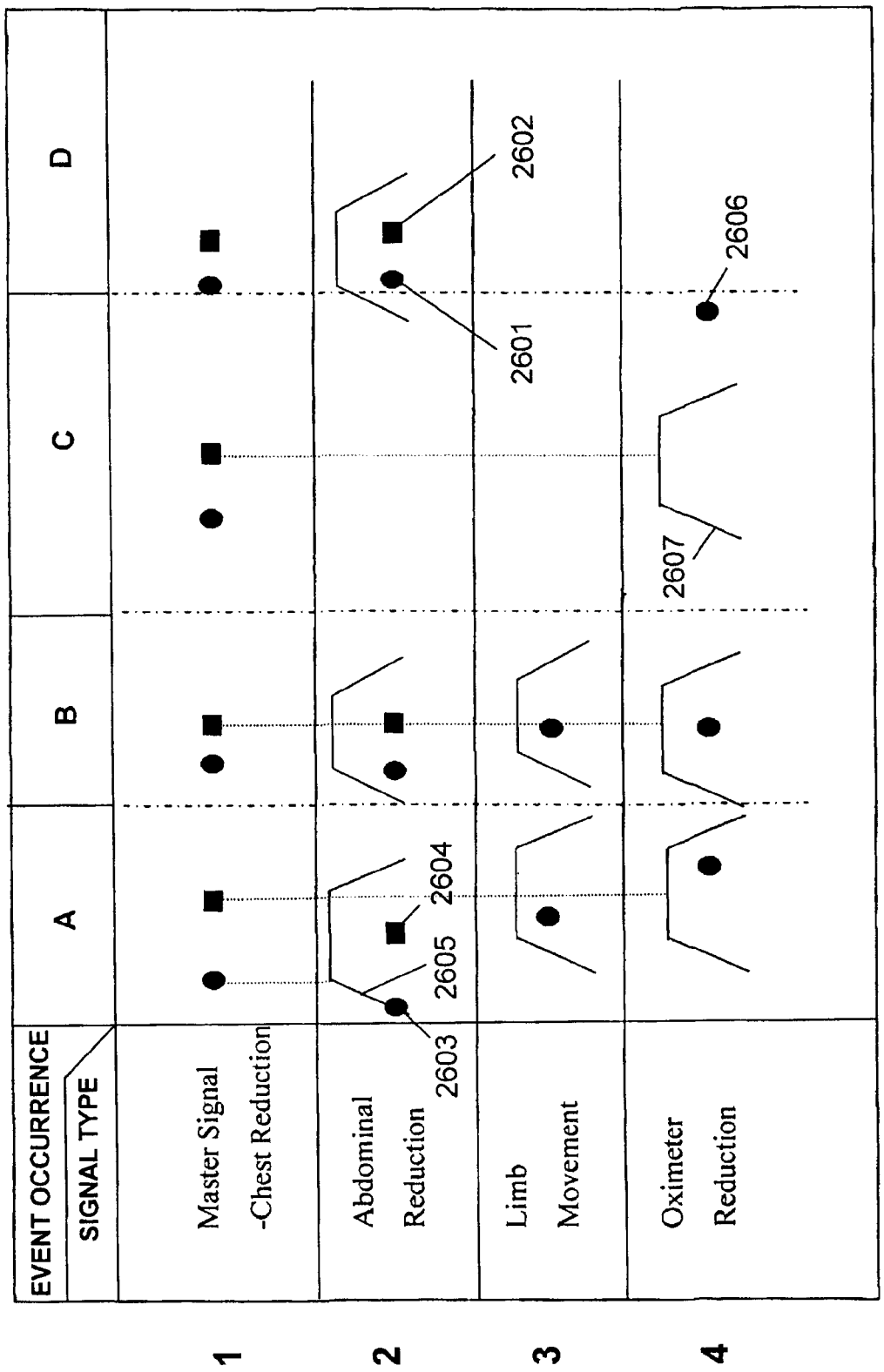
FIG. 26 schematically illustrates exemplary combinations of different events, on which the Decision-Making Algorithm (DMA) is employed, according to a preferred embodiment of the present invention.

FIG. 26 schematically illustrates exemplary combinations of different events, on which the Decision-Making Algorithm (DMA) is employed, according to a preferred embodiment of the present invention. The chest signal reflects the effort signal. The '●' mark indicates the beginning of an event, and the '⊕' mark indicates its ending. In this example, four apnea events have been identified, i.e., 1A, 1B, 1C and 1D. The duration (i.e., time between '●' and corresponding '⊕') of each of the apnea events 1A to 1D is random. Since a decrease in the abdominal effort is expected to overlap the chest effort, a PWW that is associated with the abdominal event is located in relation to the apnea event in a way that the '1.0 probability' (horizontal) line of the abdominal event starts and ends essentially at the starting point (i.e., ●) and ending point (i.e., ⊕) of the apnea, respectively. For example, the starting and ending points of abdominal event 2D (i.e., 2601 and 2602) essentially overlap the starting and ending points of chest event 1D, respectively. Accordingly, abdominal event 2D is assigned the largest weight (i.e., probability value 1). Abdominal event 2A is assigned a smaller weight, because its starting point 2603 is almost outside the limits of the PWW window 2605. Likewise, limb events 3A and 3B, Oximeter events 4A and 4B will be assigned the maximum weight.

Regarding chest event 1C, an Oximeter event 2606 has been detected. However, since it is completely outside PWW 2607, it is assigned a zero weight (value). Namely, Oximeter event 2606 can not be logically related to any other event. Consequently, Oximeter event 2606 is ignored and therefore all D event.

Figure 27:
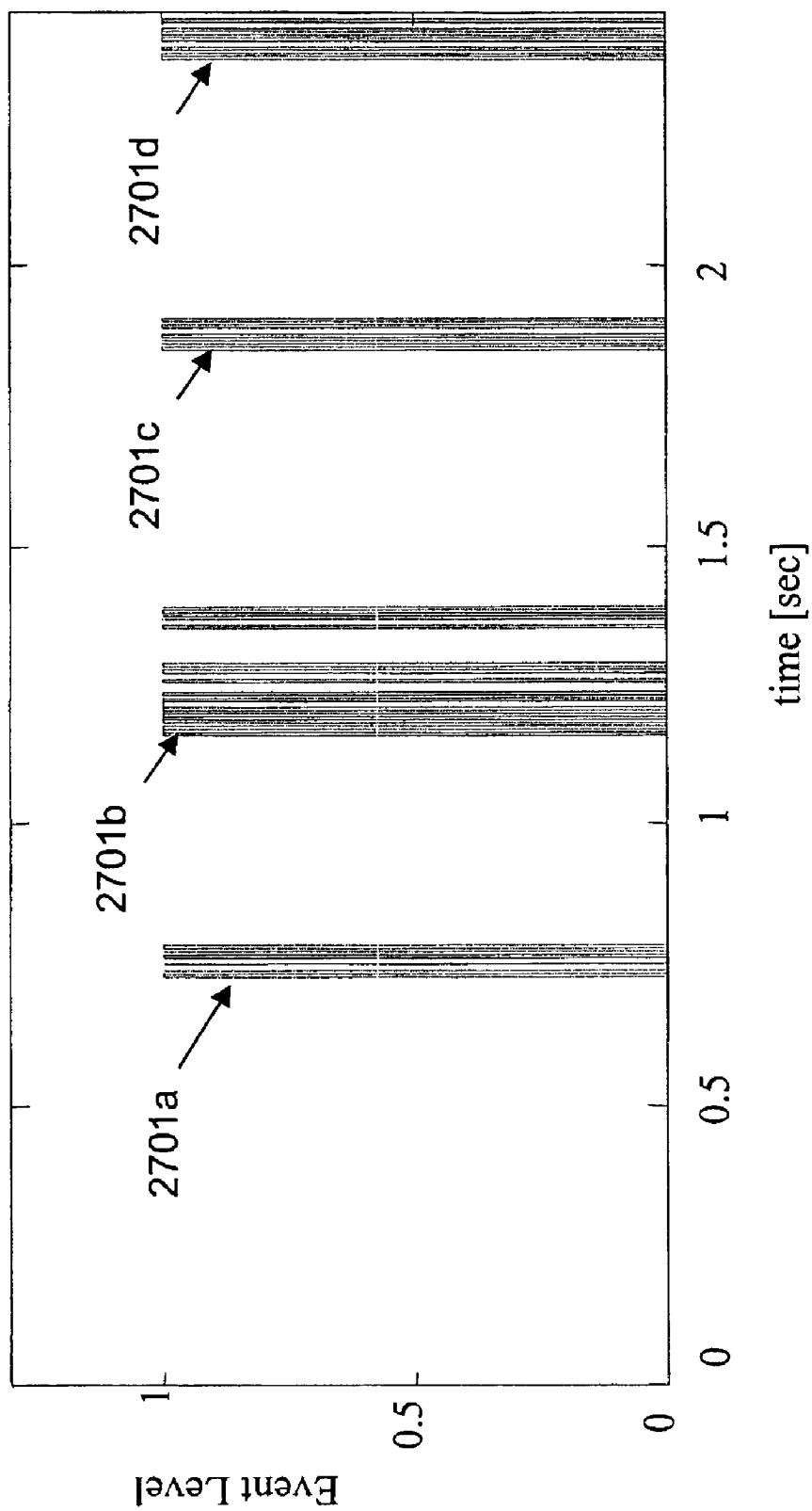
FIG. 27 (prior art) illustrates exemplary resulting apnea events according to a human scorer.

FIG. 27 (prior art) is a graph illustrating resulting apnea events according to human scorer. Reference numerals 2701a to 2701d represent aggregations of apnea events. Because conventional systems are incapable of deciding the probability of occurrence of an apnea event, each event is assigned either a unity value or a zero value.

Figure 28:
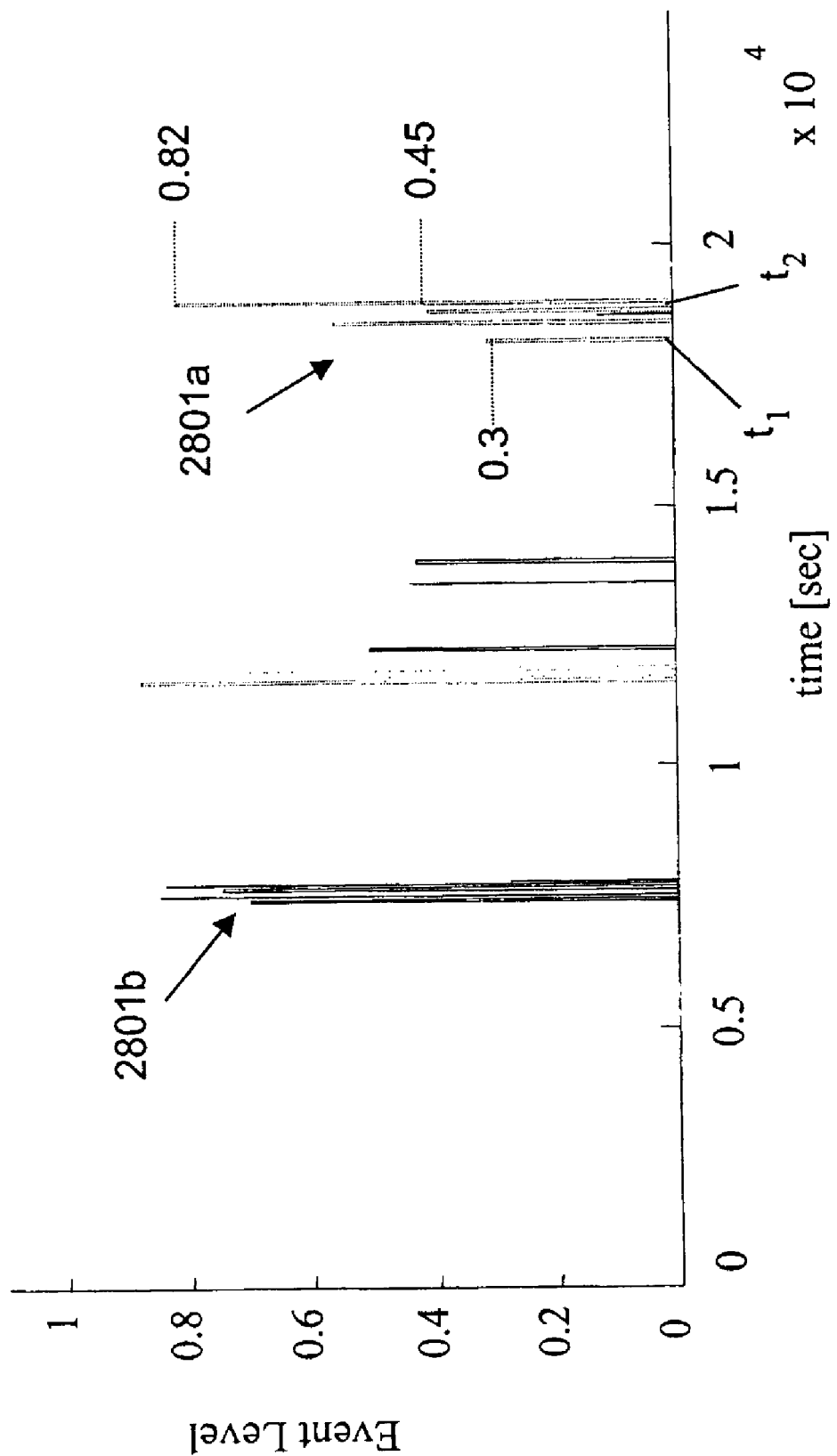
FIG. 28 illustrates exemplary resulting apnea events, according to a preferred embodiment of the present invention.

FIG. 28 is a graph illustrating resulting apnea events, as affected by other factors, according to a preferred embodiment of the present invention. Reference numeral 2801a is an aggregation of several events that are suspected as apneas. In these aggregated events, additional two types of events were also considered in order to evaluate the probability of an event being an apnea. One type of these events is the Oxygen saturation level in the blood (i.e., as measured by the Oximeter channel), and the second type is the probability that the monitored person was sleeping (i.e., measured by the EEG signal). For example, at time t1 the resulting probability for an apnea is 0.3. A low-probability apnea may be obtained as a result of having: (1) very low probability value that the detected corresponding decrease in the Oxygen saturation level is associated with an apnea, and/or (2) very low probability value that the monitored person was fully asleep. At time t2, however, the resulting probability of an apnea is much higher (i.e., 0.82), because at that time the probability that the monitored person was sleeping was relatively high, and/or the corresponding decrease in Oxygen saturation level was more closely related to the event that was suspected as apnea.

Reference numeral 2801b refers to another aggregation of events. In these aggregated events, only one additional type of event was also considered in order to evaluate the probability of an event being an apnea, namely, the Oxygen saturation level in the blood. In general, in this aggregation, apnea events were assigned relatively high probability values.

In general, the more event types (e.g., Oxygen saturation, Sleep status) are considered when evaluating the probability of an apnea, the more 'realistic' is the decision regarding such apnea.

Figure 29:
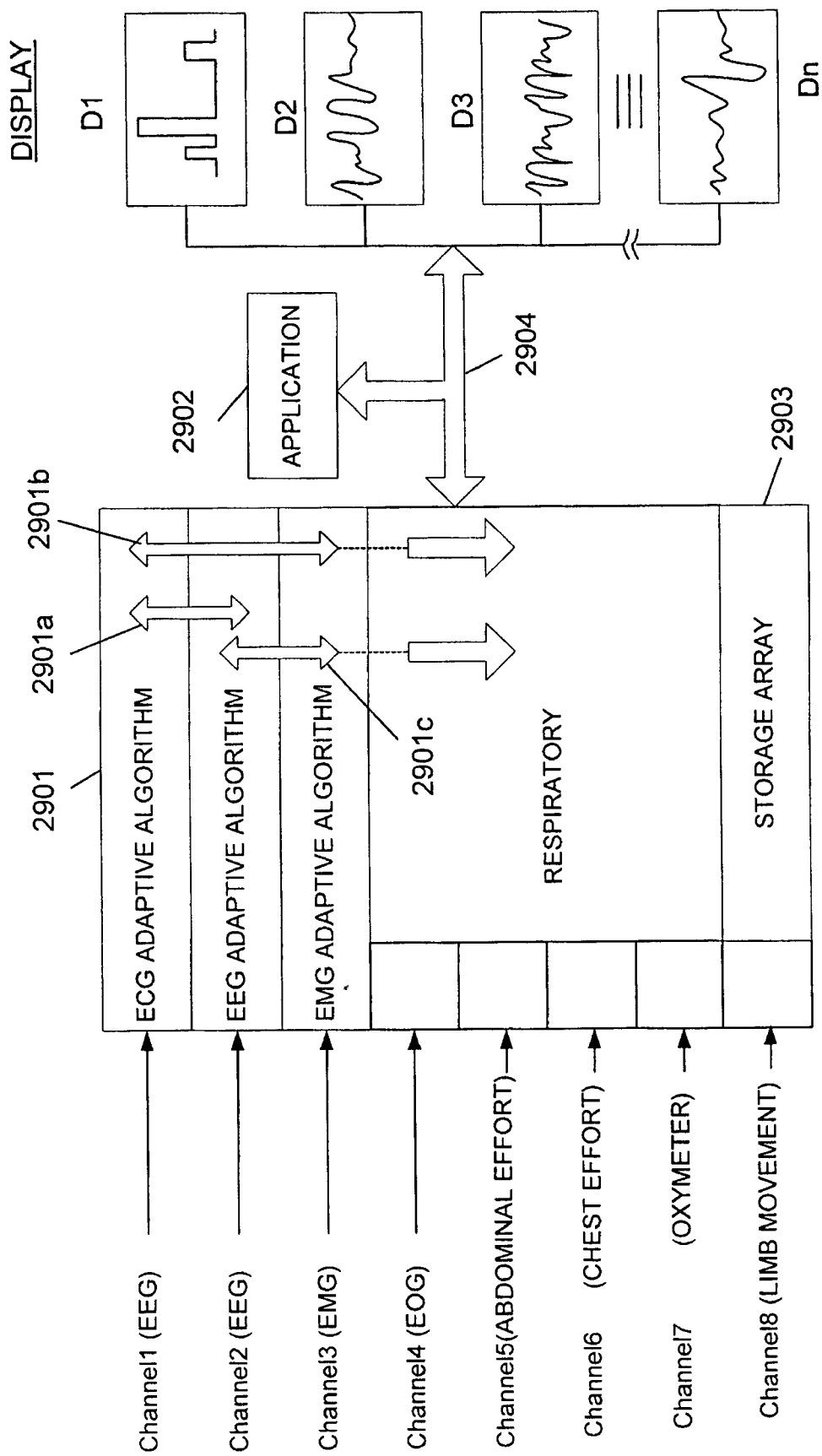
FIG. 29 schematically illustrates the general functionality of the system, according to a preferred embodiment of the present invention.

FIG. 29 schematically illustrates the functionality and layout of the system, according to a preferred embodiment of the present invention. Channels 1 to 7 are associated with ECG signal, EEG signal, EMG signal and Respiratory signals—abdominal effort signal, chest effort signal and Oxygen saturation signal, respectively. Samples of these signals (not shown) are input into a computer, which contains the software algorithms 2901 that are required for taking corresponding decisions based on the processed samples. The system is capable of learning individual heartbeat behavior, as reflected by the corresponding ECG signal, as well as sleep behavior, as reflected in the corresponding EEG signal. Moreover, the system is also capable of learning movements that characterize the monitored person, thereby allowing distinguishing normal movements from random movements, which are usually regarded as noise. The learning capabilities of the disclosed system allow relating to each other the ECG, EEG, EMG and the Respiratory signals (2901a to 2901c), which allow to obtain more accurate and enhanced decisions. For example, regarding Respiratory disorders, an accurate decision may be obtained after considering also the corresponding sleep stage (i.e., EEG signal) of the person.

Storage array 2903 is utilized in general for storing several types of data: (1) samples of the raw signals (e.g., ECG), (2) initial parameters, for allowing the system to start its operation whenever a person is connected to the system, (3) processed data, which is associated with the system learning process of a monitored person.

Displays D1 to Dn may display various specific physiological data of interest, on request, according to application layer 2902, such as time-wise events and/or frequency-wise events. For example, display D1 may introduce sleep stages, D2 heartbeats, D3 Respiratory signal, etc. If a clinician wishes so, a display may introduce him with raw data of desired type(s) (e.g., ECG).

Software 2901, D1 to Dn and application layer 2902 may reside within same computer or in different locations, in which case they may communicate with each other over a data network 2904, such as the Internet, LAN etc.

Figure 30:
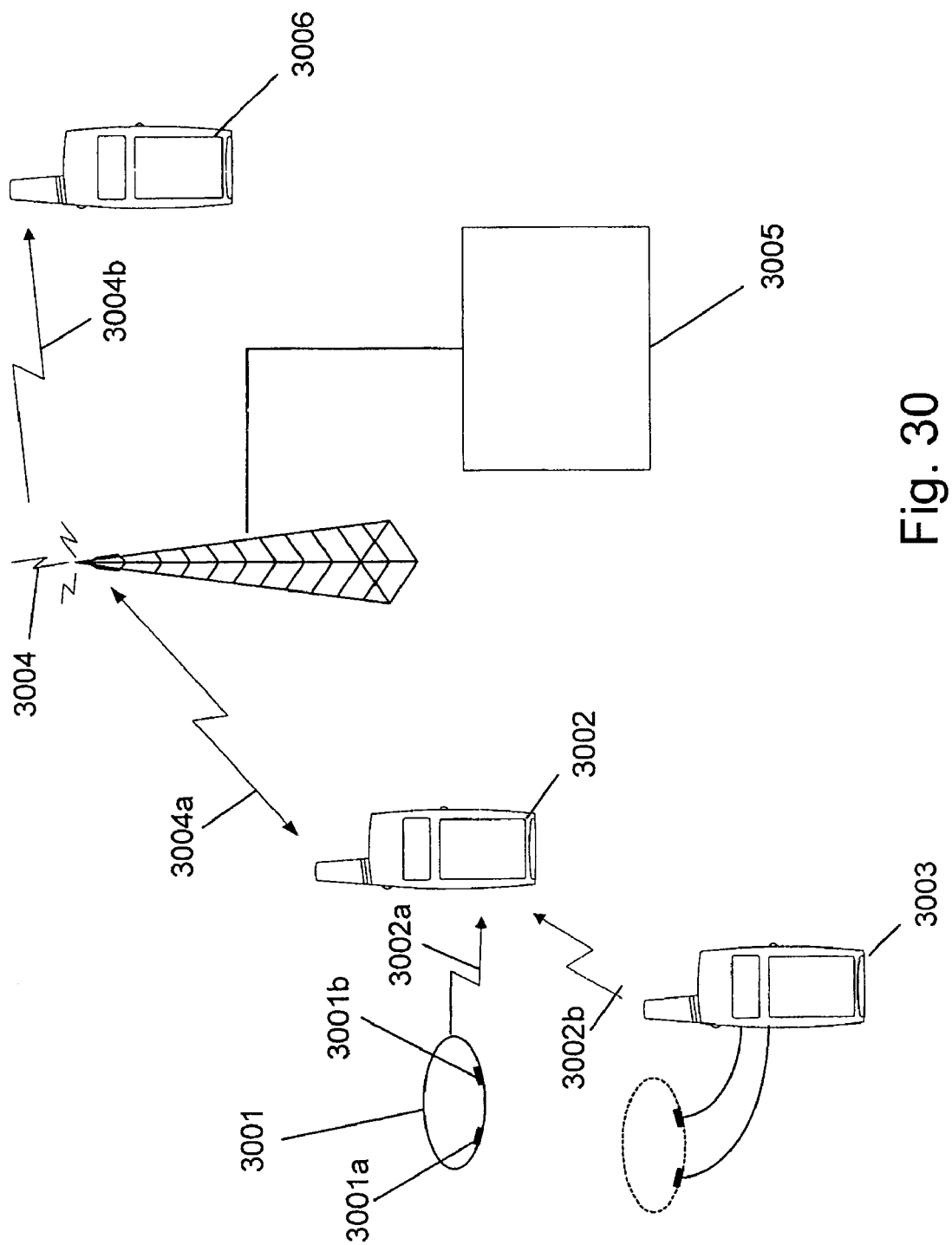
FIG. 30 schematically illustrates a Cellular-phone-based Remote Monitoring System (CRMS), according to one embodiment of the present invention.

FIG. 30 schematically illustrates a Cellular-phone-based Remote Monitoring System (CRMS), according to a preferred embodiment of the present invention. Stripe 3001, which includes, e.g., electrodes 3001a and 3001b, is placed on a monitored person (not shown). Electrodes 3001a and 3001b include transmitters (not shown) for transmitting, over wireless communication channel 3002a, relevant signals (e.g., ECG, EEG) to cellular phone 3002, which is located close enough to the transmitting antenna(s), to allow good reception of these signals. Alternatively, electrodes 3001a and 3001b are connected to interface 3003, which transmits these signals to cellular phone 3002 on wireless communication channel 3002b. Transmissions over wireless communication channels 3002a and 3002b may be carried out by utilizing the Wireless Application Protocol (WAP) standard.

Cellular phone 3002 contains software, the task of which is to carry out a preliminary classification process of the signals, i.e., for identify typical and irregular shapes in these signals, and transmit the latter signals to cellular base-station 3004, in which a dedicated server 3005 resides. Server 3005 contains software, the task of which is to carry out a full evaluation of the received signals, essentially as described above. Whenever a decision is made in server 3005, regarding heartbeat (or heartbeat rate) disorder, and problematic segments (i.e., of the types described above), the corresponding data is transmitted from base-station 3004 to clinician's cellular phone 3006, and displayed on its display in the form of a graph or otherwise.

There are several drugs that only a qualified physician can authorize their usage. However, a qualified physician is rarely present at a scene wherein a person urgently needs such a drug, and a considerable amount of time may be lost until the person is brought to such qualified physician (e.g., in a hospital). In some cases, the time lost may be critical to the life of the person.

The CRMS system solves the latter described problem by allowing paramedical staff to administer drugs to a person while taking orders from a physician that is located far away from the paramedical staff. According to the invention, upon arrival at a scene, wherein a person is found to be in medical critical situation, an, e.g., ambulance staff attaches the electrodes to the person, and the relevant data is received by a physician's cellular phone, essentially as described above. Upon receiving the latter data, the physician orders the paramedical staff to administer to the person a certain dosage of corresponding drug, while the person is being monitored. As the person's physiological status changes as a reaction to the drug being administered to him, and the data appearing on the physician cellular phone's display changes accordingly and 'on-line', the physician may give the paramedical staff correcting orders (i.e., by utilizing a different, or same, cellular phone), until the status of the person stabilizes or improves, whichever the physician's decision is.

Of course, the cellular phone system could be replace by other types of (data) networks, such as the Internet, a Local Area Network (LAN), a Wide Area Network (WAN) etc.

Figure 31:
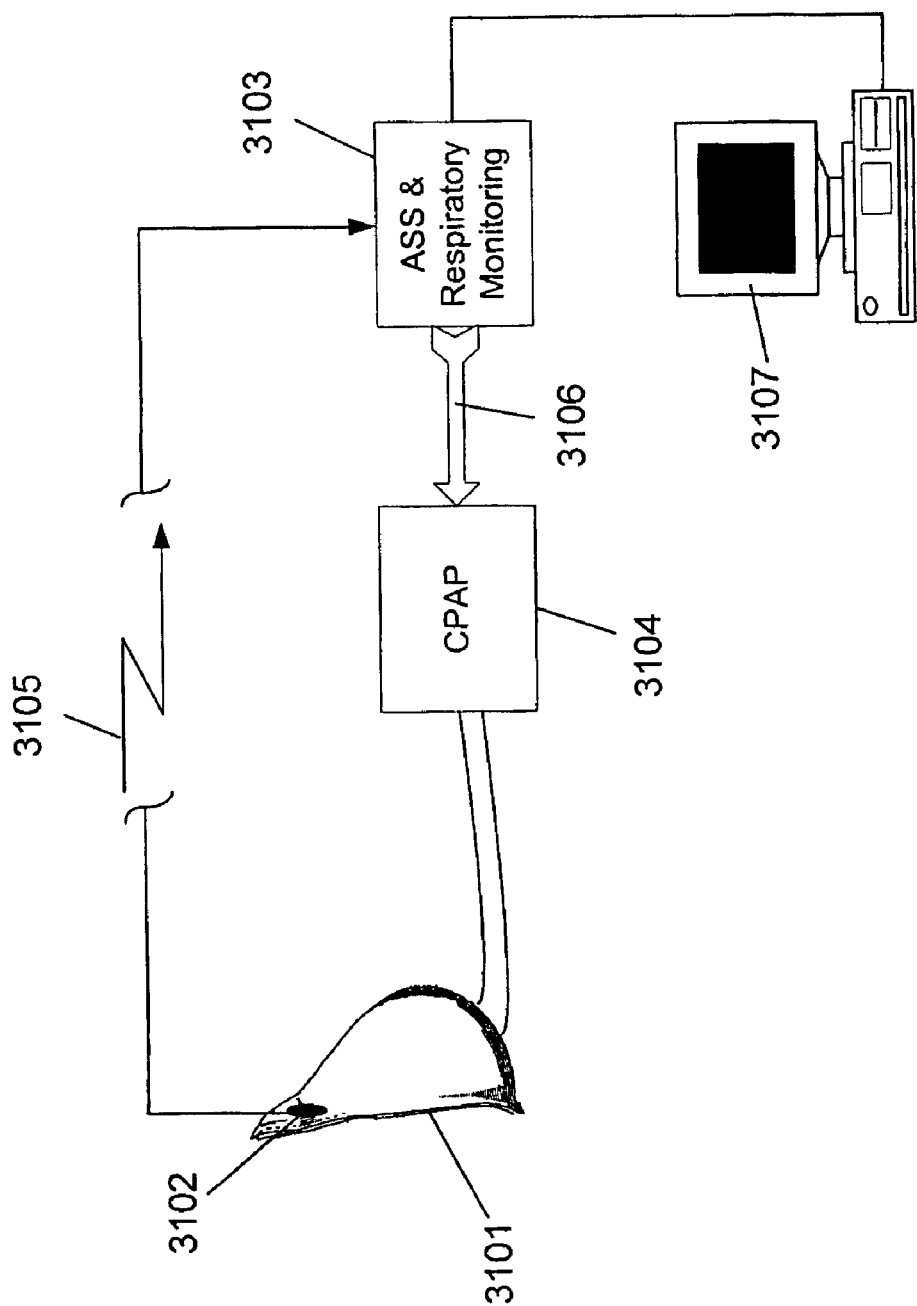
FIG. 31 schematically illustrates utilizing the Automatic Sleep Stage (ASS) system with combination with a Continuous Positive Airway Pressure (CPAP) system, according to a preferred embodiment of the present invention.

FIG. 31 schematically illustrates utilizing the Automatic Sleep Stage (ASS) and Respiratory system with combination with a Continuous Positive Airway Pressure (CPAP) system, according to a preferred embodiment of the present invention. The CPAP system is the most common treatment for sleep apnea. The patient wears mask 3101 over his nose during his sleep, for allowing controllable CPAP system 3104 to force air through his nasal cavity to provide a pneumatic splint that prevents the upper airway from obstructing. The air pressure is adjusted so that it is just enough to prevent the throat from collapsing during sleep. Electrode 3102 is mounted in mask 3101 in such a way, that it is tightly attached to the relevant spot on the face of the monitored person to allow picking up the required signal(s). Electrode 3102 transmits (3105) signal(s) to ASS & Respiratory system 3103, which processes the signal(s) essentially at the way described above. Whenever required, system 3103 sends a signal to CPAP system, for causing it to change the pressure of the air that is provided to mask 3101. The latter signal is associated with the current sleep stage and Respiratory condition as detected by system 3103.

Conventional CPAP systems (i.e., that do not include ASS systems), have several drawbacks: (1) apnea events may return whenever the CPAP is used improperly, which is normally the case because conventional CPAP systems are poorly controlled, or not controlled at all, by physiological feedback. Therefore, these systems output a constant and continuous pressure, or vary the pressure to coincide with the person's breathing pattern, or start with low pressure, after which the pressure is gradually increased. Pressure is constantly provided to the person's nasal cavity causing to side effects, such as nasal and facial skin irritations and drying, abdominal bloating, mask leaks, sore eyes, breathing interference and headaches. From technical point of view, conventional CPAP systems are inefficient, because they supply, at different periods, air that is not beneficial to the patient.

Utilizing ASS & Respiratory system 3103 in combination with CPAP system 3104 is advantageous because system 3103 is capable to foresee an apnea event, in which case it causes the CPAP to provide the patient with the exact air pressure at the right time. In cases where system 3103 does not foresee an apnea, no pressure is employed by the CPAP system. Therefore, affiliation of system 3103 with CPAP systems greatly improves the performance and efficiency of the CPAP systems, and the side effects are significantly reduced. Due to system 3103 adaptation capability, to adjust (i.e., by learning) itself to the monitored patient, the CPAP also adapts itself to the monitored patient. Monitoring unit 3107 allows local, or remote, supervision of a clinician, which might be passive, due to the 'automatic nature' of the system, or active, due to, e.g., emergency state.

Figure 32:
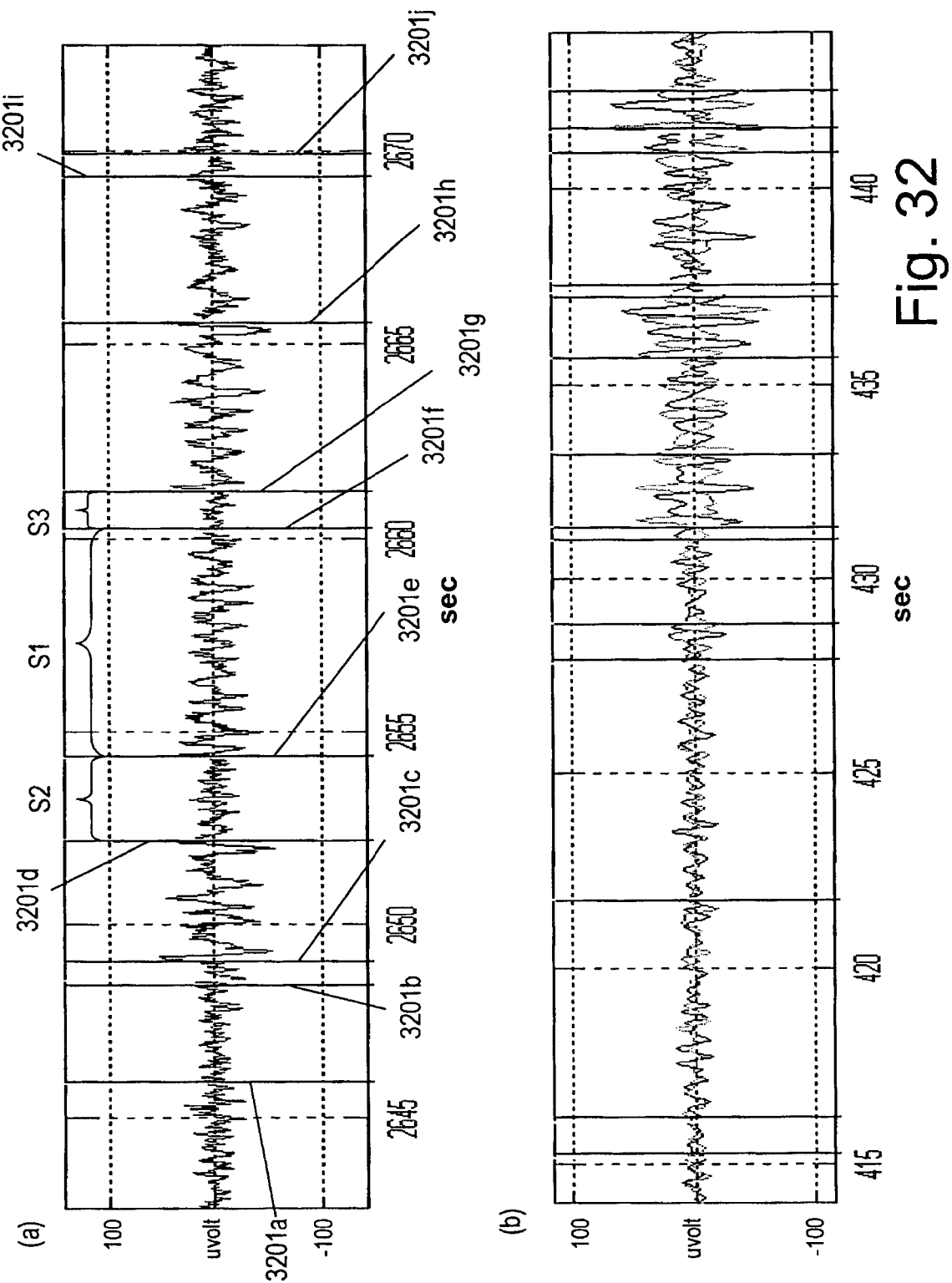
FIGS. 32a and 32b illustrate exemplary results of the adaptive segmentation of EEG and EOG signals, respectively, according to a preferred embodiment of the present invention.

FIGS. 32a and 32b illustrates exemplary results of the adaptive segmentation of EEG and EOG signals, respectively, according to a preferred embodiment of the present invention. In FIG. 32a, vertical lines 3201a to 3202i indicate the boundaries of the corresponding quasi-stationary segments, which were calculated by the adaptive algorithm as described above. As might be appreciated, each quasi-stationary segment has a unique shape, which distinguishes it from its adjacent quasi-stationary segments. For example, segment S1 differs in shape from segments S2 and S3. Likewise in FIG. 32b, wherein EOG quasi-stationary segments were found in the same way as the EEG quasi-stationary segments.

Figure 33:
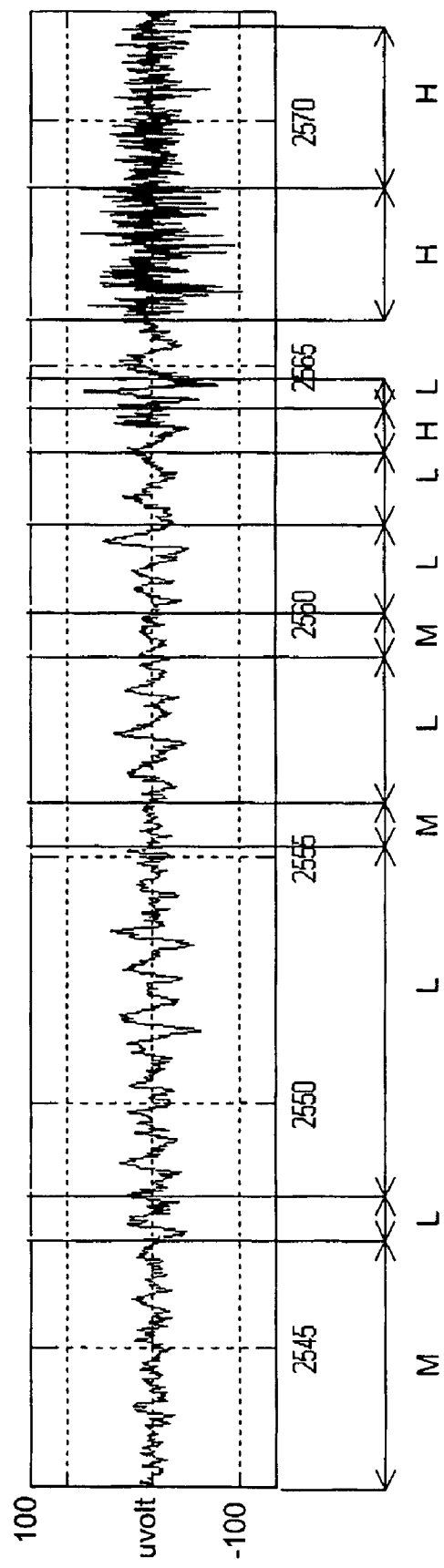
FIG. 33 illustrates an example for associating quasi-stationary segments with one of the three frequency groups, according to a preferred embodiment of the present invention.

FIG. 33 illustrates an example for associating quasi-stationary segments with one of the three frequency groups, according to a preferred embodiment of the present invention. After extracting the time and frequency features from the quasi-stationary segments, each quasi-stationary segment is associated with a corresponding frequency group. For example, quasi-stationary segments indicated by 'H' were found to contain relatively high-frequency content. Consequently, these segments would be associated with the FFG. Likewise, quasi-stationary segments indicated by 'M' would be associated with the MFG, and quasi-stationary segments indicated by 'L' would be associated with the SFG.

Figure 34:
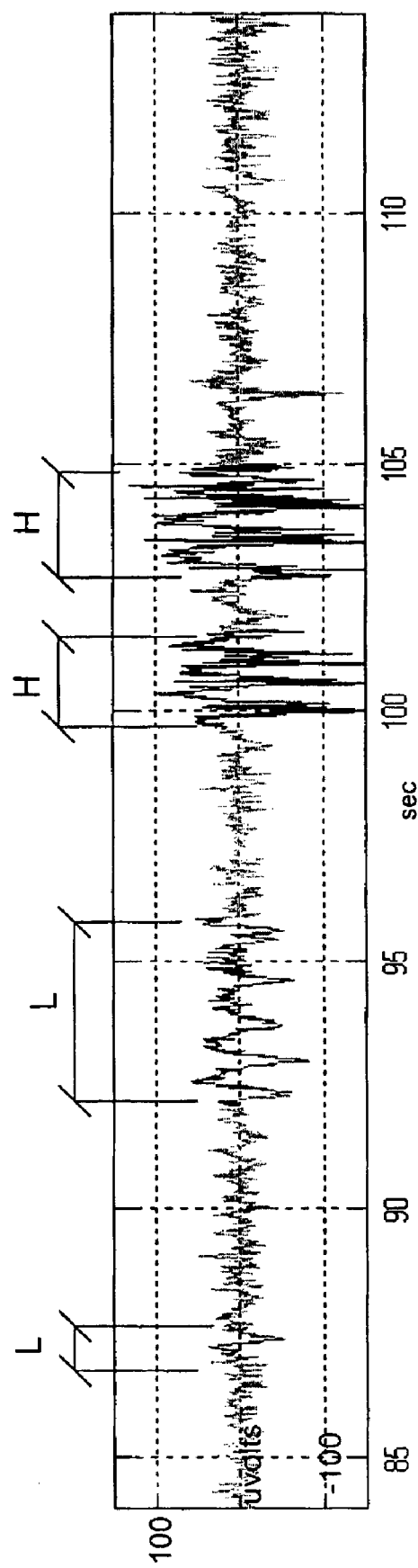
FIG. 34 illustrates detection of special events, according to a preferred embodiment of the present invention.

FIG. 34 illustrates detection of special events, according to a preferred embodiment of the present invention. Special events are identified by their low, or high, frequency content and by their temporal shape. Segments marked with 'L' are low-frequency events, and segments marked with 'H' are high-frequency events. Special events are not utilized in the cluster analysis.

Figure 35:
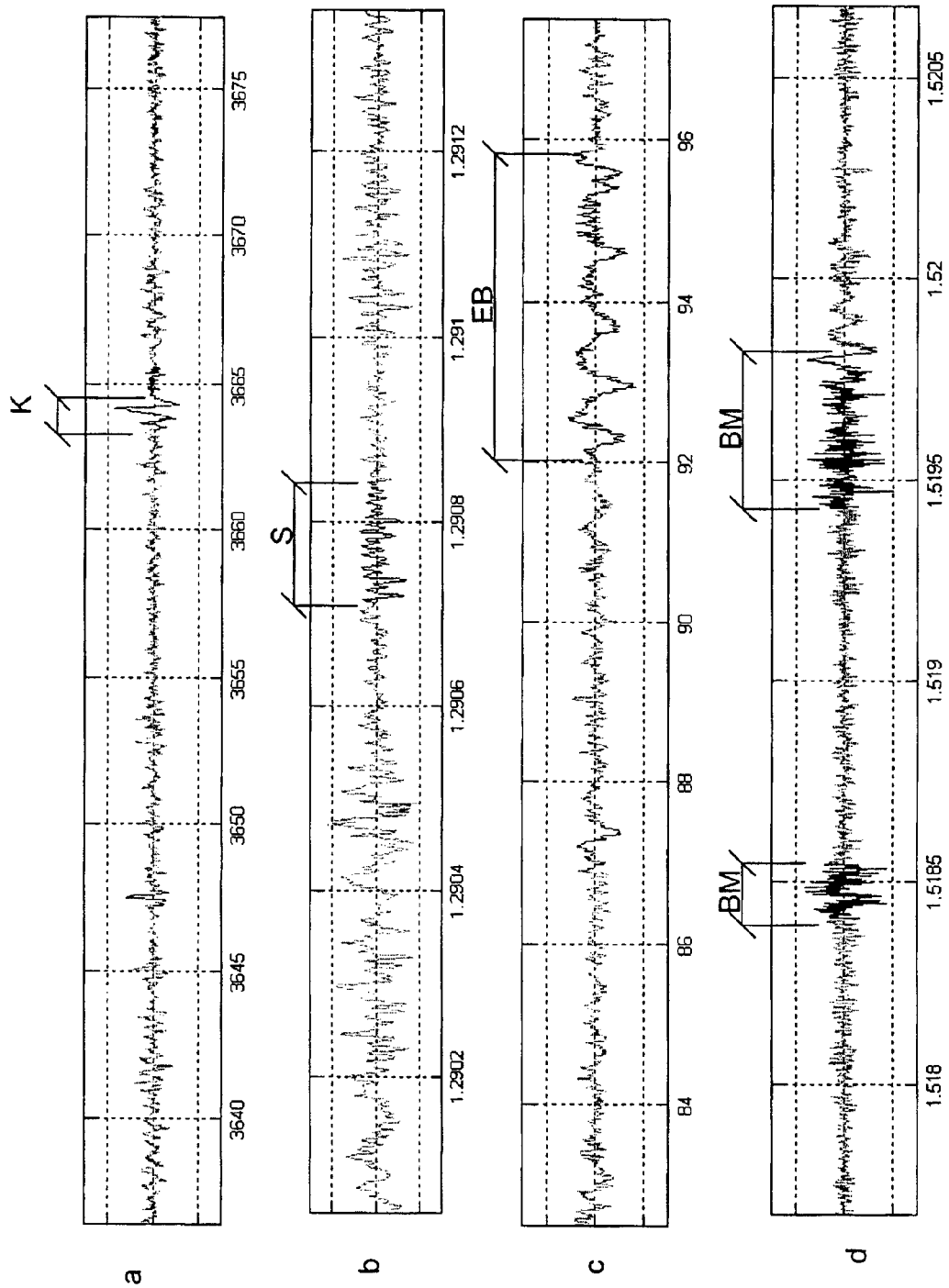
FIGS. 35a to 35d illustrate exemplary classification of special events, according to a preferred embodiment of the present invention.

FIGS. 35a to 35d illustrate exemplary classification of special events, according to a preferred embodiment of the present invention. In FIG. 35a, typical K-complex is shown (marked with 'K'). In FIG. 35b, typical spindle is shown (marked with 'S'). In FIG. 35c, typical eye-blink is shown (marked with 'EB'). In FIG. 35d, typical body movement is shown (marked with 'BM').

Figure 36:
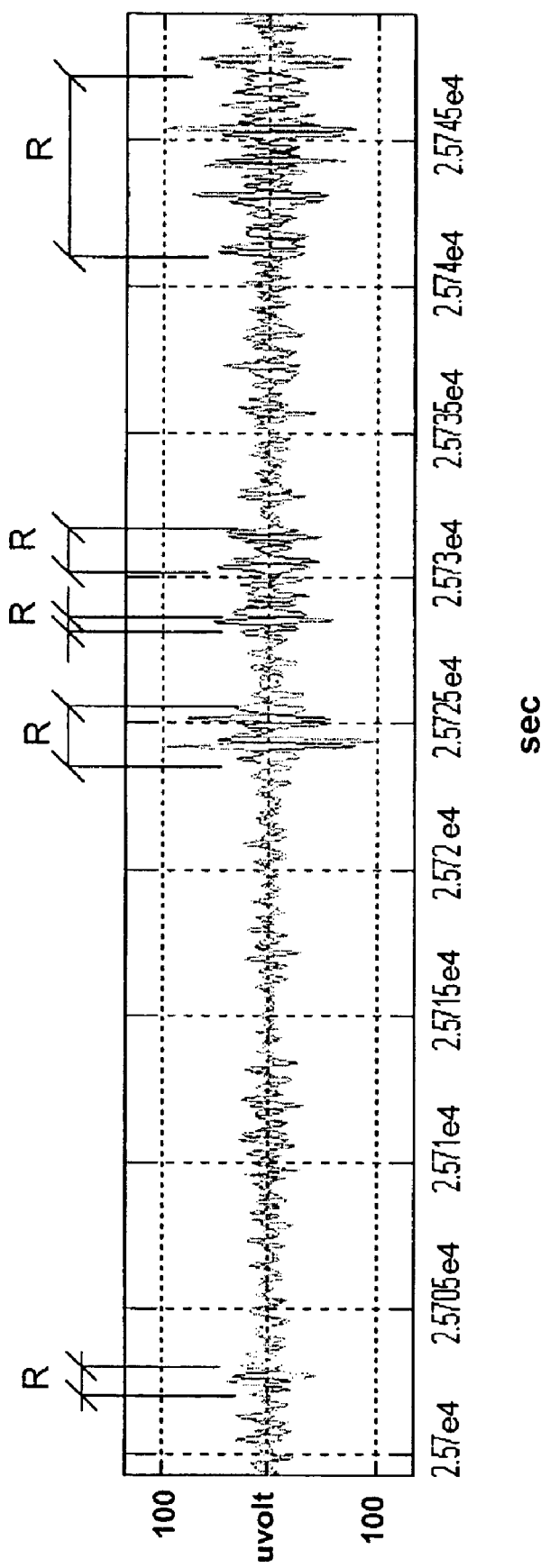
FIG. 36 illustrate exemplary REM events, according to a preferred embodiment of the present invention.

FIG. 36 illustrate exemplary REM events, according to a preferred embodiment of the present invention. REM events are detected only if the ASS system is configured to handle EOG signal. typical REM events are marked (in FIG. 36) with 'R'.

Figure 37:
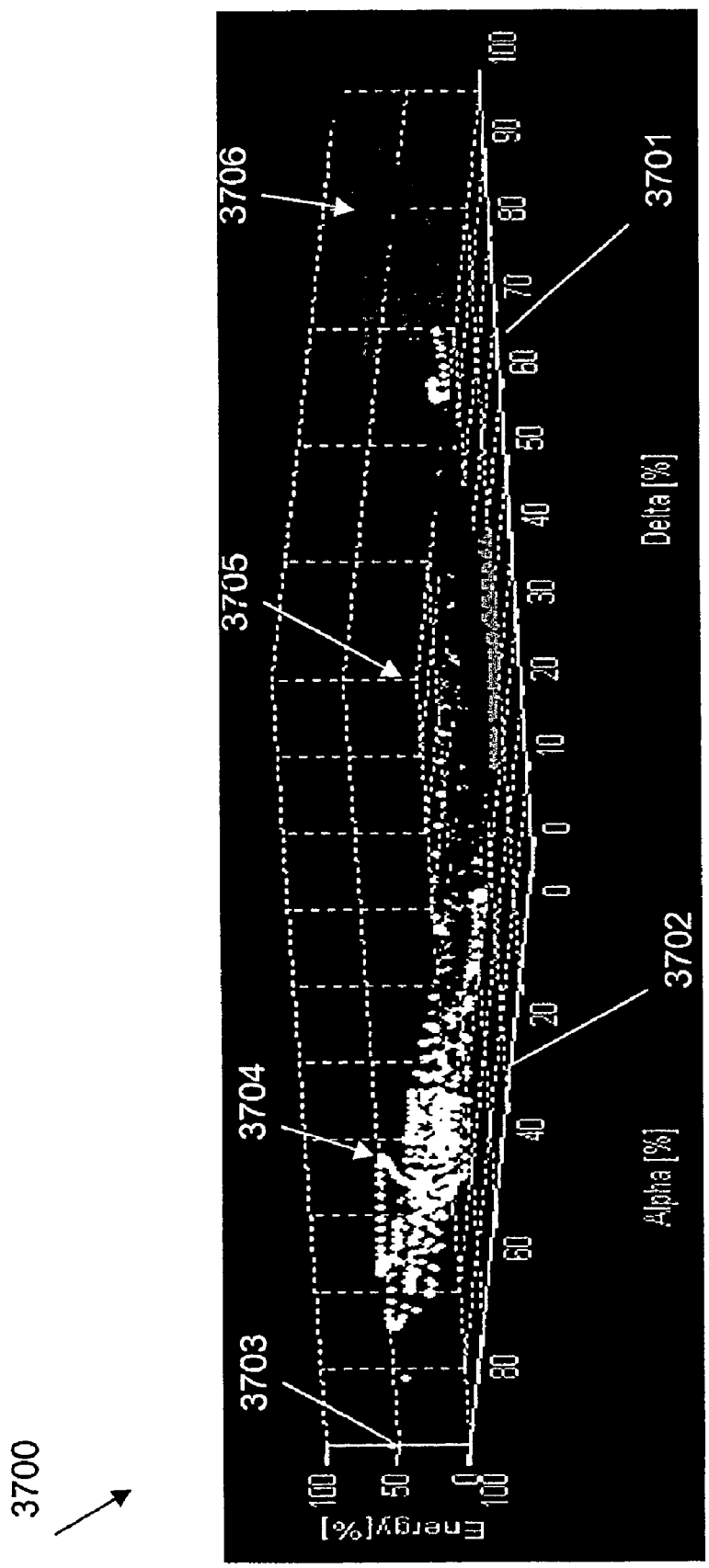
FIG. 37 illustrates exemplary clusters, according to a preferred embodiment of the present invention.

FIG. 37 illustrates exemplary clusters, according to a preferred embodiment of the present invention. Graph 3700 shows typical clustering of quasi-stationary segments features as were detected in the whole night. Axis 3701 and axis 3702 describe the relative energy (between 0% and 100%) of Delta-wave or a Alpha-wave, respectively. Axis 3703 describes the total energy of the corresponding quasi-stationary segment. White colored cluster 3704 describes every quasi-stationary segment that was associated with the FFG group. White colored cluster 3704 describes every quasi-stationary segment that was associated with the FFG group. Gray colored cluster 3705 describes every quasi-stationary segment that was associated with the MFG group, and the black colored cluster 3706 describes every quasi-stationary segment that was associated with the SFG group.

Figure 38:
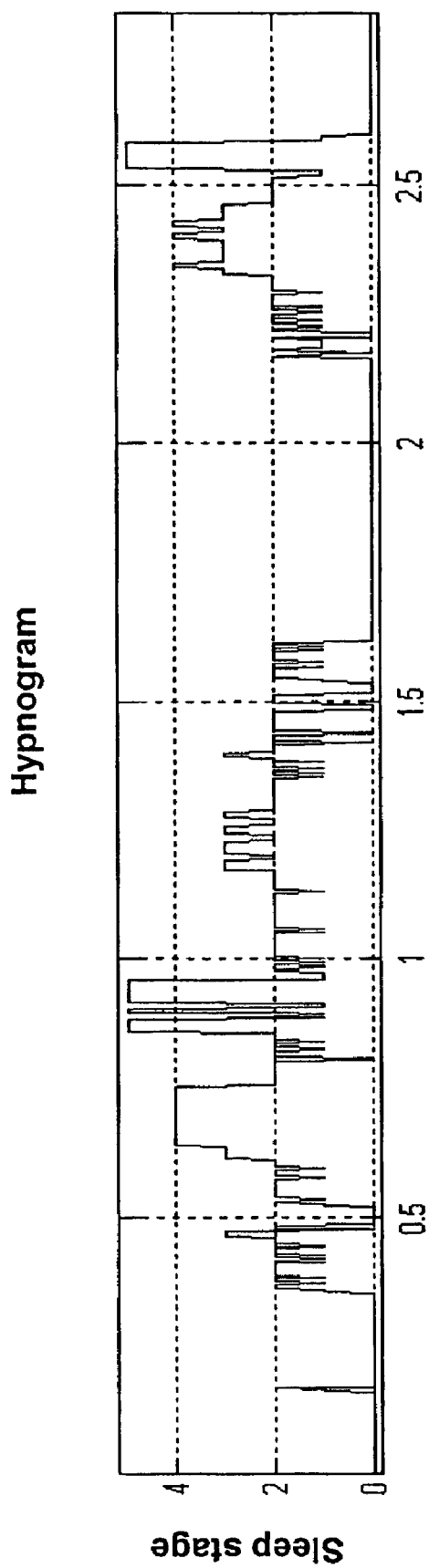
FIG. 38 depicts the resulting exemplary hypnogram, which describes the relevant sleep stages, according to a preferred embodiment of the present invention.

Each cluster (i.e., 3704, 3705 and 3706) is characterized by a Gaussian Probability Function (GPF, not shown). Each frequency group (i.e., cluster) is averaged per 30-second time-interval, resulting in a membership value (i.e., between 0.0 and 1.0). Accordingly, each 30-second time-interval is represented by corresponding three membership values, each of which represents the probability of a person being in a corresponding sleep stage. The actual sleep stage (i.e., per specific time-interval) is obtained by employing the R&K set of rules on the corresponding membership values and on the relevant detected special events. FIG. 38 depicts the resulting hypnogram, which describes the relevant sleep stages.

Figure 39:
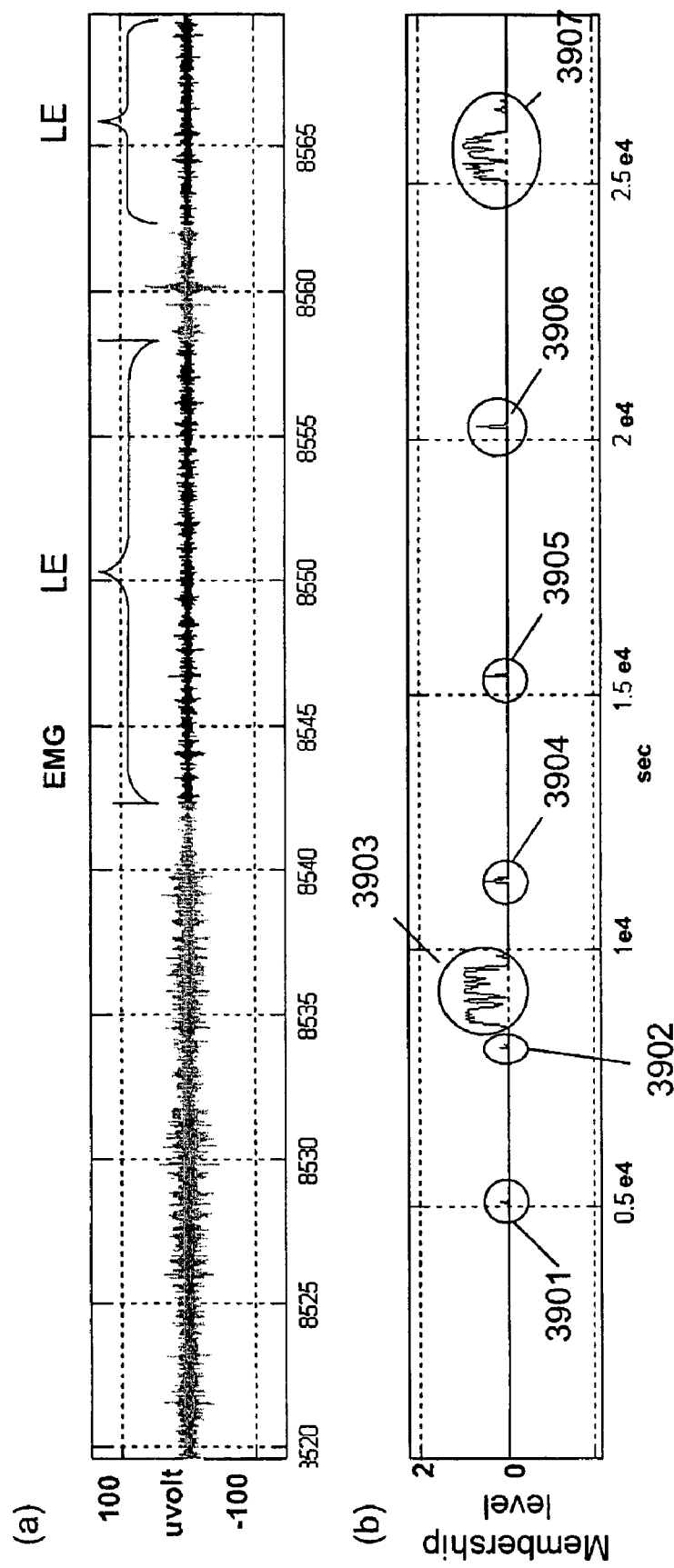
FIGS. 39a and 39b illustrate exemplary detection of low energy portions in the EMG signal, according to a preferred embodiment of the present invention.

FIGS. 39a and 39b illustrate exemplary detection of low energy portions in the EMG signal, according to a preferred embodiment of the present invention. Sections denoted LE represent the low energy portions of the EMG signal. In FIG. 39b, reference numerals 3901 to 3907 represent the membership values of the EMG signal.

Figure 40:
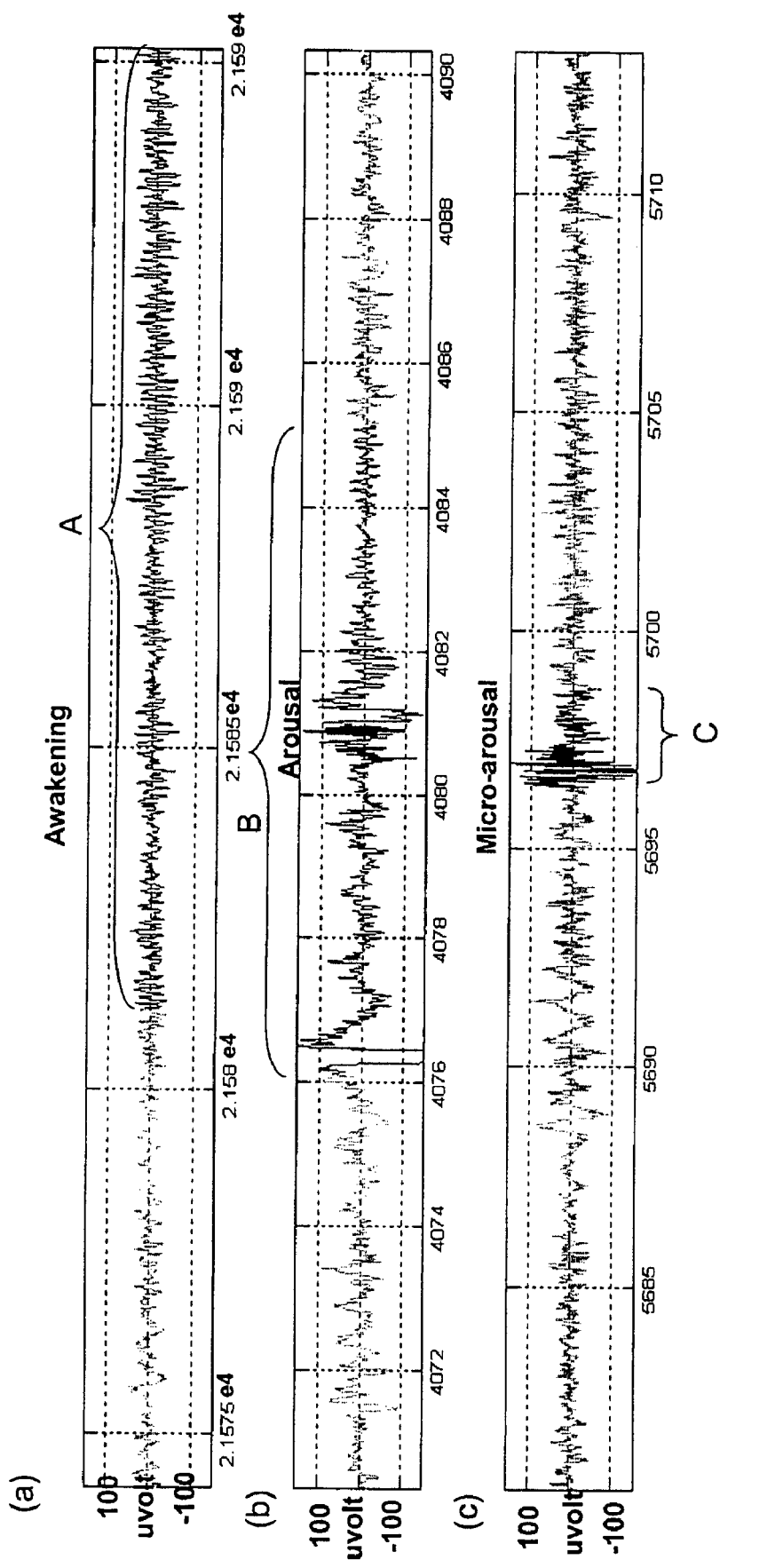
FIGS. 40a to 40c illustrate typical Awakening, Arousal and Micro-Arousal stages, according to a preferred embodiment of the present invention.

FIGS. 40a to 40c illustrate typical Awakening, Arousal and Micro-Arousal stages, according to a preferred embodiment of the present invention. 'A' (In FIG. 40a), 'B' (In FIG. 40b) and 'C' (In FIG. 40c) denote the Awakening, Arousal and Micro-Arousal stages, respectively.

The above examples and description have of course been provided only for the purpose of illustration, and are not intended to limit the invention in any way. As will be appreciated by the skilled person, the invention can be carried out in a great variety of ways, employing more than one technique from those described above, all without exceeding the scope of the invention.

What is claimed is:

1. A method for sleep diagnosis, comprising:
   using one or more sensors, receiving biomedical signals from a sleeping patient over a given time period;
   using a processor, extracting features from the biomedical signals and grouping the features into multiple clusters;
   using the processor, assigning respective vectors of membership values to a plurality of intervals within the given time period, each membership value indicating a degree of association between the biomedical signals in a corresponding interval and a respective cluster among the multiple clusters; and
   with the processor, determining a condition of the patient responsively to the vectors using a state machine model which comprises machine states corresponding to physiological states of the patient.

2. The method according to claim 1, wherein evaluating the condition comprises classifying sleep stages of the patient based on the vectors.

3. The method according to claim 1, wherein receiving the biomedical signals comprises receiving electroencephalogram (EEG) signals.

4. The method according to claim 1, wherein extracting the features comprises adaptively segmenting the biomedical signals into a sequence of segments, and determining the features of each of the segments.

5. The method according to claim 1, wherein assigning the respective vectors comprises assigning fuzzy membership values to each of the intervals.

6. A method for sleep diagnosis, comprising:
using a processor, defining a state machine model comprising machine states corresponding to physiological states of a patient, and comprising respective probabilities of transitions among the states;
using one or more sensors, receiving biomedical signals from a sleeping patient over a given time period;
using the processor, segmenting the biomedical signals into a sequence of segments, and determining one or more respective features of each of the segments;
using the processor, assigning respective state classifications to the segments responsively to the respective features and to the probabilities of the transitions among the states of the state machine model; and
using the processor, evaluating a condition of the patient during the given time period responsively to the state classifications.

7. The method according to claim 6, wherein the physiological states comprise sleep stages, and wherein evaluating the condition comprises classifying sleep stages of the patient based on the state classifications.

8. The method according to claim 6, wherein defining the state machine model comprises defining a Hidden Markov Model (HMM).

9. The method according to claim 6, wherein assigning the respective state classifications comprises assigning respective fuzzy membership values to the segments, and determining the state classifications responsively to the fuzzy membership values.

10. Apparatus for sleep diagnosis, comprising:
one or more sensors, which are adapted to receive biomedical signals from a sleeping patient over a given time period; and
a processor, which is adapted to extract features from the biomedical signals and to group the features into multiple clusters, to assign respective vectors of membership values to a plurality of intervals within the given time period, each membership value indicating a degree of association between the biomedical signals in a corresponding interval and a respective cluster among the multiple clusters, and to evaluate a condition of the patient responsively to the vectors,
wherein the processor is adapted to receive a state machine model comprising machine states corresponding to physiological states of the patient, and to determine the condition using the state machine model.

11. Apparatus for sleep diagnosis, comprising:
one or more sensors, which are adapted to receive biomedical signals from a sleeping patient over a given time period; and
a processor, which is adapted to receive a definition of a state machine model comprising machine states corresponding to physiological states of a patient, the model comprising respective probabilities of transitions among the states,
wherein the processor is adapted to segment the biomedical signals into a sequence of segments and determine one or more respective features of each of the segments, to assign respective state classifications to the segments responsively to the respective features and to the probabilities of the transitions among the states of the state machine model, and evaluate a condition of the patient during the given time period responsively to the state classifications.

12. The apparatus according to claim 11, wherein the physiological states comprise sleep stages, and wherein the processor is adapted to classify sleep stages of the patient based on the state classifications.

13. The apparatus according to claim 11, wherein the state machine model comprises a Hidden Markov Model (HMM).

14. The apparatus according to claim 11, wherein the processor is adapted to assign respective fuzzy membership values to the segments, and to determine the state classifications responsively to the fuzzy membership values.

* * * * *